(12) United States Patent
Lally et al.

(10) Patent No.: US 11,833,043 B2
(45) Date of Patent: Dec. 5, 2023

(54) HEART VALVE PROSTHESES INCLUDING TORQUE ANCHORING MECHANISMS AND DELIVERY DEVICES FOR THE HEART VALVE PROSTHESES

(71) Applicant: Medtronic Vascular, Inc., Santa Rosa, CA (US)

(72) Inventors: Marian Lally, Galway (IE); Patrick Griffin, Galway (IE); Luke McCartney, Antrim (IE)

(73) Assignee: Medtronic Vascular, Inc., Santa Rosa, CA (US)

( * ) Notice: Subject to any disclaimer, the term of this patent is extended or adjusted under 35 U.S.C. 154(b) by 348 days.

(21) Appl. No.: 17/163,963

(22) Filed: Feb. 1, 2021

(65) Prior Publication Data

US 2021/0177592 A1 Jun. 17, 2021

Related U.S. Application Data

(63) Continuation of application No. 15/421,817, filed on Feb. 1, 2017, now Pat. No. 10,905,550.

(51) Int. Cl.
*A61F 2/24* (2006.01)
*A61M 25/10* (2013.01)

(52) U.S. Cl.
CPC .......... *A61F 2/2433* (2013.01); *A61F 2/2409* (2013.01); *A61F 2/2418* (2013.01); *A61F 2/2436* (2013.01); *A61F 2/2439* (2013.01); *A61F 2210/0014* (2013.01); *A61F 2220/0016* (2013.01); *A61F 2230/0034* (2013.01); *A61M 25/1002* (2013.01)

(58) Field of Classification Search
CPC .... A61F 2/2418; A61F 2/2412; A61F 2/2445; A61F 2/2454; A61F 2/2457; A61F 2/2403; A61F 2/2409; A61F 2/848; A61F 2/24; A61F 2/2427; A61F 2/243; A61B 2017/1107; A61B 2017/1135; A61B 17/11
See application file for complete search history.

(56) References Cited

U.S. PATENT DOCUMENTS

| | | | |
|---|---|---|---|
| 3,686,740 A | * | 8/1972 | Shiley .................. A61F 2/2409 29/445 |
| 5,545,214 A | | 8/1996 | Stevens |
| 6,790,229 B1 | | 9/2004 | Berreklouw |
| 6,821,297 B2 | | 11/2004 | Snyders |
| 6,830,585 B1 | | 12/2004 | Artof et al. |
| 7,025,780 B2 | | 4/2006 | Gabbay |

(Continued)

FOREIGN PATENT DOCUMENTS

DE 102012111984 A1 6/2014
WO 2006138173 A2 12/2006
(Continued)

*Primary Examiner* — Timothy J Neal
*Assistant Examiner* — Andrew P. Restaino
(74) *Attorney, Agent, or Firm* — Medler Ferro Woodhouse & Mills PLLC

(57) ABSTRACT

A delivery device for delivery and deployment of a heart valve prosthesis with a torque anchoring mechanism includes a balloon having a shaped surface configured to engage a corresponding shaped surface of the heart valve prosthesis. The balloon is configured to rotate about a central longitudinal axis of the delivery device to rotate the heart valve prosthesis.

19 Claims, 41 Drawing Sheets

(56) References Cited

U.S. PATENT DOCUMENTS

| | | |
|---|---|---|
| 7,125,418 B2 | 10/2006 | Duran et al. |
| 7,147,663 B1 | 12/2006 | Berg et al. |
| 7,524,330 B2 | 4/2009 | Berreklouw |
| 7,569,072 B2 | 8/2009 | Berg et al. |
| 7,803,184 B2 | 9/2010 | McGuckin, Jr. et al. |
| 7,806,920 B2 | 10/2010 | Duran |
| 7,837,727 B2 | 11/2010 | Goetz et al. |
| 7,947,075 B2 | 5/2011 | Goetz et al. |
| 7,981,151 B2 | 7/2011 | Rowe |
| 8,034,099 B2 | 10/2011 | Pellegrini |
| 8,167,935 B2 | 5/2012 | McGuckin, Jr. et al. |
| 8,366,766 B2 | 2/2013 | Berreklouw |
| 8,460,366 B2 | 6/2013 | Rowe |
| 8,623,079 B2 | 1/2014 | Savage et al. |
| 8,870,949 B2 | 10/2014 | Rowe |
| 8,894,702 B2 | 11/2014 | Quadri et al. |
| 11,141,268 B2 * | 10/2021 | Hacohen ............ A61F 2/2409 |
| 2002/0010489 A1 | 1/2002 | Grayzel et al. |
| 2003/0069635 A1 | 4/2003 | Cartledge et al. |
| 2004/0044406 A1 * | 3/2004 | Woolfson ............ A61F 2/848 |
| | | 623/2.11 |
| 2004/0236418 A1 | 11/2004 | Stevens |
| 2005/0038468 A1 | 2/2005 | Panetta et al. |
| 2005/0049692 A1 | 3/2005 | Numamoto et al. |
| 2006/0259135 A1 | 11/2006 | Navia et al. |
| 2006/0271151 A1 | 11/2006 | McGarry et al. |
| 2007/0129794 A1 | 6/2007 | Realyvasquez |
| 2008/0065011 A1 | 3/2008 | Marchand et al. |
| 2008/0133002 A1 | 6/2008 | Gelbart et al. |
| 2009/0254113 A1 | 10/2009 | Nolan et al. |
| 2011/0213401 A1 | 9/2011 | Grayzel et al. |
| 2011/0251676 A1 | 10/2011 | Sweeney et al. |
| 2011/0313515 A1 | 12/2011 | Quadri et al. |
| 2012/0035703 A1 | 2/2012 | Lutter et al. |
| 2012/0035713 A1 | 2/2012 | Lutter et al. |
| 2012/0078360 A1 | 3/2012 | Rafiee |
| 2012/0095551 A1 | 4/2012 | Navia et al. |
| 2012/0215303 A1 | 8/2012 | Quadri et al. |
| 2012/0226342 A1 | 9/2012 | Mickley |
| 2012/0283824 A1 | 11/2012 | Lutter et al. |
| 2013/0131788 A1 | 5/2013 | Quadri et al. |
| 2013/0138203 A1 | 5/2013 | Quadri |
| 2013/0138207 A1 | 5/2013 | Quadri et al. |
| 2013/0144378 A1 | 6/2013 | Quadri et al. |
| 2013/0144380 A1 | 6/2013 | Quadri et al. |
| 2013/0144381 A1 | 6/2013 | Quadri et al. |
| 2013/0184813 A1 | 7/2013 | Quadri et al. |
| 2013/0211491 A1 | 8/2013 | Berreklouw |
| 2013/0238088 A1 | 9/2013 | Navia et al. |
| 2013/0253642 A1 | 9/2013 | Brecker |
| 2013/0253643 A1 | 9/2013 | Rolando et al. |
| 2013/0261741 A1 * | 10/2013 | Accola ............ A61B 17/12136 |
| | | 623/2.11 |
| 2013/0282114 A1 | 10/2013 | Schweich, Jr. et al. |
| 2013/0345799 A1 | 12/2013 | Lafontaine |
| 2014/0052237 A1 | 2/2014 | Lane et al. |
| 2014/0066896 A1 | 3/2014 | Tilson et al. |
| 2014/0088696 A1 | 3/2014 | Figulla et al. |
| 2014/0100653 A1 | 4/2014 | Savage et al. |
| 2014/0222142 A1 | 8/2014 | Kovalsky et al. |
| 2014/0277390 A1 | 9/2014 | Ratz et al. |
| 2014/0277411 A1 * | 9/2014 | Bortlein .............. A61F 2/243 |
| | | 623/2.11 |
| 2014/0277422 A1 | 9/2014 | Ratz et al. |
| 2014/0277427 A1 | 9/2014 | Ratz et al. |
| 2014/0303719 A1 | 10/2014 | Cox et al. |
| 2014/0309731 A1 | 10/2014 | Quadri et al. |
| 2014/0364944 A1 | 12/2014 | Lutter et al. |
| 2015/0039081 A1 | 2/2015 | Costello |
| 2015/0039083 A1 | 2/2015 | Rafiee |
| 2015/0066136 A1 | 3/2015 | Smith et al. |
| 2015/0066140 A1 | 3/2015 | Quadri et al. |
| 2017/0112620 A1 * | 4/2017 | Curley .............. A61F 2/2418 |

FOREIGN PATENT DOCUMENTS

| | | |
|---|---|---|
| WO | 2012142189 A1 | 10/2012 |
| WO | 2013175468 A2 | 11/2013 |
| WO | 2016168062 A1 | 10/2016 |

* cited by examiner

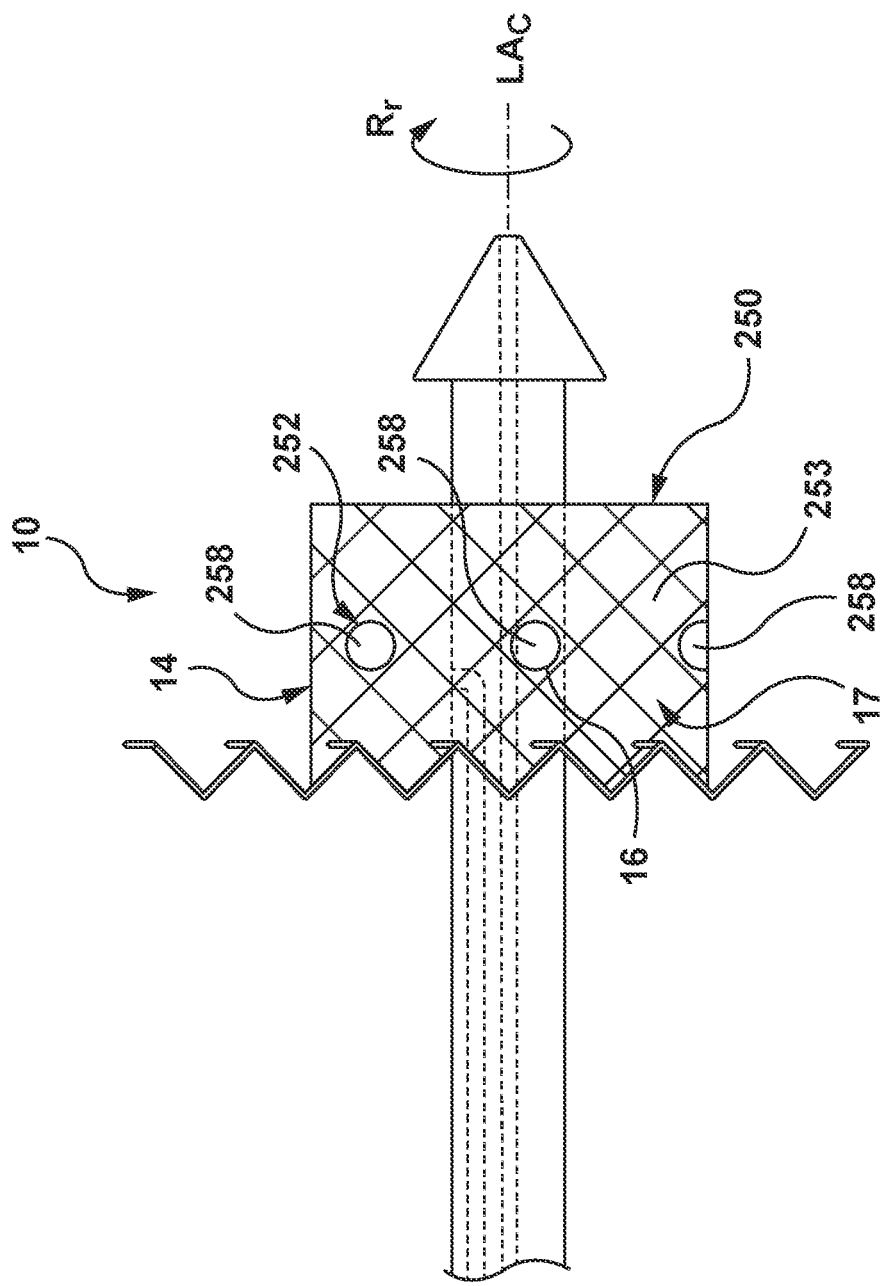

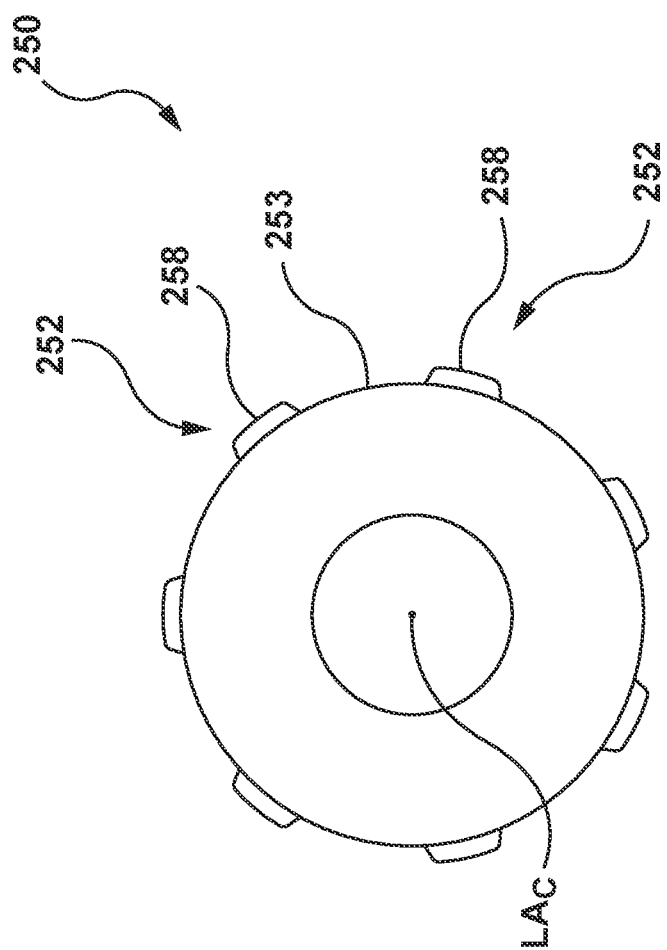

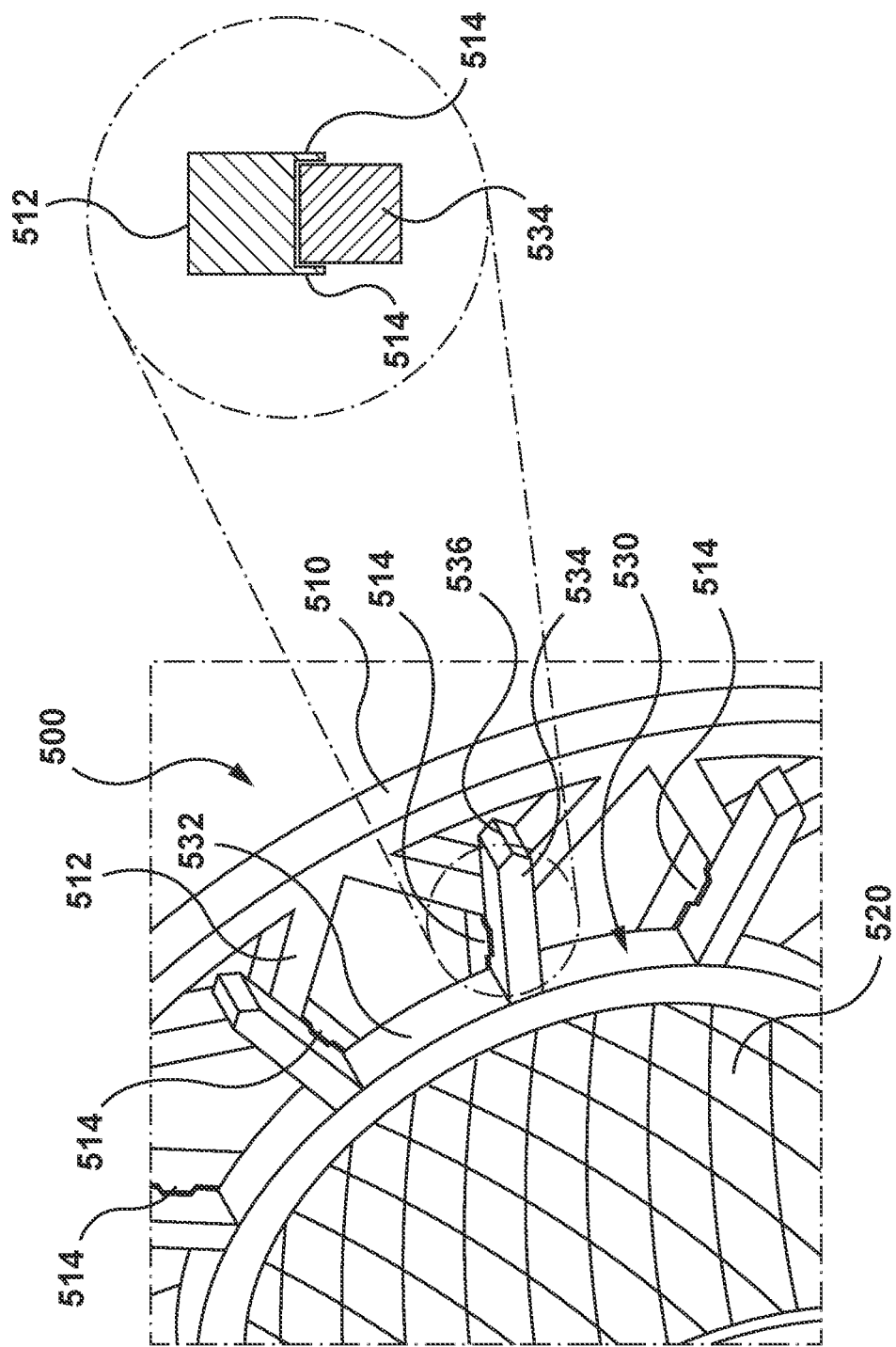

HEART VALVE PROSTHESES INCLUDING TORQUE ANCHORING MECHANISMS AND DELIVERY DEVICES FOR THE HEART VALVE PROSTHESES

CROSS-REFERENCE TO RELATED APPLICATIONS

This application is a continuation of U.S. patent application Ser. No. 15/421,817, filed Feb. 1, 2017, now U.S. Pat. No. 10,905,550, the contents of which are incorporated by reference herein in their entirety.

FIELD OF THE INVENTION

The present invention relates to systems and methods for percutaneous implantation of a heart valve prosthesis. More particularly, it relates to the systems and methods for anchoring a stented prosthetic heart valve via transcatheter implantation.

BACKGROUND

Heart valves are sometimes damaged by disease or by aging, resulting in problems with the proper functioning of the valve. Heart valve replacement via surgical procedure is often used for patients suffering from valve dysfunctions. Traditional open surgery inflicts significant patient trauma and discomfort, requires extensive recuperation times, and may result in life-threatening complications.

To address these concerns, efforts have been made to perform cardiac valve replacements using minimally invasive techniques. In these methods, laparoscopic instruments are employed to make small openings through the patient's ribs to provide access to the heart. While considerable effort has been devoted to such techniques, widespread acceptance has been limited by the clinician's ability to access only certain regions of the heart using laparoscopic instruments.

Still other efforts have been focused upon percutaneous transcatheter (or transluminal) delivery of replacement cardiac valves to solve the problems presented by traditional open surgery and minimally invasive surgical methods. In such methods, a heart valve prosthesis is compacted for delivery in a delivery device, also known as a delivery catheter and then advanced, for example through an opening in the native vasculature, and through to the heart, where the heart valve prosthesis is then deployed in the valve annulus (e.g., the mitral valve annulus).

Various types and configurations of heart valve prostheses are available for percutaneous valve replacement procedures. In general, heart valve prosthetic designs attempt to replicate the function of the valve being replaced and thus will include valve leaflet-like structures. Heart valve prostheses are generally formed by attaching a bioprosthetic valve to a frame made of a wire or a network of wires. Such heart valve prostheses can be contracted radially to introduce the heart valve prosthesis into the body of the patient percutaneously through a delivery device (catheter). The heart valve prosthesis can be deployed by radially expanding it once positioned at the desired target site.

It is important the heart valve prostheses are properly anchored at the desired implantation site. In some situations, for example and not by way of limitation, the native mitral valve, it may be difficult to properly anchor the heart valve prosthesis. This may lead to unwanted migration of the heart valve prosthesis and/or paravalvular leakage (PVL).

Accordingly, there is a need for improved anchoring mechanisms for heart valve prostheses and methods to more securely anchor heart valve prostheses implanted via transcatheter delivery devices.

SUMMARY OF THE INVENTION

Embodiments hereof relate to a delivery device for delivery and deployment of a heart valve prosthesis with a torque anchoring mechanism to the site of a damaged or diseased native valve. The delivery device includes a balloon having a first uninflated configuration and a second inflated configuration. The balloon includes a shaped end that is configured to engage a corresponding shaped end of the heart valve prosthesis, and is configured to rotate about a central longitudinal axis of the delivery device. The balloon is configured to rotate the corresponding shaped end of the heart valve prosthesis.

Embodiments hereof also relate to a delivery device for delivery and deployment of a heart valve prosthesis to the site of a damaged or diseased native valve. The delivery device includes an inner shaft coupled to a handle and a tether shaft disposed above the inner shaft. The tether shaft includes a proximal shaft portion and a plurality of tethers extending from a distal portion of the proximal shaft portion. The tethers are configured to engage the proximal shaft portion of the tether shaft to the end of the heart valve prosthesis. The tether shaft is rotatable about the inner shaft and configured to correspondingly rotate the tethers and at least a portion of the heart valve prosthesis.

Embodiments hereof also relate to a method for deploying and anchoring a heart valve prosthesis with a torque anchoring mechanism at a desired implantation site. The method includes delivering the heart valve including the torque anchoring mechanism in a radially compressed configuration, in a delivery device to the desired implantation site. The heart valve prosthesis is expanded at the desired location to a radially expanded configuration. The delivery device is rotated, rotating at least a portion of the heart valve prosthesis and embedding the torque anchoring mechanism into tissue at the desire implantation site.

BRIEF DESCRIPTION OF DRAWINGS

FIG. 10B is a side cutaway illustration of the delivery device of FIG. 10A with the capsule retracted and the balloon in an inflated configuration.

FIG. 10O is an end illustration of the balloon of FIG. 10B.

FIGS. 11A-11D are illustrations of another embodiment of a heart valve prosthesis including a torque anchoring mechanism.

DETAILED DESCRIPTION

Specific embodiments of the present invention are now described with reference to the figures, wherein like reference numbers indicate identical or functionally similar elements. The terms "distal" and "proximal", when used in the following description to refer to a catheter or delivery device, are with respect to a position or direction relative to the treating clinician. Thus, "distal" and "distally" refer to positions distant from, or in a direction away from, the clinician and "proximal" and "proximally" refer to positions near, or in a direction toward, the clinician. When the terms "distal" and "proximal" are used in the following description to refer to a device to be implanted into a vessel, such as a heart valve prosthesis, they are used with reference to the direction of blood flow. Thus, "distal" and "distally" refer to positions in a downstream direction with respect to the direction of blood flow and "proximal" and "proximally" refer to an upstream direction with respect to the direction of blood flow.

The following detailed description is merely exemplary in nature and is not intended to limit the invention or the application and uses of the invention. Furthermore, there is no intention to be bound by any expressed or implied theory presented in the preceding technical field, background, brief summary, or the following detailed description.

As referred to herein, a heart valve prosthesis used in accordance with and/or as part of the various systems, devices, and methods of the present disclosure may include a wide variety of different configurations, such as a bioprosthetic heart valve having tissue leaflets or a synthetic heart valve having polymeric, metallic, or tissue-engineered leaflets, and can be specifically configured for replacing any heart valve.

In general terms, the heart valve prosthesis, or stented prosthetic heart valve as it is sometimes referred to, of the present disclosure includes a frame supporting a valve structure (tissue or synthetic), with the frame having a normal, radially expanded configuration that is collapsible to a radially compressed configuration for loading within or on a delivery device. The stent is may be constructed to self-deploy or expand when released from the delivery device, or may be balloon-expandable.

Figure 1:
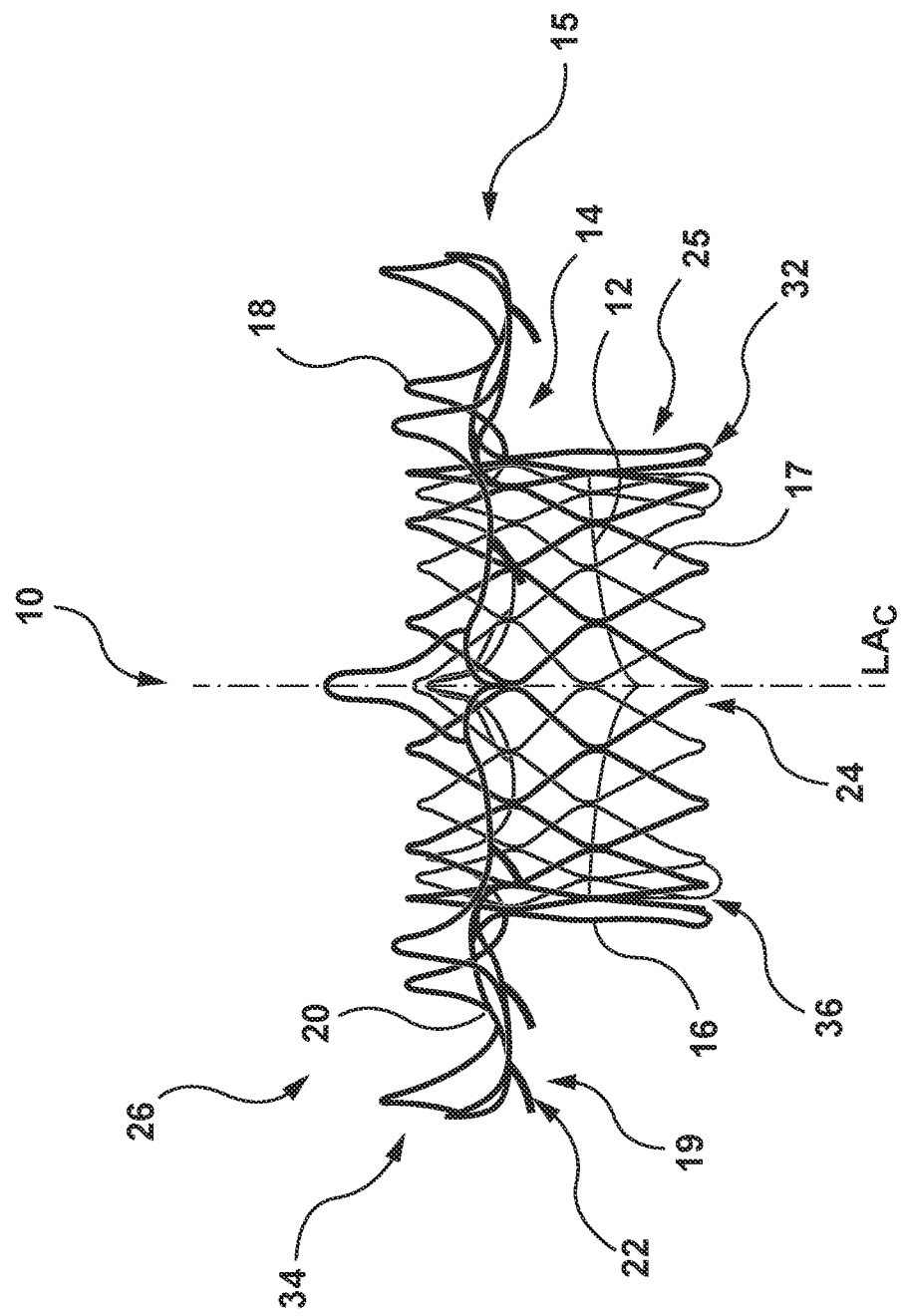
FIG. 1 is a perspective illustration of an embodiment of a heart valve prosthesis with a torque anchoring mechanism according to an embodiment hereof.

FIG. 1 shows an embodiment of a heart valve prosthesis 10. FIG. 1 illustrates heart valve prosthesis 10 in a radially expanded configuration. Heart valve prosthesis 10 includes a frame 14 and a prosthetic valve 12 coupled to the frame 14. Heart valve prosthesis 10 includes a radially collapsed configuration and the radially expanded configuration. Heart valve prosthesis 10 also includes a first end 26 and a second end 32 opposite first end 26. Frame 14 is generally tubular and defines a central passage 24, and includes a first end 34 and a second end 36. In the embodiment shown in FIG. 1, first end 34 of frame 14 defines first end 26 of heart valve prosthesis 10. Similarly, second end 36 of frame 14 defines second end 32 of heart valve prosthesis 10. Those skilled in the art would recognize that other features, such as skirts or arms may be included as part of heart valve prosthesis 10. In the embodiment shown, first end 26 of heart valve prosthesis 10 is the proximal or inflow end, and second end 32 of heart valve prosthesis 10 is the distal or outflow end. Also, first end 34 of frame 14 is flared radially outwardly, as show in FIG. 1. This outward flare at first end 34 forms an inflow rim 15 that is configured to contact an atrial side of a native mitral valve annulus. Further, although inflow rim 15 is shown as generally circular, inflow rim may be other shapes to conform to the anatomy adjacent the native mitral valve, such as but not limited to D-shaped. A portion of frame 14 may also be described as an outflow portion 25. Outflow portion 25 is generally tubular and is configured to extend through the leaflets of the native valve complex. Although heart valve prosthesis 10 as shown is configured for placement at the site of a native mitral valve, heart valve prosthesis 10 may be used at other implantation sites, such as, but not limited to, sites of other native heart valves.

Frame 14 is a support structure that comprises struts 16 arranged relative to each other with a plurality of open spaces 17 there between. Frame 14 provides a desired compressibility and expansion force at the desired implantation site. Frame 14 also provides support for prosthetic valve 12. Prosthetic valve 12 is coupled to and disposed within frame 14. In the embodiment of FIG. 1, a radially outward portion of inflow rim 15 bends such that the radially outward portion of inflow rim 15 extends generally longitudinally away from second end 36 of frame 14. Struts 16 of inflow rim 15 bend and form a plurality of peaks 18 and valleys 20 at a first end of inflow rim 15.

A plurality of torque anchoring mechanisms 22 are coupled to inflow rim 15. In the embodiment shown in FIG. 1, torque anchoring mechanism 22 are coupled to valleys 20 of inflow rim 15, but may be coupled to other portions of inflow rim 15. Torque anchoring mechanisms 22 are configured such that when heart valve prosthesis 10 is in the radially expanded configuration at a desired implantation site, and at least a portion of heart valve prosthesis 10 is rotated, torque anchoring mechanisms 22 are embedded into tissue at the desired implantation site. As shown in FIG. 1, torque anchoring mechanisms 22 extend clockwise. However, they may extend counter-clockwise or partially angled in either direction. Further, torque anchoring mechanisms 22 may generally extend from an underside 19 of inflow rim 15. The underside 19 of inflow rim 15 is the surface facing the native mitral valve annulus when the heart valve prosthesis 10 is deployed with inflow rim 15 on the atrial side of the native mitral valve annulus (i.e., the surface of the inflow rim facing the outflow end). Torque anchoring mechanisms 22 may be barbs, clips, hooks, arrows or similar devices configured to embed into tissue at the desired implantation site. While FIG. 1 shows each torque anchoring mechanism 22 as single wire, this is not limiting and other configurations of torque anchoring mechanisms may be used.

Frame 14 may be formed, for example, and not by way of limitation, of nickel titanium alloys (e.g., Nitinol), nickel-cobalt-chromium-molybdenum alloys (e.g., MP35N), cobalt-chromium-tungsten-nickel alloys (L605), stainless steel, high spring temper steel, or any other metal or suitable for purposes of the present disclosure. Torque anchoring mechanisms 22 may be formed from the same types of materials as frame 14. Torque anchoring mechanisms 22 may be extensions of struts 16, or may be coupled to frame 14, for example, and not by way of limitation, by fusing, welding, adhesive, sutures, snap-fit, interference fit, other mechanical engagements, or other means suitable for the purposed described herein.

With the above understanding of heart valve prosthesis 10 in mind, a delivery device 100 consistent with components, methods, and procedures of the current disclosure is shown in FIGS. 2-5. In an embodiment, delivery device 100 generally includes a handle 140, an outer shaft assembly 110 including a capsule 107, an inner shaft assembly 104, and a balloon 150 (not shown in FIG. 2). Delivery device 100 may be any standard construction delivery device, such as, but not limited to, multi-lumen or coaxial construction delivery devices. In other embodiments, capsule 107 is not required, such as when using a balloon expandable heart valve prosthesis, or a self-expandable heart valve prosthesis with other means to maintain the heart valve prosthesis in a radially collapsed configuration. A guidewire lumen 123 is disposed through inner shaft assembly 104 such that delivery device 100 may be advanced over a guidewire (not shown) disposed within guidewire lumen 123. Delivery device 100 may be made from any suitable material, such as, but not limited to polyethylene (PE), polyethylene terephthalate (PET), polyether block amide (PEBA, such as PEBAX®), nylons, polyurethanes, polyvinylchloride (PVC), and metal hypotubes such as stainless steel.

Figure 2:
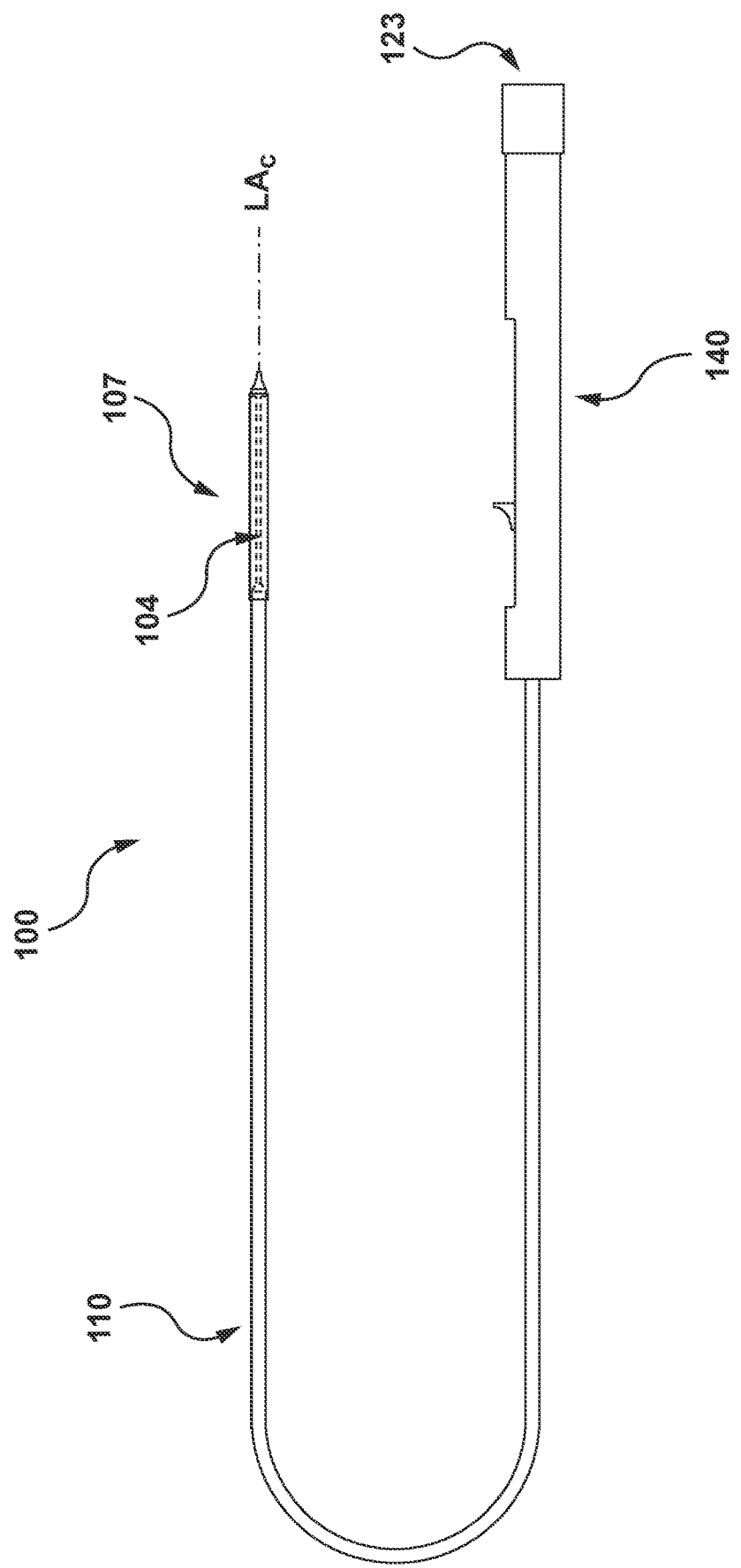
FIG. 2 is a side view illustration of an embodiment of a delivery device according to an embodiment hereof.

Delivery device 100 is used for percutaneously delivering, implanting, and anchoring heart valve prosthesis 10 with torque anchoring mechanisms 22 according to an embodiment of the present invention. FIG. 2 illustrates an embodiment of delivery device 100 with heart valve prosthesis 10 in the radially collapsed configuration disposed within capsule 107 of outer shaft assembly 110. In other embodiments, heart valve prosthesis 10 may be mounted on a balloon without a capsule, or a self-expandable heart valve prosthesis may be mounted with other means to maintain the heart valve prosthesis in a radially collapsed configuration. Delivery device 100 and heart valve prosthesis 10 are configured such that when heart valve prosthesis 10 is positioned at a desired implantation site and in the radially expanded configuration, rotating delivery device 100 rotates at least a portion of heart valve prosthesis 10, and torque anchoring mechanism 22 is embedded in tissue at the implantation site, as will be described in greater detail herein.

Components in accordance with an exemplary embodiment of delivery device 100 of FIG. 2 are presented in greater detail in FIGS. 3-6B. Various features of the components of delivery device 100 reflected in FIGS. 2-6B and described below can be modified or replaced with differing structures and/or mechanisms. The components of delivery device 100 may assume different forms and construction. Therefore, the following detailed description is not meant to be limiting. Further, the systems and functions described below can be implemented in many different embodiments of hardware. Any actual hardware described is not meant to be limiting. The operation and behavior of the systems and methods presented are described with the understanding that modifications and variations of the embodiments are possible given the level of detail presented.

Figure 3:
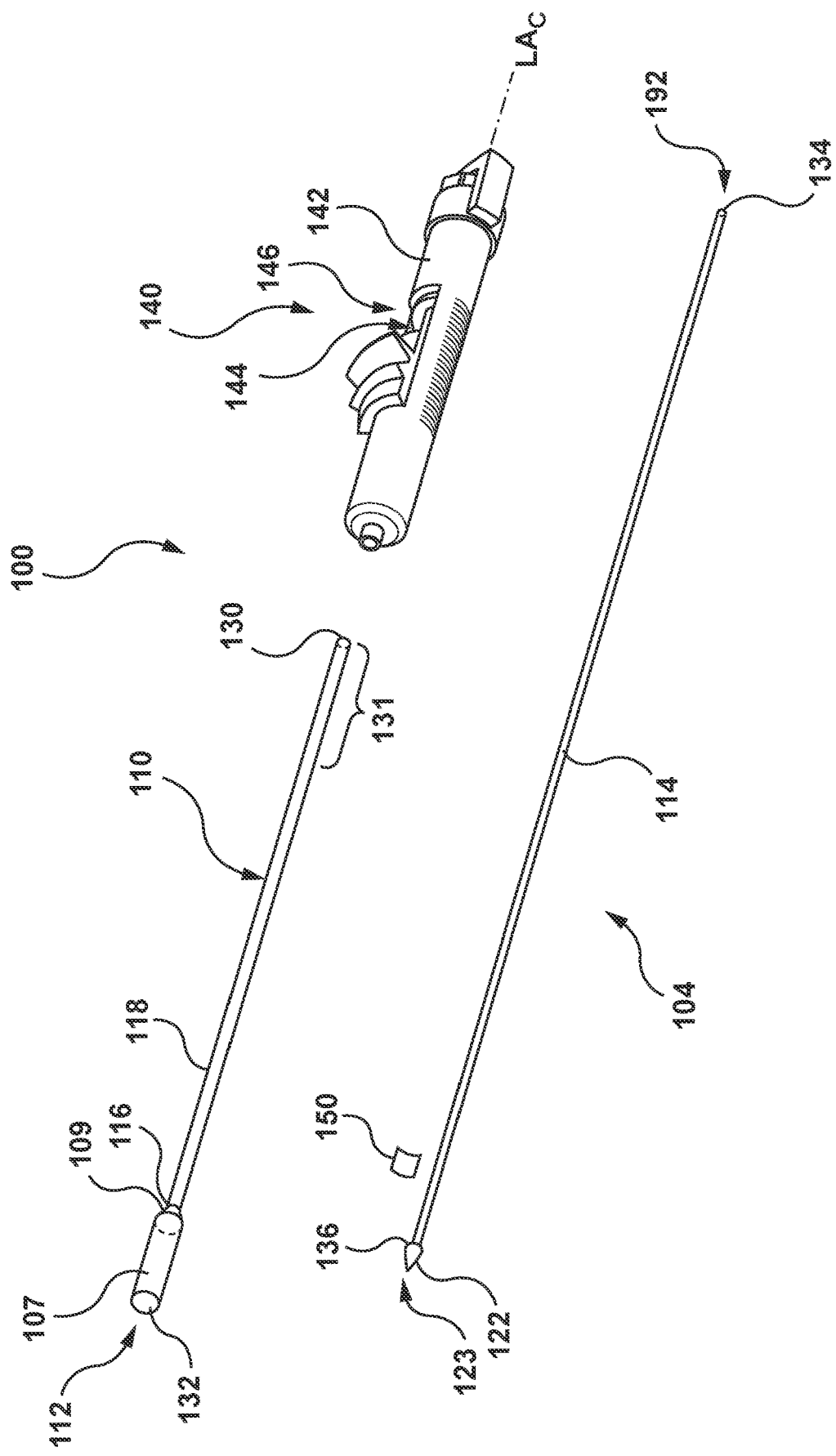
FIG. 3 is an exploded perspective illustration of the delivery device of FIG. 2.
Figure 4:
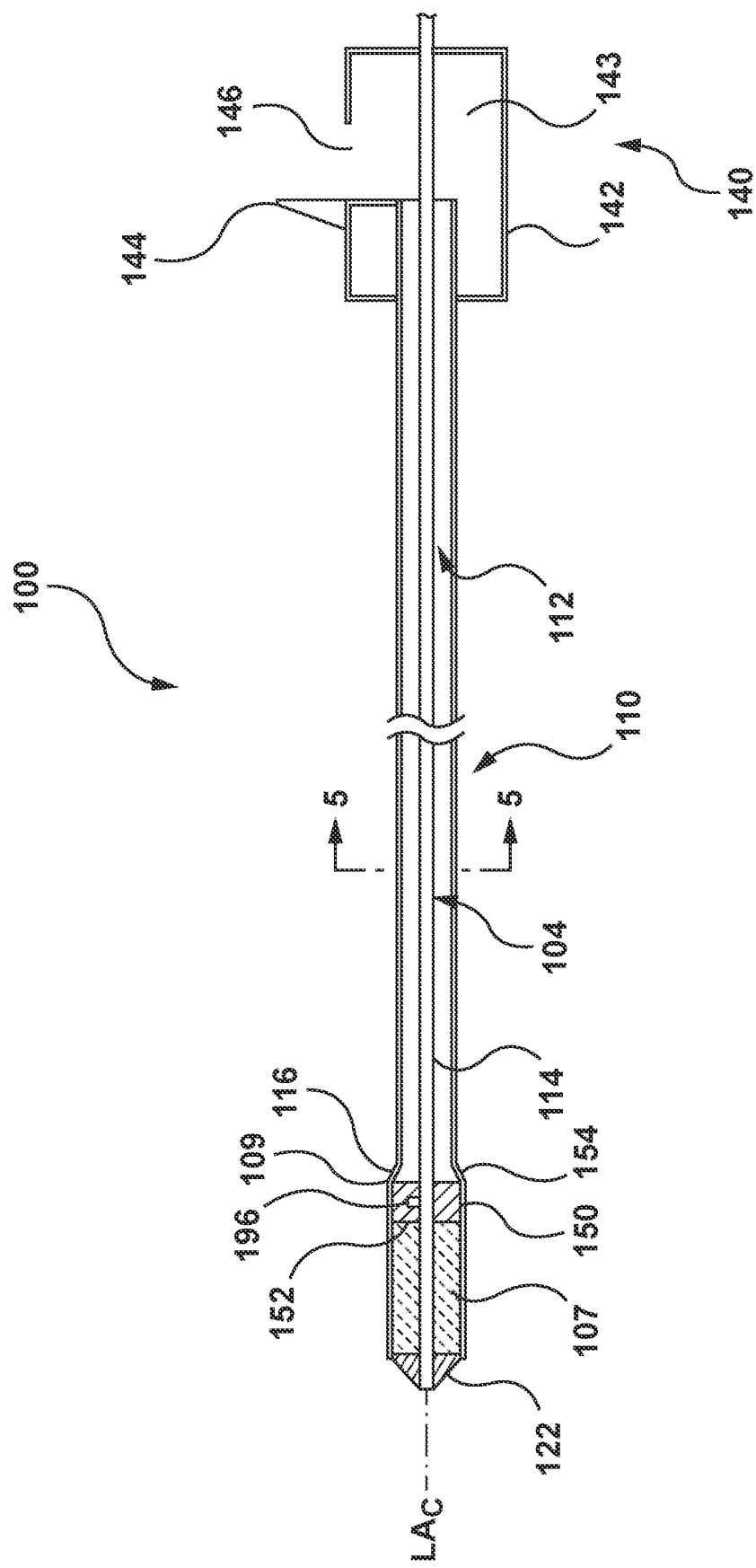
FIG. 4 is a side cutaway illustration of the delivery device of FIG. 2.

In an embodiment shown schematically in FIGS. 3-4, handle 140 may include a housing 142 and an actuator mechanism 144. More particularly, handle 140 includes a cavity 143 (FIG. 4) defined by housing 142 and configured to receive portions of actuator mechanism 144. In an embodiment shown in FIGS. 2-4, housing 140 may include a longitudinal slot 146 through which actuator mechanism 144 extends for interfacing by a user. Handle 140 provides a surface for convenient handling and grasping by a user, and may have a generally cylindrical shape as shown. While handle 140 of FIGS. 2-4 is shown with a cylindrical shape, it is not meant to limit the design, and other shapes and sizes are contemplated based on the application requirements. Actuator mechanism 144 is generally constructed to provide selective retraction/advancement of outer shaft assembly 110. Although shown as a slide mechanism, other constructions and/or devices may be used to retract/advance outer shaft assembly 110, such as, but to limited to rotating mechanisms, sliding mechanisms that are coaxially disposed over inner shaft assembly 104, combinations of rotating and sliding mechanisms, and other advancement/retraction mechanisms known to those skilled in the art.

Outer shaft assembly 110 is slidably disposed over inner shaft assembly 104. With reference to FIGS. 3-4, in an embodiment, outer shaft assembly 110 includes a proximal shaft 118 and a capsule 107, and defines a lumen 112 extending from a proximal end 130 of proximal shaft 118 to a distal end 132 of capsule 107. Although outer shaft 110 is described herein as including capsule 107 and proximal shaft 118, capsule 107 may simply be an extension of proximal shaft 118. Further, outer shaft 110 may be referred to as a sheath or outer sheath. Proximal shaft 118 is configured for fixed connection to capsule 107 at a connection point 116 at a proximal end 109 of capsule 107 by fusing, welding, adhesive, sutures, or other means suitable for the purposes described herein. Alternatively, proximal shaft 118 and capsule 107 may be unitary. Proximal shaft 118 extends proximally from capsule 107 and proximal shaft 118 is configured for connection to handle 140. More particularly, proximal shaft 118 extends proximally into housing 142 of handle 140 and a proximal portion 131 of proximal shaft 118 is connected to actuator mechanism 144 of handle 140. Proximal portion 131 is coupled to actuator mechanism 144 such that movement of actuator mechanism 144 causes outer shaft assembly 110 to move relative inner shaft assembly 104. Proximal shaft 118 may be coupled to actuator mechanism 144, for example, and not by way of limitation, by adhesives, welding, clamping, and other coupling devices as appropriate. Outer shaft assembly 110 is thus movable relative to handle 140 and inner shaft assembly 104 by actuator mechanism 144. However, if actuator mechanism 144 is not moved and handle 140 is moved, outer shaft assembly 110 moves with handle 140, not relative to handle 140.

Inner shaft assembly 104 extends within lumen 112 of outer shaft assembly 110, as shown at least in FIG. 4. Inner shaft assembly 104 includes an inner shaft 114, a distal tip 122, and balloon 150, described in greater detail below. Inner shaft 114 extends from a proximal end 134 of inner shaft 114 to a distal end 136. Distal end 136 of inner shaft 114 is attached to distal tip 122. The components of inner shaft assembly 104 combine to define a guidewire lumen 123, which is sized to receive an auxiliary component such as a guidewire (not shown) and an inflation lumen 192, described in greater detail below. In the embodiments shown, delivery device 100 includes an over-the-wire (OTW), multi-lumen configuration with guidewire lumen 123 extending substantially the entire length of inner shaft assembly 104. However, other configurations, such as rapid exchange configurations, may also be used. Proximal end 134 of inner shaft 114 may be attached to handle 140 or may be attached to another device such as a hub. Inner shaft 114 may be coupled to handle 140, for example, and not by way of limitation, by adhesives, welding, clamping, and other coupling devices as appropriate. During sliding or longitudinal movement of outer shaft assembly 110 relative to inner shaft assembly 104, inner shaft 114 may be fixed relative to handle 140.

Figure 5:
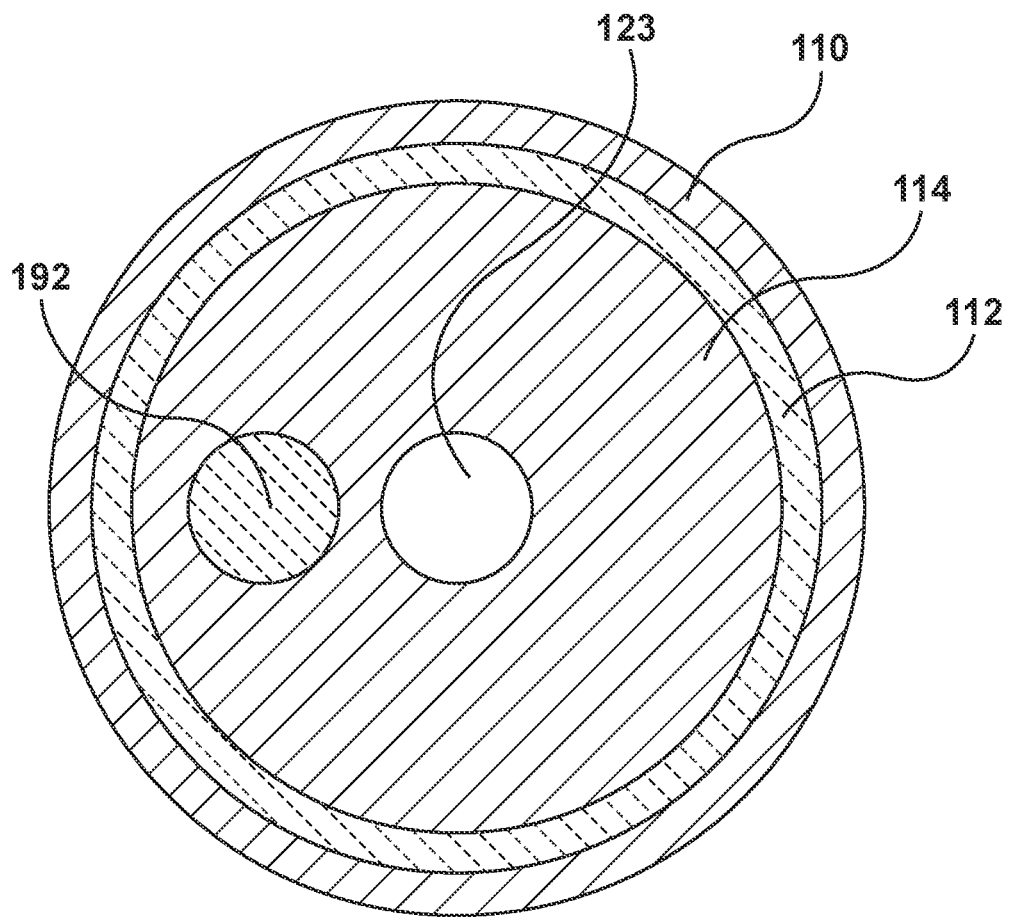
FIG. 5 is a cross section illustration of the delivery device of FIG. 2 taken along line 5-5 of FIG. 4.

As previously noted, inner shaft assembly 114 includes an inflation lumen 192 and a guidewire lumen 123 extending therethrough. FIG. 5 shows a cross-sectional view of inner shaft 114 disposed within outer shaft assembly 110. As shown in FIG. 5, guidewire lumen 123 and inflation lumen 192 extend through inner shaft 114. In the embodiment shown, inflation lumen 192 and guidewire lumen 123 are two lumens extending through a single shaft. However, other constructions may also be used.

Figure 6A:
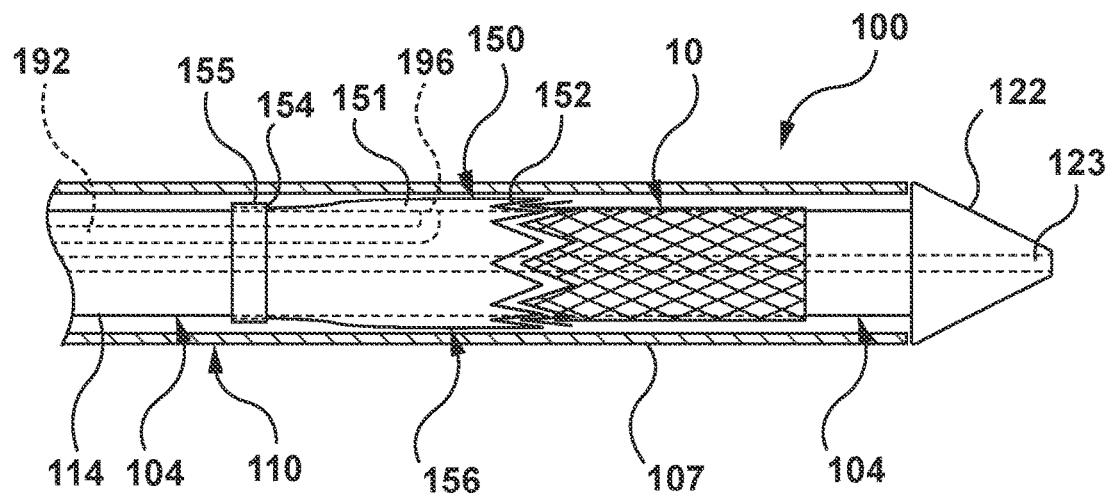
FIG. 6A a side cutaway illustration of the delivery device of FIG. 2 in a delivery configuration.
Figure 6B:
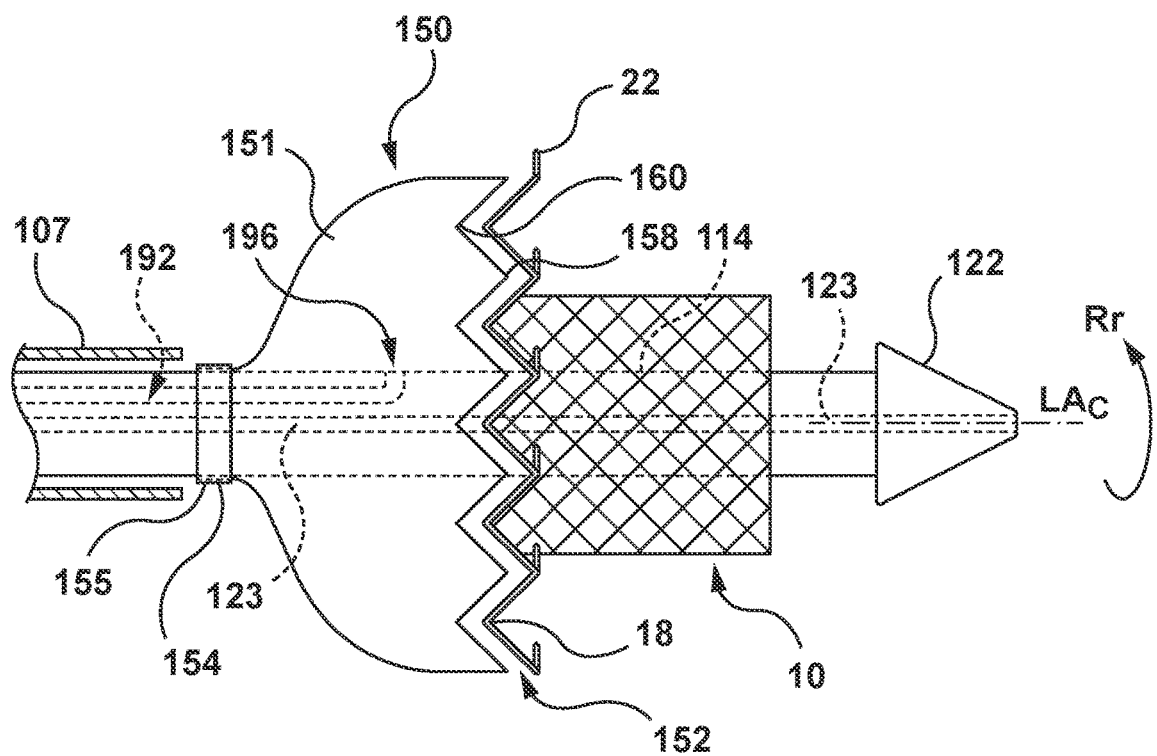
FIG. 6B is a side cutaway illustration of the delivery device of FIG. 2 with the capsule retracted and the balloon in an inflated configuration.

FIGS. 6A and 6B show a distal portion of delivery device 100 with heart valve prosthesis 10 disposed therein in a delivery configuration. Heart valve prosthesis 10 is disposed within capsule 107 of outer shaft assembly 110 and over inner shaft 114. Balloon 150 is disposed proximal of heart valve prosthesis 10 and is coupled to inner shaft 114. In the delivery configuration shown in FIG. 6A, balloon 150 is disposed within outer shaft assembly 110. In the embodiment shown in FIGS. 6A and 6B, proximal end 154 of balloon 150 is attached to inner shaft 114 at a proximal bond 155. Similarly, distal end 156 of balloon 150 is attached to inner shaft 114 at a distal bond (not shown). Inner shaft 114 continues distally beyond the distal bond of balloon 150/ inner shaft 114. Inflation lumen 192 includes an inflation port 196 that opens into an interior 151 of balloon 150.

Distal end 156 of balloon 150 may also be described as a shaped end 152. Shaped end 152 is shaped to engage first end 34 of frame 14 of heart valve prosthesis 10. In an embodiment, shaped end 152 includes a plurality of peaks 158 extending distally and valleys 160 extending proximally. Peaks 158 and valleys 160 are spaced radially from the central longitudinal axis $LA_c$. Peaks 158 and valleys 160 may be arranged opposite of peaks 18 and valleys 20 of first end 34 of frame 14; in particular, the radially outer portion of inflow rim 15 of FIG. 1. Balloon 150 is in an uninflated configuration and disposed within outer shaft assembly 110 for delivery, as shown in FIG. 6A, and is inflated to an inflated configuration to engage and rotate frame 14, as shown in FIG. 6B. Balloon 150 may be a compliant high friction balloon constructed of any suitable material, such as, but not limited to, polyethylene terephthalate (PET), nylon, or polyurethane. Moreover, balloon 150 may include a three-dimensional pattern, or texture, on an outer surface to increase engagement (frictional contact) with the heart valve prosthesis 10 when the balloon is in the second (inflated) configuration.

With the above understanding of components in mind, operation and interaction of components of the present disclosure may be explained herein. As shown in FIG. 6A, heart valve prosthesis 10 is disposed in a radially compressed configuration within capsule 107 of outer shaft assembly 110. Balloon 150 is also uninflated. Delivery device 100 is delivered to an implantation site, such as the site of a native mitral valve. When at the implantation site, outer shaft assembly 110 is retracted proximally, thereby retracting capsule 107 proximally. Capsule 107 is retracted proximally sufficiently to expose heart valve prosthesis 10. In the embodiment shown, heart valve prosthesis 10 is self-expanding. Therefore, retraction of capsule 107 enables heart valve prosthesis 10 to self-expand to the radially expanded configuration. Capsule 107 may be retracted further proximally, or may have been retracted further initially, such that balloon 150 is not covered by capsule 107. An inflation fluid, such as but not limited to saline, is injected through inflation lumen 192, out of inflation port 196, and into the interior 151 of balloon 150, thereby inflating balloon 150, as shown in FIG. 6B. Delivery device 100 may be rotated to align shaped end 152 of balloon 150 with the shaped first end 34 of frame 14 of heart valve prosthesis 10, if necessary. Delivery device 100 may also be advanced longitudinally, if necessary, such that shaped end 152 of balloon 150 engages the shaped end first end 34 of frame 14 of heart valve prosthesis 10, as shown in FIG. 6B. In an engagement embodiment, peaks 158 of balloon 150 engage corresponding valleys 20 of heart valve prosthesis 10, and valleys 160 of balloon 150 engage corresponding peaks 18 of heart valve prosthesis 10.

With shaped end 152 of balloon 150 engaged with shaped first end 24 of frame 14 of heart valve prosthesis 10, delivery device 100 may be rotated in a direction $R_r$ relative to central longitudinal axis $LA_c$, thereby rotating shaped end 152 of balloon 150 in direction $R_r$ such that shaped end 152 applies a rotational torque in direction $R_r$ to engaged corresponding shaped first end 34 of frame 14. This rotational torque rotates heart valve prosthesis 10 in direction $R_r$ such that torque anchoring mechanisms 22 are embedded in tissue at the desired implantation site. Stated another way, with balloon 150 inflated, heart valve prosthesis 10 in the radially expanded configuration, and shaped end 152 of balloon 150 engaged with shaped first end 26 of heart valve prosthesis 10, delivery device 100 is rotated in direction $R_r$ to embed torque anchoring mechanisms 22 in tissue, thereby anchoring heart valve prosthesis 10 to tissue at the desired implantation site. Balloon 150 may then be deflated and delivery device 100 may be withdrawn from the patient, leaving heart valve prosthesis 10 implanted at the desired implantation site.

FIGS. 6A-6B shows a particular embodiment of balloon 150 and heart valve prosthesis 10. As explained above, this particular embodiment is not meant to limit the design. Therefore, for example and not by way of limitation, shaped end 152 of balloon 150 may be at proximal end 154 instead of distal end 156, and heart valve prosthesis 10 would be disposed proximal of balloon 150 such that proximal end 154 of balloon 150 could engage a shaped distal end of heart valve prosthesis 10. Further, the specific number of peaks 158 and valleys 160 of balloon 150 shown in FIGS. 6A and 6B is merely an example, and may be increased or decreased to match a corresponding number of peaks and valleys in the shaped end of heart valve prosthesis 10.

Figure 7A:
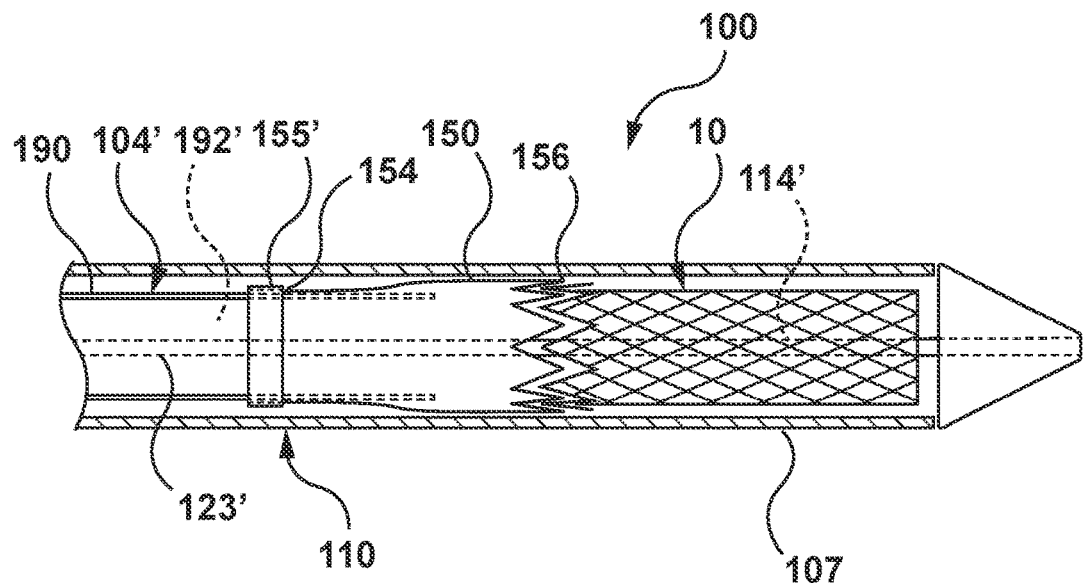
FIG. 7A is a side cutaway illustration of another embodiment of a delivery device in a delivery configuration.
Figure 7B:
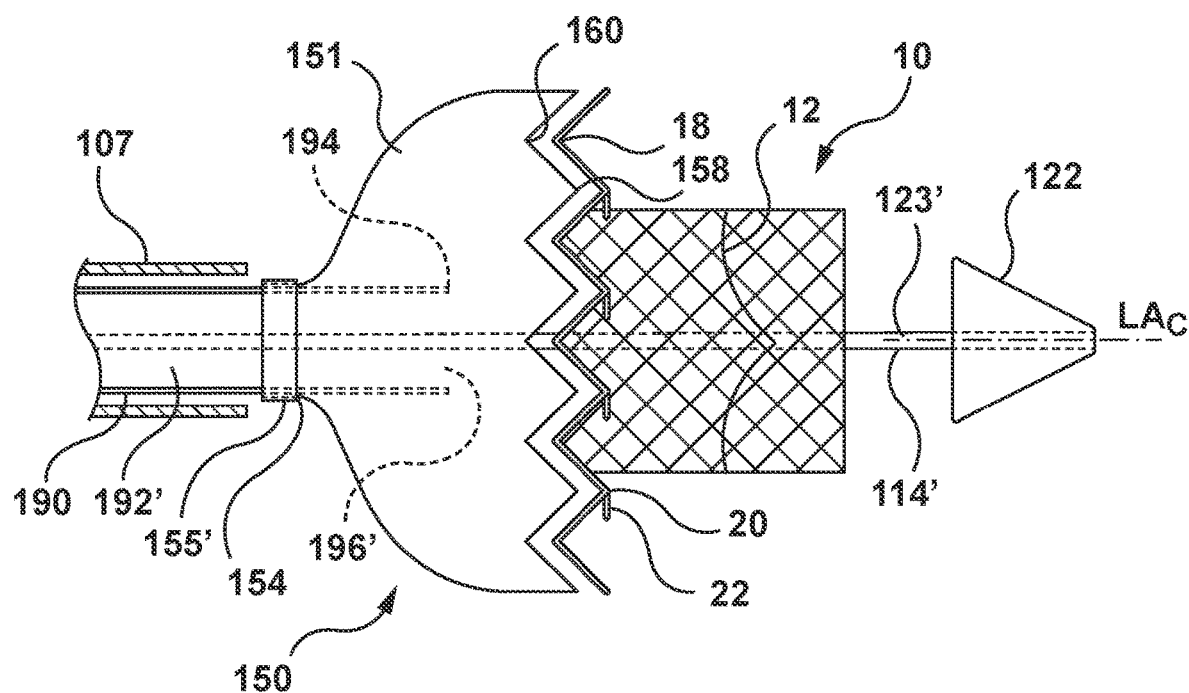
FIG. 7B is a side cutaway illustration of the delivery device of FIG. 7A with the capsule retracted and the balloon in an inflated configuration.

FIGS. 7A-7B illustrate a distal portion of another embodiment of a delivery device 100' for delivering and deploying a heart valve prosthesis 10. Delivery device 100' is similar to the embodiment of FIGS. 6A-6B, so only the differences between the embodiments will be described in detail here. Features not specifically described may be like those described with respect to the embodiment of FIGS. 6A-6B, or other embodiments described herein. In the embodiment of FIGS. 7A-7B, instead of an inner shaft with a guidewire lumen 123 and an inflation lumen 192, as described above, inner shaft assembly 104' includes a guidewire shaft 114' with an inflation shaft 190 disposed coaxially over guidewire shaft 114'. A guidewire lumen 123' extends through guidewire shaft 114' and an inflation lumen 192' is defined between an outer surface of guidewire shaft 114' and an inner surface of inflation shaft 190.

In the embodiment shown in FIGS. 7A-7B, proximal end 154 of balloon 150 is attached to inflation shaft 190 at a proximal bond 155'. Inflation shaft 190 terminates prior to distal end 156 of balloon 150 such that an inflation port 196' is formed between a distal end 194 of inflation shaft and guidewire shaft 114'. Distal end 156 of balloon 150 is attached to guidewire shaft 114' at a distal bond (not shown). When an inflation fluid is injection into inflation lumen 192', the inflation fluid exits inflation lumen 192' through inflation port 196' and into the interior 151 of balloon 150, thereby inflating balloon 150, as shown in FIG. 7B.

Figure 8A:
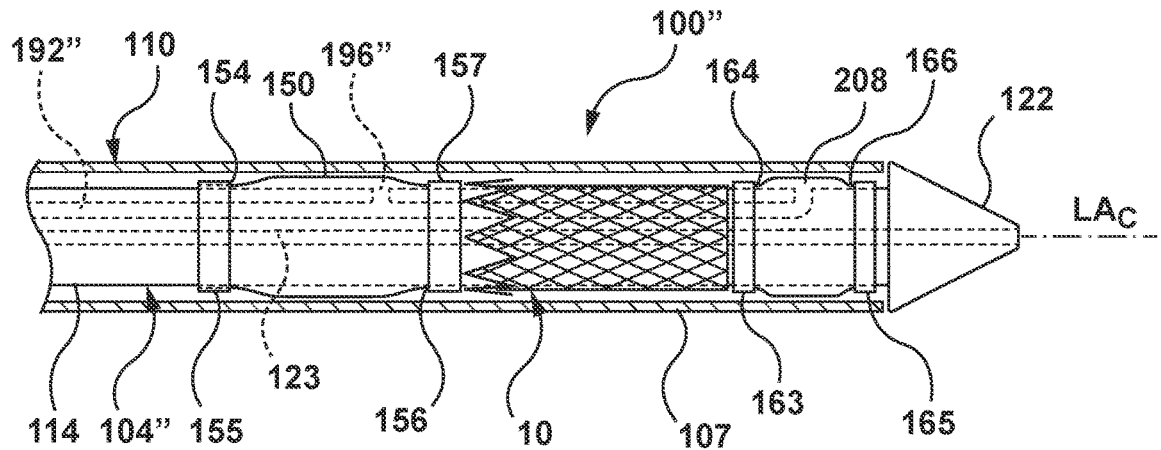
FIG. 8A is a side cutaway illustration of another embodiment of a delivery device in a delivery configuration including a second balloon in an uninflated configuration.
Figure 8B:
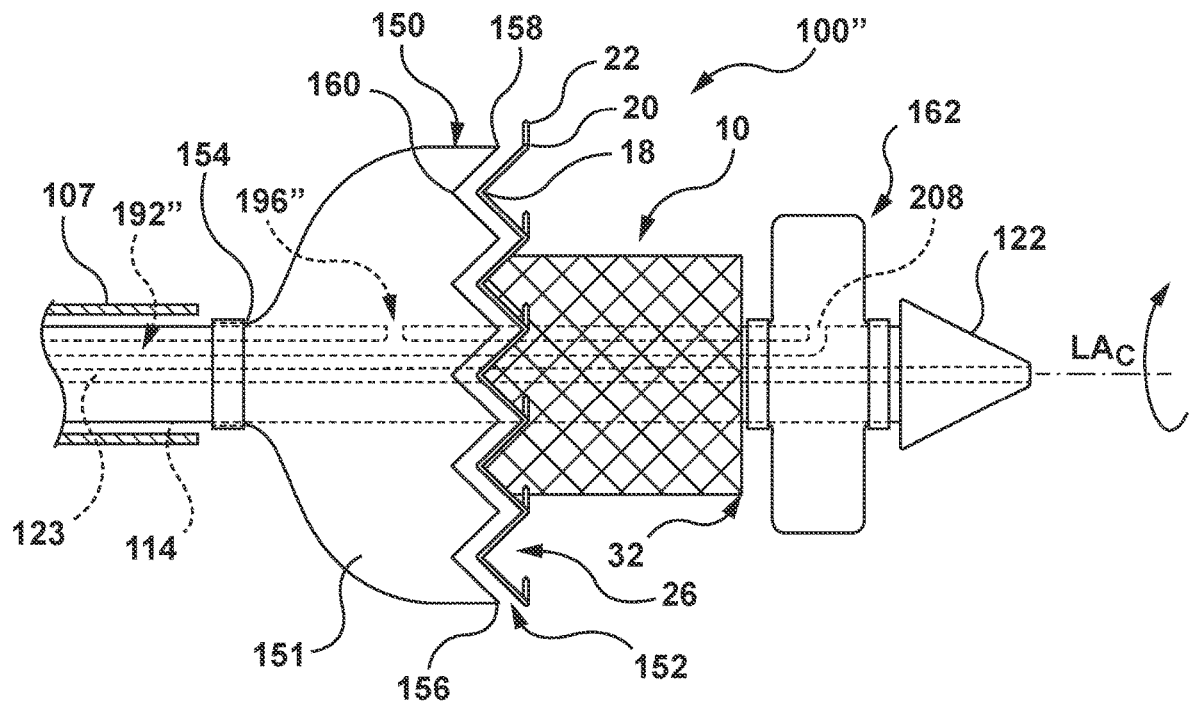
FIG. 8B is a side cutaway illustration of the delivery device of FIG. 8A with the capsule retracted and the balloons in an inflated configuration.

FIGS. 8A-8B illustrate a distal portion of another embodiment of a delivery device 100". Delivery device 100" includes a first balloon 150 and a second balloon 162. FIG. 8A shows delivery device 100" with heart valve prosthesis 10 including torque anchoring mechanisms 22 disposed therein. FIG. 8A shows delivery device 100" in a delivery configuration with first balloon 150, second balloon 162, and heart valve prosthesis 10 disposed within outer shaft assembly 110 such that first balloon 150 and second balloon 162 are uninflated, and heart valve prosthesis 10 is in a radially compressed configuration.

Delivery device 100" is similar to delivery device 100 except for the addition of second balloon 162 and extension of inflation lumen 192" distally to second balloon 162. Therefore, except for the differences specifically noted below, elements of delivery device 100" may be the same as or similar to the corresponding elements of FIGS. 2-6B. In particular, the proximal portion of delivery device 100" is not described in detail and may be similar to the proximal portion of delivery device 100 described above with respect to FIGS. 2-4.

As shown in FIGS. 8A-8B, second balloon 162 includes a proximal end 164 attached to inner shaft inner shaft 114 at a proximal bond 163 and a distal end 166 attached to inner shaft 114 at a distal bond 165. Second balloon 162 is disposed distal of heart valve prosthesis such that proximal end 164 of second balloon is adjacent second end 32 of heart valve prosthesis 10. First balloon 150 is disposed proximal of heart valve prosthesis 10 and is coupled to inner shaft 114. In the delivery configuration shown in FIG. 8A, balloon 150 is disposed within outer shaft assembly 110. In the embodiment shown in FIGS. 8A-8B, proximal end 154 of first balloon 150 is attached to inner shaft 114 at a proximal bond 155 and distal end 156 of balloon 150 is attached to inner shaft 114 at a distal bond 157. Inner shaft 114 continues distally beyond distal bond 155.

Inflation lumen 192" of inner shaft 114 is extended distally to a second inflation port 208 which opens to an interior of second balloon 162. Second inflation port 208 is disposed between proximal end 164 and distal end 166 of second balloon 162 such that inflation fluid injected through inflation lumen 192" exits second inflation portion 208 into an interior of second balloon 162, thereby inflating second balloon 162. As in the embodiment of FIGS. 6A-6B, inflation fluid injected into inflation lumen 192" exits inflation portion 196" into an interior 151 of first balloon 150, thereby inflating first balloon 150.

As in the embodiment of FIGS. 6A-6B, distal end 154 of balloon 150 is a shaped end 152 shaped to engage first end 34 of frame 14 of heart valve prosthesis 10. In an embodiment, shaped end 152 includes a plurality of peaks 158 extending distally and valleys 160 extending proximally. Peaks 158 and valleys 160 are spaced radially from the central longitudinal axis LAc. Peaks 158 and valleys 160 are arranged opposite of peaks 18 and valleys 20 of first end 34 of frame 14. First balloon 150 is in an uninflated configuration and disposed within outer shaft assembly 110 for delivery, as shown in FIG. 8A, and is inflated to an inflated configuration to engage and rotate frame 14, as shown in FIG. 8B. First balloon 150 may be a compliant high friction balloon constructed of any suitable material, such as, but not limited to, polyethylene terephthalate (PET), nylon, or polyurethane.

With the above understanding of components in mind, operation and interaction of components of the present disclosure may be explained herein. As shown in FIG. 8A, heart valve prosthesis 10 is disposed in a radially compressed configuration within capsule 107 of outer shaft assembly 110. First balloon 150 and second balloon 162 are uninflated. Delivery device 100" is delivered to an implantation site, such as the site of a native mitral valve. When at the implantation site, outer shaft assembly 110 is retracted proximally, thereby retracting capsule 107 proximally. Capsule 107 is retracted proximally sufficiently to expose heart valve prosthesis 10. In the embodiment shown, heart valve prosthesis 10 is self-expanding. Therefore, retraction of capsule 107 enables heart valve prosthesis 10 to self-expand to the radially expanded configuration. Capsule 107 may be retracted further proximally, or may have been retracted further initially, such that first balloon 150 is not covered by capsule 107. An inflation fluid, such as but not limited to saline, is injected through inflation lumen 192", out of inflation ports 196" and 206, and into the interior 151 of first balloon 150 and the interior of second balloon 162, thereby inflating first balloon 150 and second balloon 162, as shown in FIG. 8B. Delivery device 100" may be rotated to align shaped end 152 of first balloon 150 with the shaped first end 34 of frame 14 of heart valve prosthesis 10, if necessary. Delivery device 100 may also be advanced longitudinally, if necessary, such that shaped end 152 of first balloon 150 engages the shaped first end 34 of frame 14 of heart valve prosthesis 10, as shown in FIG. 8B. In an engagement embodiment, peaks 158 of first balloon 150 engage corresponding valleys 20 of heart valve prosthesis 10, and valleys 160 of first balloon 150 engage corresponding peaks 18 of heart valve prosthesis 10. In particular, shaped end 152 of first balloon 150 engages the peaks and valleys of the radially outward, bent portion of inflow rim 15 of heart valve prosthesis 10

When second balloon 162 is inflated, proximal end 164 may engage distal end 32 of heart valve prosthesis 10 when heart valve prosthesis 10 is in the radially expanded configuration, as shown in FIG. 8B. Second balloon 162 is configured to provide longitudinal stability for heart valve prosthesis 10 along central longitudinal axis $LA_c$ relative to delivery device 100" as heart valve prosthesis 10 is rotated and torque anchoring mechanisms 22 are embedded in tissue at desired implantation site. Second balloon 162 may be a compliant high friction balloon constructed of any suitable material, such as, but not limited to, polyethylene terephthalate (PET), nylon, or polyurethane.

With shaped end 152 of first balloon 150 engaged with shaped first end 24 of frame 14 of heart valve prosthesis 10 and second balloon 162 abutting second end 36 of frame 14, delivery device 100" may be rotated in a direction $R_r$ relative to central longitudinal axis $LA_S$, thereby rotating shaped end 152 of first balloon 150 in direction $R_r$ such that shaped end 152 applies a rotational torque in direction $R_r$ to engaged corresponding shaped first end 34 of frame 14. This rotational torque rotates heart valve prosthesis 10 in direction $R_r$ such that torque anchoring mechanisms 22 are embedded in tissue at the desired implantation site. Stated another way, with first balloon 150 and second balloon 162 inflated, heart valve prosthesis 10 in the radially expanded configuration, and shaped end 152 of balloon 150 engaged with shaped first end 26 of heart valve prosthesis 10, delivery device 100" is rotated in direction $R_r$ to embed torque anchoring mechanisms 22 in tissue, thereby anchoring heart valve prosthesis 10 to tissue at the desired implantation site. First and second balloons 150, 162 may then be deflated and delivery device 100" may be withdrawn from the patient, leaving heart valve prosthesis 10 implanted at the desired implantation site.

FIGS. 8A-8B show the inflation lumen 192" and guidewire lumen 123 extending through the inner shaft 114, similar to the embodiment of FIGS. 6A-6B. However, instead of a single inflation lumen 192", there may be two inflation lumens; one for first balloon 150 and another for second balloon 162. Additionally, instead of multiple lumens through an inner shaft, multiple coaxial shafts with annular lumen(s) may be used, similar the embodiment of FIGS. 7A-7B. In such an embodiment, a single inflation shaft may be used with an inflation lumen between the guidewire shaft and the inflation shaft. The inflation shaft extends to the second balloon with an inflation port through the inflation shaft at the first balloon and an inflation port opening at the second balloon. Alternatively, two annular inflation shafts may be used, one terminating at the first balloon and the second terminating at the second balloon. Other arrangements of guidewire lumens and inflation lumens may be utilized as would be understood to those skilled in the art.

Figure 9A:
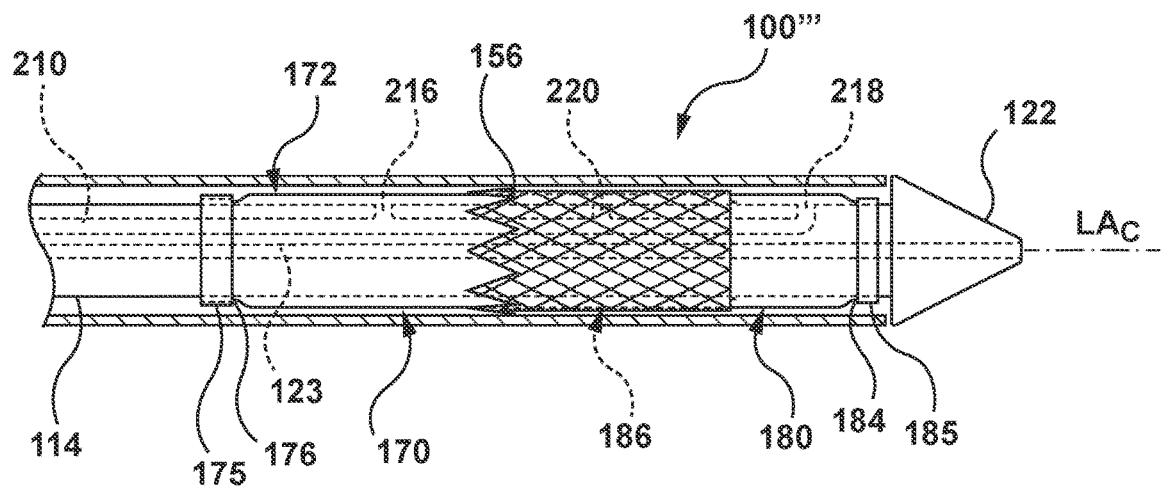
FIG. 9A is a side cutaway illustration of another embodiment of a delivery device in a delivery configuration, wherein the delivery device includes a dumbbell-shaped balloon.
Figure 9B:
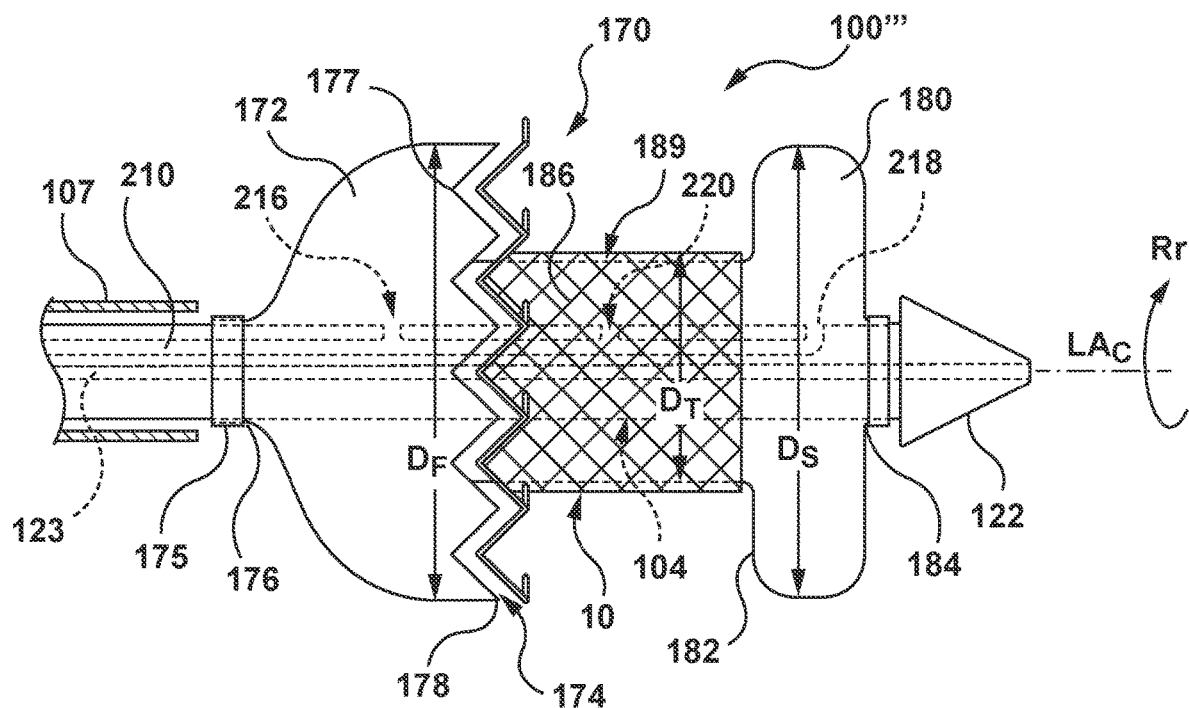
FIG. 9B is a side cutaway illustration of the delivery device of FIG. 9A with the capsule retracted and the dumbbell-shaped balloon in an inflated configuration.

FIGS. 9A-9B illustrate a distal portion of another embodiment of a delivery device 100'". Delivery device 100'" includes a dumbbell-shaped balloon 170. FIG. 9A shows delivery device 100'" with heart valve prosthesis 10 including torque anchoring mechanisms 22 disposed therein. FIG. 9A shows delivery device 100'" in a delivery configuration with dumbbell-shaped balloon 170 and heart valve prosthesis disposed within outer shaft assembly 110 with dumbbell-shaped balloon 170 uninflated and heart valve prosthesis 10 in a radially compressed configuration.

Delivery device 100'" is similar to delivery device 100 of FIGS. 2-6B except that dumbbell-shaped balloon 170 replaces balloon 150 and inflation lumen 210 of FIGS. 9A-9B is different from inflation lumen 192 of FIGS. 2-6B. Therefore, except for the differences specifically noted below, elements of delivery device 100'" are the same as or similar to the corresponding elements of FIGS. 2-6B. In particular, the proximal portion of delivery device 100'" is not described in detail and may be similar to the proximal portion of delivery device 100 described above with respect to FIGS. 2-4.

As shown in FIG. 9B, dumbbell-shaped balloon 170 includes first portion 172, a second portion 180, and a third portion 186 disposed between first portion 172 and second portion 180. A proximal end 176 of first portion 172 is attached to inner shaft 114 at a proximal bond 175 and a distal end 184 of second portion 180 is attached to inner shaft 114 at a distal bond 185, as shown in FIG. 9A. First portion 172 of balloon 170 is disposed proximal of heart valve prosthesis 10 and second portion 180 is disposed distal of heart valve prosthesis 10. Third portion 186 of dumbbell-shaped balloon 170 is disposed under heart valve prosthesis 10. In other words, heart valve prosthesis 10 is disposed on third (middle) portion 186 of dumbbell-shaped balloon 170. In the delivery configuration shown in FIG. 9A, dumbbell-shaped balloon 170 is disposed within outer shaft assembly 110. In the embodiment of FIGS. 9A-9B, dumbbell-shaped balloon 170 is a single balloon shaped to form the portions noted above and described in more detail below. However, dumbbell-shaped balloon 170 may instead be three separate balloons. Alternatively, dumbbell-shaped balloon 170 may be a single balloon and the three portions noted above may be separate compartments of the balloon.

Inner shaft assembly 104 of FIGS. 9A-9B is similar to inner shaft assembly 104 of FIGS. 6A-6B, including an inner shaft 114 having a guidewire lumen 123 and an inflation lumen 210 extending therethrough. Inflation lumen 210 is in fluid communication with dumbbell-shaped balloon 170. In the embodiment shown in FIGS. 9A-9B, inflation lumen includes a first inflation portion 216 in fluid communication with first portion 172, a second inflation port 218 in fluid communication with second portion 180, and a third inflation portion 220 in fluid communication with opening third portion 186. However, if dumbbell-shaped balloon 170 is a single balloon with a single interior, as explained above, an inflation portion for each portion is not necessary. If each portion of dumbbell-shaped balloon 170 is a separate balloon or the portions are separate compartments, at least three inflation ports are needed, one for each balloon/compartment.

As shown in FIG. 9B, a distal end 178 of first portion 172 of dumbbell-shaped balloon 170 is a shaped end 174 shaped to engage first end 34 of frame 14 of heart valve prosthesis 10. In an embodiment, shaped end 174 includes a plurality of peaks 175 extending distally and a plurality of valleys 177 extending proximally. Peaks 175 and valleys 177 are spaced radially from the central longitudinal axis LAc. Peaks 175 and valleys 177 are arranged opposite of peaks 18 and valleys 20 of first end 34 of frame 14. Dumbbell-shaped balloon 170 is in an uninflated configuration and disposed within outer shaft assembly 110 for delivery, as shown in FIG. 9A, and is inflated to an inflated configuration to engage and rotate frame 14, as shown in FIG. 9B. Dumbbell-shaped balloon 170 may be a compliant high friction balloon constructed of any suitable material, such as, but not limited to, polyethylene terephthalate (PET), nylon, or polyurethane.

FIG. 9B shows dumbbell-shaped balloon 170 in the inflated configuration. First portion 172 of dumbbell shaped balloon 170 has a first expanded diameter $D_f$ in the inflated configuration. Second portion 180 of dumbbell-shaped balloon 170 has a second expanded diameter $D_s$ in the inflated configuration. A proximal end 182 of second portion 180 is configured such that proximal end 182 abuts second end 32 of heart valve prosthesis 10. Second portion 180 is configured to provide longitudinal stability for heart valve prosthesis 10 along central longitudinal axis $LA_c$ relative to delivery device 100''' as heart valve prosthesis 10 is rotated and torque anchoring mechanisms 22 are embedded in tissue at desired implantation site. Stated another way, when second portion 180 of dumbbell-shaped balloon 170 is in the inflated configuration, second portion 180 is configured to prevent shaped end 26 of heart valve prosthesis 10 from disengaging from shaped end 174 of first portion 172 of dumbbell-shaped balloon 170. Third portion 186 of dumbbell-shaped balloon 170 has a third expanded diameter $D_t$ when in the inflated configuration. Third portion 186 is configured such that when third portion 186 is in the inflated configuration, an outer surface 189 of third portion 186 engages an inner surface of heart valve prosthesis 10. Stated another way, when third portion 186 of dumbbell-shaped balloon 170 is in the inflated configuration, third portion 186 provides radial force outward from central longitudinal axis $LA_c$, supporting frame 14 of heart valve prosthesis 10. When first, second, and third portions 172, 180, and 186 are each in the inflated configuration, third expanded diameter $D_t$ is smaller than both first expanded diameter $D_f$ and second expanded diameter $D_s$.

With the above understanding of components in mind, operation and interaction of components of the present disclosure may be explained herein. As shown in FIG. 9A, heart valve prosthesis 10 is disposed in a radially compressed configuration within capsule 107 of outer shaft assembly 110. Dumbbell shaped balloon 170 is uninflated. In other embodiments, and particularly with third portion 186 of dumbbell-shaped balloon 170 engaging an inner surface of heart valve prosthesis 10, capsule 107 may be excluded. In particular, heart valve prosthesis 10 may be balloon-expandable. Delivery device 100''' is delivered to an implantation site, such as the site of a native mitral valve. When at the implantation site, outer shaft assembly 110 is retracted proximally, thereby retracting capsule 107 proximally. Capsule 107 is retracted proximally sufficient to expose heart valve prosthesis 10. In the embodiment shown, heart valve prosthesis 10 is self-expanding. Therefore, retraction of capsule 107 enables heart valve prosthesis 10 to self-expand to the radially expanded configuration. Capsule 107 may be retracted further proximally, or may have been retracted further initially, such that first portion 172 of dumbbell shaped balloon 170 is not covered by capsule 107. An inflation fluid, such as but not limited to saline, is injected through inflation lumen 210, out of inflation ports 216, 218, and 220, and into the interiors of first, second, and third portions 172, 180, and 186 of dumbbell-shaped balloon 170, thereby inflating dumbbell-shaped balloon 170, as shown in FIG. 9B. In other embodiments, heart valve prosthesis 10 may be balloon-expandable and capsule 107 may be eliminated. When such a delivery device is at the implantation site, dumbbell-shaped balloon 170 is inflated, thereby expanding heart valve prosthesis 10. Shaped end 174 of first portion 172 of dumbbell-shaped balloon 170 is aligned with the shaped first end 34 of frame 14 of heart valve prosthesis 10. In an embodiment, peaks 175 of first portion 172 of dumbbell-shaped balloon 170 engage corresponding valleys 20 of heart valve prosthesis 10, and valleys 177 of dumbbell-shaped balloon 170 engage corresponding peaks 18 of heart valve prosthesis 10. Also, proximal end 182 of second portion 180 of dumbbell-shaped balloon 170 abuts second end 34 of heart valve prosthesis 10. In an embodiment, heart valve prosthesis 10 may be compressively held between first portion 172 and third portion 186 of balloon 170 when balloon 170 is in the second (inflated) configuration.

With shaped end 174 of first portion 172 of dumbbell shaped balloon 170 engaged with shaped first end 24 of frame 14 of heart valve prosthesis 10 and second portion 180 of dumbbell shaped balloon 170 abutting second end 36 of frame 14, delivery device 100''' may be rotated in a direction $R_r$ relative to central longitudinal axis $LA_c$, thereby rotating dumbbell-shaped balloon 170 in direction $R_r$ such that shaped end 174 applies a rotational torque in direction $R_r$ to engaged corresponding shaped first end 34 of frame 14. This rotational torque rotates heart valve prosthesis 10 in direction $R_r$ such that torque anchoring mechanisms 22 are embedded in tissue at the desired implantation site. Stated another way, with dumbbell shaped balloon 170 inflated, heart valve prosthesis 10 in the radially expanded configuration, and shaped end 174 of first portion 172 of dumbbell shaped balloon 170 engaged with shaped first end 26 of heart valve prosthesis 10, delivery device 100''' is rotated in direction $R_r$ to embed torque anchoring mechanisms 22 in tissue, thereby anchoring heart valve prosthesis 10 to tissue at the desired implantation site. Dumbbell-shaped balloon 170 may then be deflated and delivery device 100''' may be withdrawn from the patient, leaving heart valve prosthesis 10 implanted at the desired implantation site.

Figure 10A:
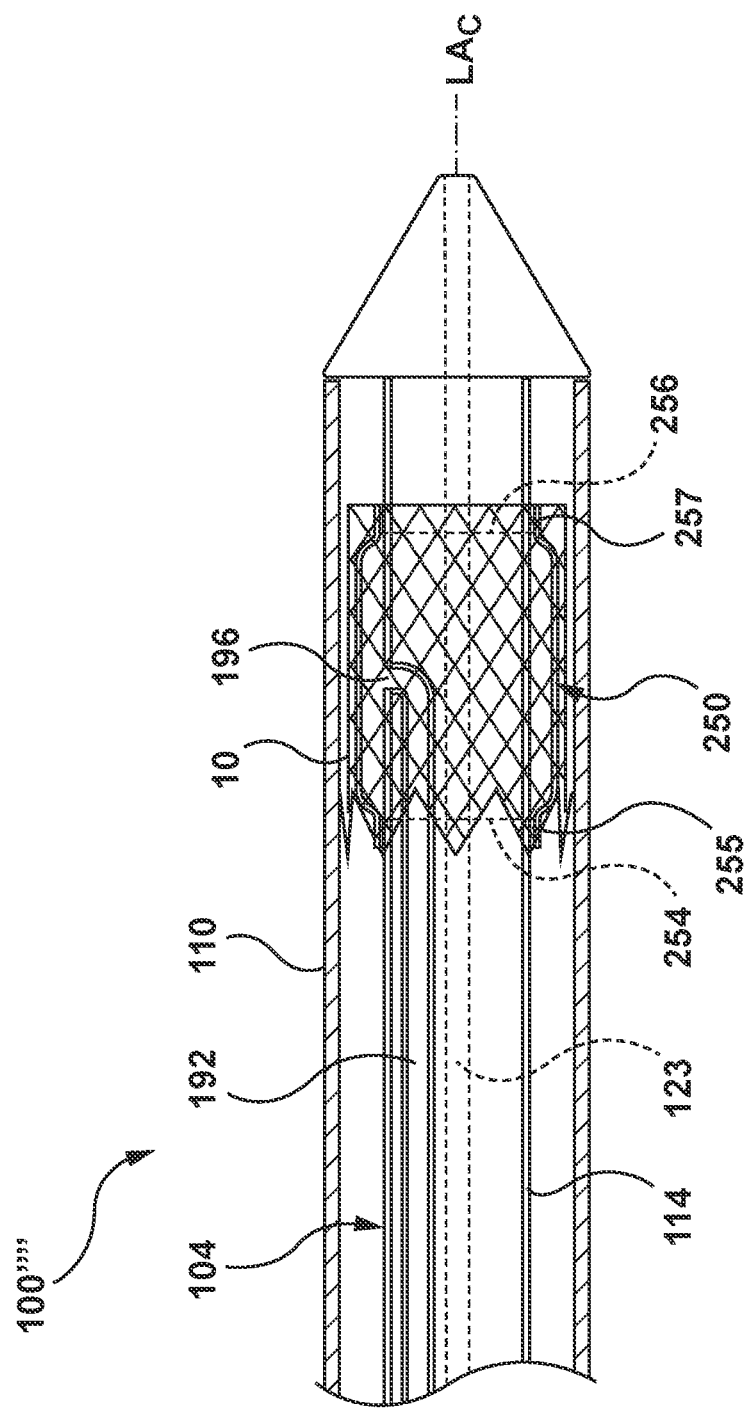
FIG. 10A is a side cutaway illustration of another embodiment of a delivery device in a delivery configuration, wherein the delivery device includes a balloon.

FIGS. 10A-10C illustrate a distal portion of another embodiment of a delivery device 100''''. Delivery device 100'''' includes a balloon 250. FIG. 10A shows delivery device 100'''' with heart valve prosthesis 10 including torque anchoring mechanisms 22 (FIG. 10B) disposed therein. FIG. 10A shows delivery device 100'''' in a delivery configuration with balloon 250 and heart valve prosthesis 10 disposed within outer shaft assembly 110. Balloon 250 is uninflated and heart valve prosthesis 10 is in a radially compressed configuration.

Delivery device 100'''' is similar to delivery device 100 of FIGS. 2-6B except that balloon 250 replaces balloon 150 and is disposed within heart valve prosthesis 10. Therefore, except for the differences specifically noted below, elements of delivery device 100'''' are the same as or similar to the corresponding elements of FIGS. 2-6B. In particular, the proximal portion of delivery device 100'''' is not described in detail and may be similar to the proximal portion of delivery device 100 described above with respect to FIGS. 2-4.

As shown in FIG. 10A, a proximal end 254 of balloon 250 is attached to inner shaft 114 at a proximal bond 255 and a distal end 256 is attached to inner shaft 114 at a distal bond 257. Balloon 250 is disposed under (within) heart valve prosthesis 10. In other words, heart valve prosthesis 10 is disposed on balloon 250. In the delivery configuration shown in FIG. 10A, balloon 250 is thus disposed within outer shaft assembly 110.

Inner shaft assembly 104 of FIGS. 10A-10B is similar to inner shaft assembly 104 of FIGS. 6A-6B, including an inner shaft 114 having a guidewire lumen 123 and an inflation lumen 192 extending therethrough. Inflation lumen 192 is in fluid communication with balloon 250. In the embodiment shown in FIGS. 10A-10B, inflation lumen 192 includes an inflation port 196 in fluid communication with balloon 250.

As shown in FIG. 10B and in greater detail in FIG. 10C, an outer surface 253 of balloon 250 includes a shaped portion 252. In an embodiment, shaped portion 252 is configured to extend into open spaces 17 and engage frame 14 of heart valve prosthesis 10 when balloon 250 is inflated. In an embodiment, shaped portion 252 includes a plurality of protrusions 258 extending radially outward from the outer surface 253 of balloon 250. Heart valve prosthesis 10 is loaded onto balloon 250 such that protrusions 258 are arranged opposite of corresponding open spaces 17 of frame 14. Balloon 250 is in an uninflated configuration and disposed within outer shaft assembly 110 for delivery, as shown in FIG. 10A, and is inflated to an inflated configuration such that each protrusion 258 extends radially through corresponding open space 17. When in the inflated configuration, an outer surface of each protrusion 258 engages adjacent struts 16 such that rotation of balloon 250 engages and rotates frame 14, as shown in FIG. 10B. Balloon 250 may be a compliant high friction balloon constructed of any suitable material, such as, but not limited to, polyethylene terephthalate (PET), nylon, or polyurethane.

FIG. 10B shows balloon 250 in the inflated configuration. Balloon 250 is further configured such that when balloon 250 is in the inflated configuration, the outer surface 253 of balloon 250 engages an inner surface of heart valve prosthesis 10. Thus, when balloon 250 is in the inflated configuration, balloon 250 provides radial force outward from central longitudinal axis $LA_c$, supporting frame 14 of heart valve prosthesis 10 and is configured to engage and rotate frame 14.

With the above understanding of components in mind, operation and interaction of components of the present disclosure may be explained herein. As shown in FIG. 10A, heart valve prosthesis 10 is disposed in the radially compressed configuration within capsule 107 of outer shaft assembly 110. Balloon 250 is in the uninflated configuration and is disposed within heart valve prosthesis 10. In other embodiments, as explained above, capsule 107 may be excluded. Delivery device 100''' is delivered to an implantation site, such as the site of a native mitral valve. When at the implantation site, outer shaft assembly 110 is retracted proximally, thereby retracting capsule 107 proximally. Capsule 107 is retracted proximally sufficient to expose heart valve prosthesis 10 and balloon 250 therein. In the embodiment shown, heart valve prosthesis 10 is self-expanding. Therefore, retraction of capsule 107 enables heart valve prosthesis 10 to self-expand to the radially expanded configuration. An inflation fluid, such as but not limited to saline, is injected through inflation lumen 192, out of inflation port 196 and into the interior of balloon 250, thereby inflating balloon 250 (transitioning from the uninflated to the inflated configuration), as shown in FIG. 10B. In other embodiments, heart valve prosthesis 10 may be balloon-expandable and capsule 107 may be eliminated. When such a delivery device is at the implantation site, balloon 250 is inflated, thereby expanding heart valve prosthesis 10. Protrusions 258 of shaped portion 252 of balloon 250 are aligned with open spaces 17 between adjacent struts 16 of frame 14 of heart valve prosthesis 10.

With shaped portion 252 of balloon 250 engaged with open spaces 17 and struts 16 of frame 14 of heart valve prosthesis 10, delivery device 100'''' may be rotated in a direction $R_r$ relative to central longitudinal axis $LA_c$, thereby rotating balloon 250 in direction $R_r$ such that shaped portion 252 applies a rotational torque in direction $R_r$ to engaged corresponding frame 14. This rotational torque rotates heart valve prosthesis 10 in direction $R_r$ such that torque anchoring mechanisms 22 are embedded in tissue at the desired implantation site. Stated another way, with balloon 250 inflated, heart valve prosthesis 10 in the radially expanded configuration, and shaped portion 252 of balloon 250 engaged with frame 14 of heart valve prosthesis 10, delivery device 100'''' is rotated in direction $R_r$ to embed torque anchoring mechanisms 22 in tissue, thereby anchoring heart valve prosthesis 10 to tissue at the desired implantation site. Balloon 250 may then be deflated and delivery device 100'''' may be withdrawn from the patient, leaving heart valve prosthesis 10 implanted at the desired implantation site.

Features of any of the embodiments described above may be used with any of the other embodiments described above. Further, variations in the number of balloons, inflation lumens, inflation ports, and similar items may be made within the scope of the invention. For example, and not by way of limitation, the delivery devices described above and below may also include an outer stability shaft disposed outside of the outer shaft assembly 110. Other details of the delivery devices may be as described in U.S. Pat. No. 8,414,645 to Dwork; U.S. Pat. No. 8,876,893 to Dwork; U.S. Pat. No. 8,926,692 to Dwork, each of which is incorporated in its entirety herein. Other materials than those described above may also be used within the scope of the invention.

FIGS. 11A-11D and 12A-12B illustrate another embodiment of a heart valve prosthesis 500 including a toque anchoring mechanism 530. Heart valve prosthesis 500 includes a frame 502 and a prosthetic heart valve 504 (see FIGS. 11C-11D) coupled to the frame 502. Prosthetic heart valve 504 may be any suitable prosthetic heart valve known to those skilled in the art, and may be bi-leaflet, tri-leaflet (shown) or any other suitable design. Frame 502 may include an inflow rim 510 and an outflow tube 520. Inflow rim 510 and outflow tube 520 need not be separate parts and generally may be a unitary with inflow rim 510 flaring radially outwardly from outflow tube 520. Frame 502, including inflow rim 510 and outflow tube 520 may be formed by a plurality of struts 512 with spaces or openings 513 formed there between, as known to those skilled in the art. Frame 502 is radially compressible for delivery and radially expandable for deployment at the treatment site. FIGS. 11A-11D and 12A-12B show frame 502 in a radially expanded configuration. Frame 502 may be self-expanding or balloon expandable. Frame 502 may be formed from materials such as, but not limited to, nickel titanium alloys (e.g., Nitinol), nickel-cobalt-chromium-molybdenum alloys (e.g., MP35N), stainless steel, high spring temper steel, or any other metal or other material suitable for purposes of the present disclosure.

Frame 502 defines a first or inflow end 506 and a second or outflow end 508 of heart valve prosthesis 500. Frame 502 is generally tubular and defines a central passage 524 therethrough. Prosthetic valve 504 is disposed in the central passage 504, as shown in FIGS. 11C and 11D.

Torque anchoring mechanism 530 of heart valve prosthesis 500 includes a ring 532 with a plurality of barbs 534 extending radially outwardly from the ring 532, as shown in FIGS. 11A-11D and 12A-12B. In the embodiment shown, ring 532 is disposed over (around) outflow tube 520 such that an inner surface of ring 532 circumscribes an outer surface of outflow tube 520. Ring 532 is rotatable relative to outflow tube 520 and inflow ring 510, as will be described in greater detail below. Ring 532 is also radially compressible and expandable such that ring 532 may be radially compressed for transluminal delivery and radially expandable at the treatment site for deployment. Ring 532 may be self-expanding or balloon expandable.

Each barb 534 includes distal tip 536 at an end opposite from ring 532. Distal tip 536 may be a sharp tip to assist in engagement with tissue. Each barb 534 may be formed separately from ring 532 and attached thereto, or may be formed unitarily with ring 532. Barbs 534 are shown extending directly radially outwardly from ring 532 in FIGS. 11A-11D and 12A. However, in the embodiment shown, barbs 534 are angled, as shown in FIG. 12B. In particular, each barb 534 includes a first portion 535 extending directly radially outward from ring 532, a bend 533, and a second portion 537 extending at an angle α with respect to the radial direction Rd extending through the first portion of the same barb 534, as shown in FIG. 12B. Angle α may be 10-90 degrees. In the embodiment shown, barbs 534 are pre-set to the bent shape shown in FIG. 12B and are held in the radially outward direction shown in FIGS. 11A-11O and 12A by an outside force, described below. Thus, upon removal of the outside force, barbs 534 return to the pre-set bent shape shown in FIG. 12B. Although FIG. 12B shows a particular shape for barbs 534, it is not limiting. Other shapes, angles, and bends may be used in keeping with the present disclosure. In order for barbs 534 to have a pre-set bend, they may be formed of a shape memory material, including, but not limited to, nickel-titanium alloys (e.g. Nitinol), nickel-cobalt-chromium-molybdenum alloys (e.g., MP35N), stainless steel, high spring temper steel, or any other metal or other material suitable for purposes of the present disclosure.

Figure 11A:
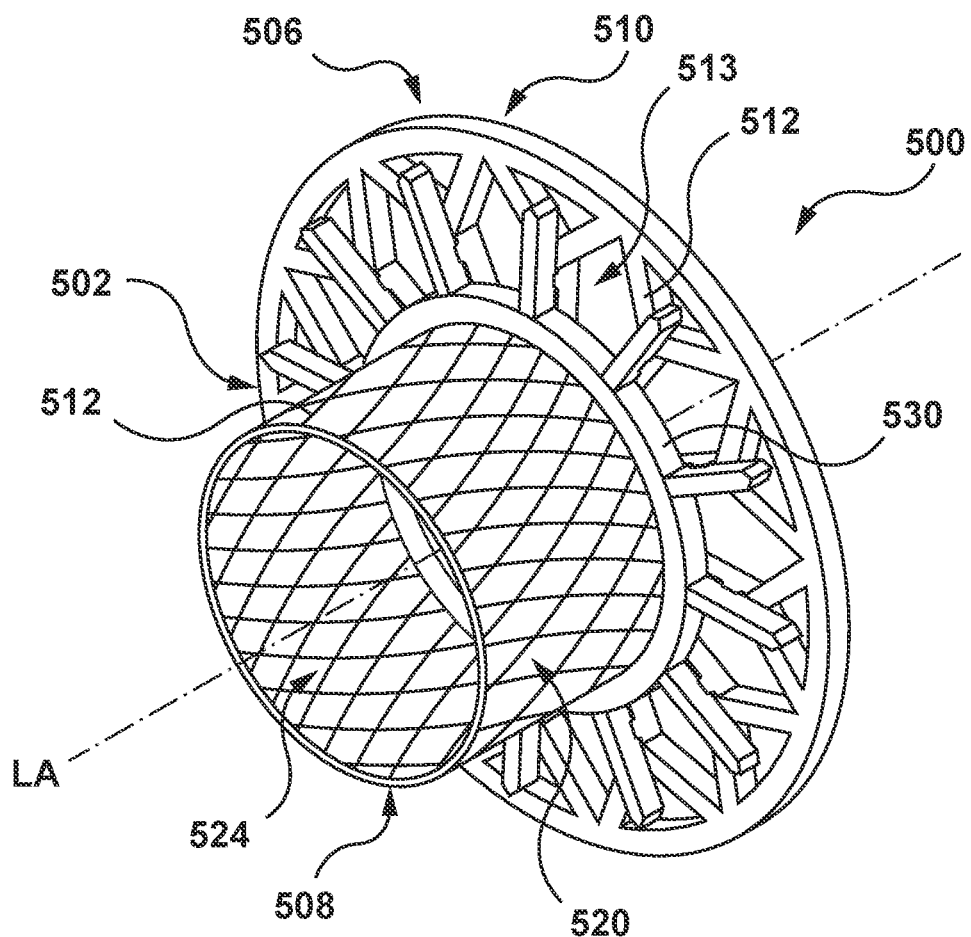
Figure 11C:
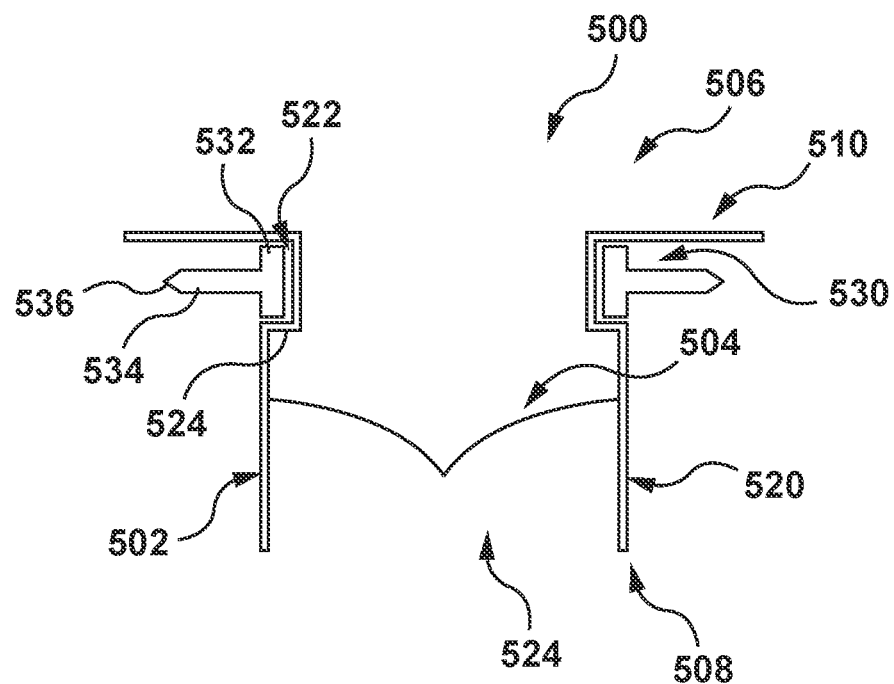
Figure 11D:
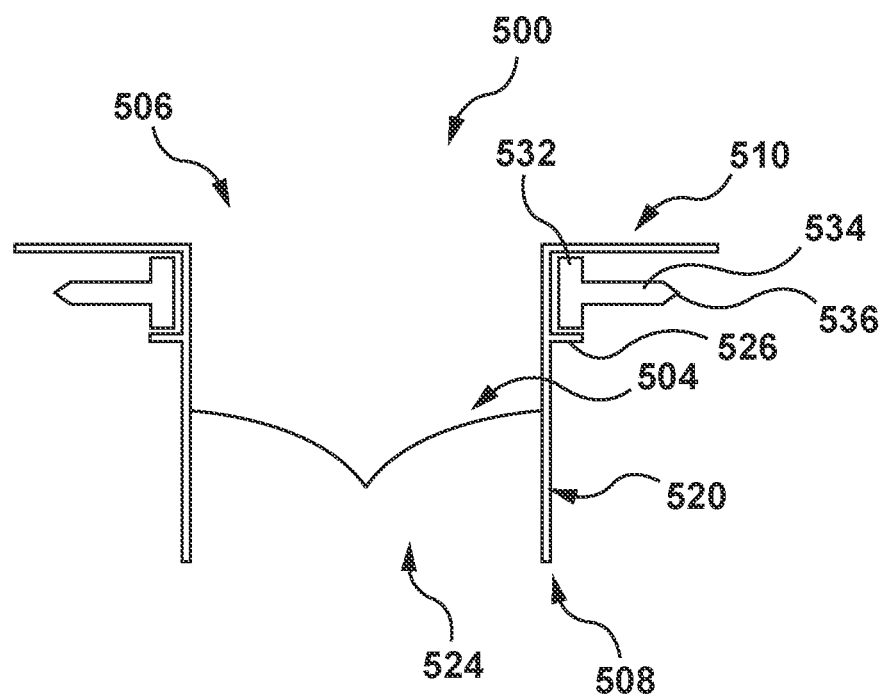

As shown in FIGS. 11A-11D and 12A, barbs 534 may be restrained in a straight, directly radially outward direction for delivery and pre-deployment. In particular, as shown in FIG. 11B, certain struts 512 of inflow portion 510 may each include lips 514 that restrain a barb 534 in the radially outward configuration. Lips 514 may be constructed as an extension of the respective strut 512 of the inflow portion. Lips 514 may extend in a direction generally parallel to the longitudinal axis LA of the heart valve prosthesis 500, which is generally perpendicular to the longitudinal axis of the respective barb 534 when in the restrained, generally radially outward direction. Lips 514 may instead be constructed as a groove in the respective strut 512 such that barb 534 at least partially sits in the groove, thereby restraining barb 534 from returning to its pre-set bent configuration. Lips 514 also prevent ring 532 from rotating around central longitudinal axis LA until a force is applied to overcome the restraining force of lips 514, thereby rotating ring 532 and enabling barbs 534 to return to their pre-set bent configuration, as explained in more detail below.

Ring 532 may also be restrained from moving longitudinally along outflow portion 520. Ring 532 may be restrained by lips, grooves, or any other way to prevent ring 532 from sliding longitudinally along outflow portion 520 while still enabling ring 532 to rotate about central longitudinal axis LA. In one non-limiting embodiment shown in FIG. 11C, a groove 522 is provided circumferentially around a portion of outflow tube 520. Ring 532 is disposed in groove 522 such ring 532 is disposed between a shoulder 524 that prevents longitudinal movement towards second (outflow) end 508 and inflow ring 510 that prevents longitudinal movement toward first (inflow) end 506. In another non-limiting example shown in FIG. 11D, a lip 526 may extend radially outward from outflow portion 520 distal of ring 532. Thus, ring 532 is disposed between lip 526 and inflow ring 510 such that lip 526 prevents longitudinal movement of ring 532 in a distal (outflow) direction and inflow portion 510 prevents longitudinal movement of ring 532 in a proximal (inflow) direction. Lip 526 may be a continuous lip disposed around the circumference of outflow portion 520, or a plurality of lips 526 may be disposed intermittently (i.e., spaced from each other) around the circumference of outflow portion 520.

Torque anchoring mechanism 530 is configured such that a delivery device (an example of which is described below) may interact with torque anchoring mechanism 530 to rotate ring 532 such that barbs 534 may embed in tissue at the desired implantation site. In the embodiment shown in FIGS. 11A-11D and 12A-12B, ring 532 of torque anchoring mechanism 530 includes a plurality of connection points 538 for a delivery system. In an embodiment, connections points 538 are openings disposed through ring 532 for tethers or rods of a delivery system to connect with, as described in more detail below. In the embodiment shown in FIGS. 12A-12B, three (3) connection points 538 are shown. However, more or fewer connection points 538 may be utilized provided that the delivery system is configured to rotate ring 532 to overcome the restraining force of lips 514.

Figure 12A:
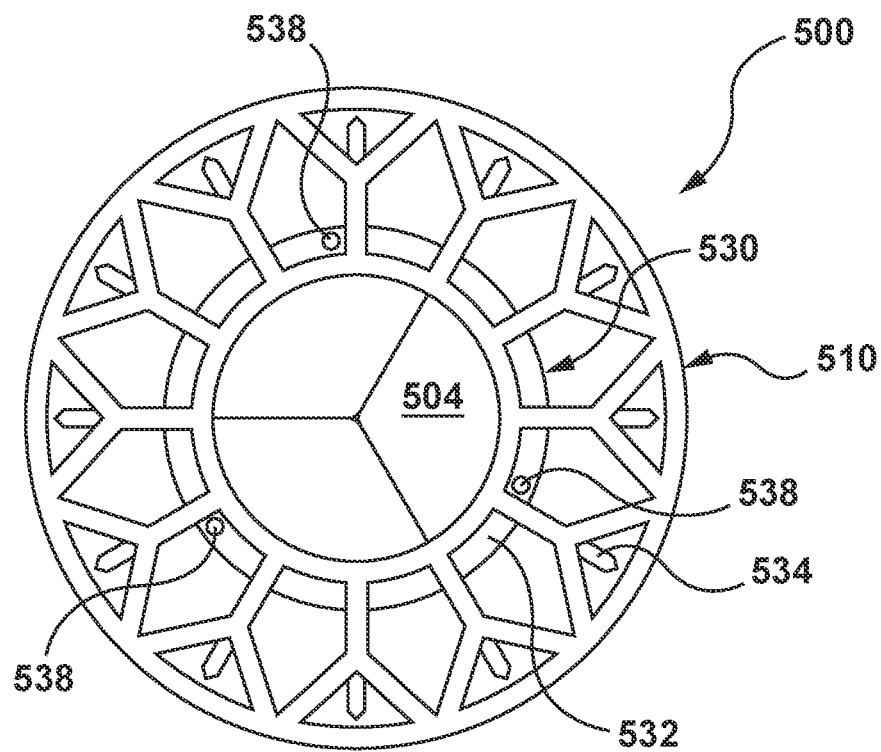
FIGS. 12A-12B are end views of the heart valve prosthesis of FIGS. 10A-10C in a pre-deployment configuration and a deployed configuration.
Figure 12B:
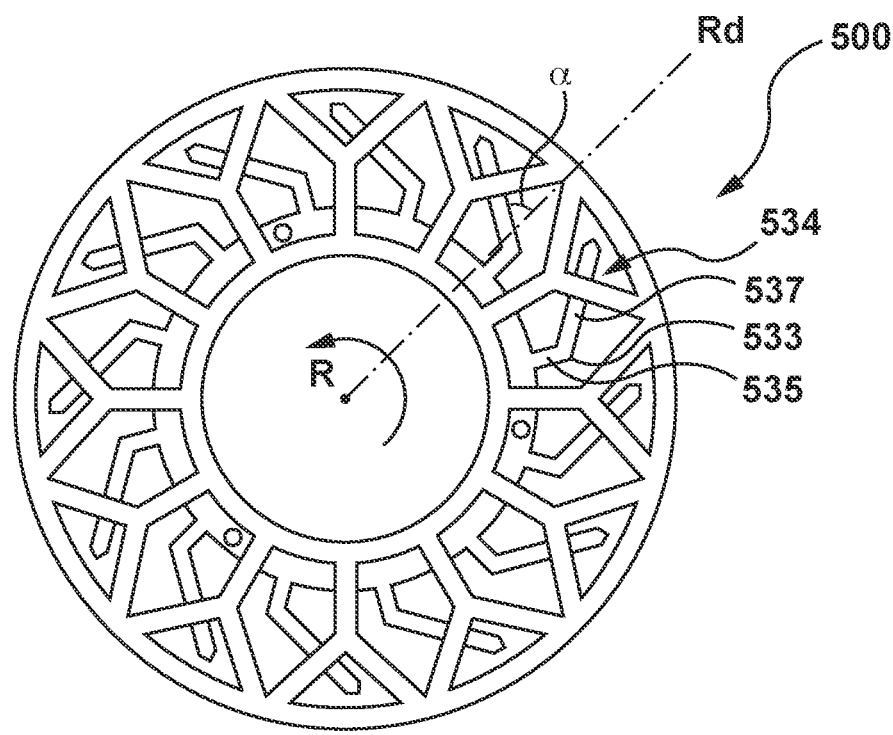

With the above of the components of heart valve prosthesis 500 in mind, delivery and deployment of heart valve prosthesis 500 is explained. Heart valve prosthesis 500 is compressed into the radially compressed configuration for delivery. In the radially compressed configuration, outflow tube 520 is radially compressed. Inflow portion 510 and torque anchor mechanism 530 may be rotated such that they extend longitudinally away from outflow portion 520 and may be radially compressed. Heart valve prosthesis 500 is delivered to the treatment site such as a native mitral valve in a delivery device in the radially compressed configuration. When at the treatment site, a capsule or sheath of the delivery device may be retracted, thereby enabling heart valve prosthesis 500 to self-expand to the radially expanded configuration shown in FIGS. 11A and 12A. As can be seen in FIGS. 11A and 12A, barbs 534 extend radially outward. The delivery system remains coupled to heart valve prosthesis 500, such as through tethers described below interacting with connection points 538 of ring 532. With heart valve prosthesis 500 at the desired location and in the radially expanded configuration, the delivery device or a portion thereof is rotated such that the portion of the delivery device connected to ring 532 is rotated, thereby rotating ring 532. This rotation overcomes the retraining force of lips 514. With barbs 534 no longer restrained by lips 514, barbs 534 revert back to their pre-set bent configuration, as shown in FIG. 12B. Also, due to rotation of ring 532, the now angled barbs 534 embed into tissue at the implantation site, thereby anchoring heart valve prosthesis 500 at the implantation site.

Figure 12C:
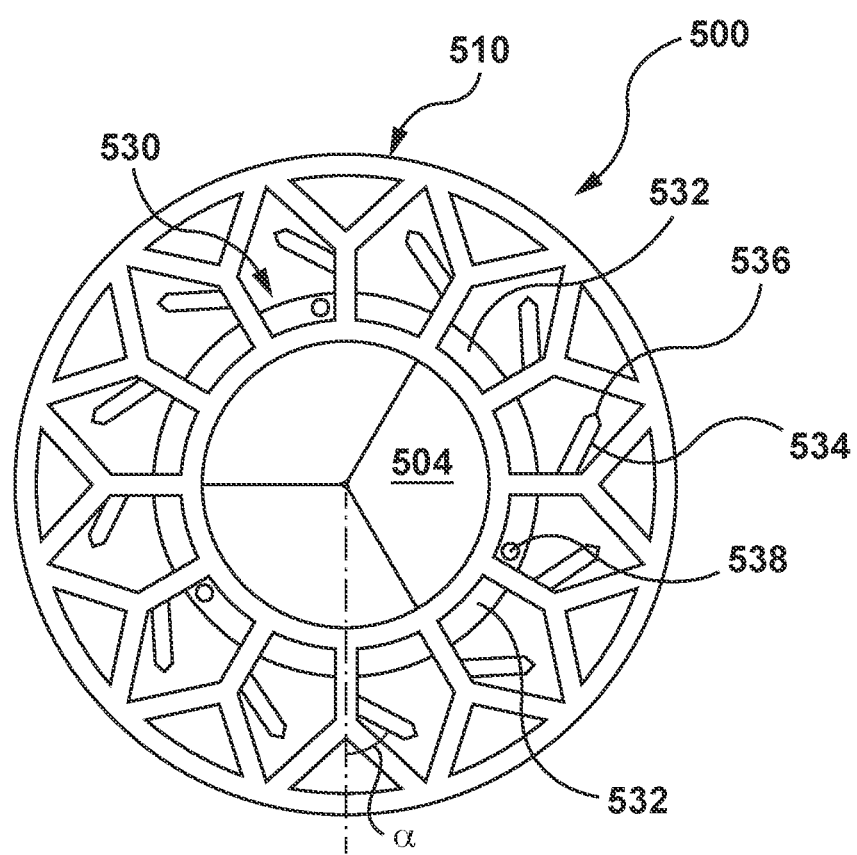
FIG. 12C is an end view of an alternative embodiment of the heart valve prosthesis of FIGS. 11A-11C.

Although a specific embodiment of heart valve prosthesis 500 has been disclosed, variations may be made in keeping with the present disclosure. For example, and not by way of limitation, barbs 534 need not be straightened by lips 514 and then returned to their pre-set bent configuration. Instead, barbs 534 may be curved or bent prior to rotation of ring 532. In such an embodiment, lips 514 may be eliminated or may still be used to keep ring 534 from rotating during delivery and initial deployment of heart valve prosthesis 500. In such an embodiment, when heart valve prosthesis is initially deployed from the delivery system, heart valve prosthesis 500 radially expands as shown in FIG. 12C. As can be seen, barbs 534 are already curved or bent. However, as described above, each barb 534 may be held in place by lips 514. Thus, a portion of each barb 534 in FIG. 12C is hidden by the corresponding strut 512. As explained above, the delivery system remains coupled to heart valve prosthesis 500 of FIG. 12C, such as through tethers described below interacting with connection points 538 of ring 532. With heart valve prosthesis 500 at the desired location and in the radially expanded configuration, the delivery device or a portion thereof is rotated such that the portion of the delivery device connected to ring 532 is rotated, thereby rotating ring 532. This rotation overcomes the retraining force of lips 514. Thus, ring 532 rotates and angled barbs 534 embed into tissue at the implantation site, thereby anchoring heart valve prosthesis 500 at the implantation site.

Other variations to heart valve prosthesis 500 may be utilized. For example, and not by way of limitation, clips or arms at second (outflow) end 208 may be utilized for heart valve prosthesis 500 to engage native leaflets of the native valve. Further, elements of the other embodiments described above and below may be utilized with heart valve prosthesis 500.

Figure 13:
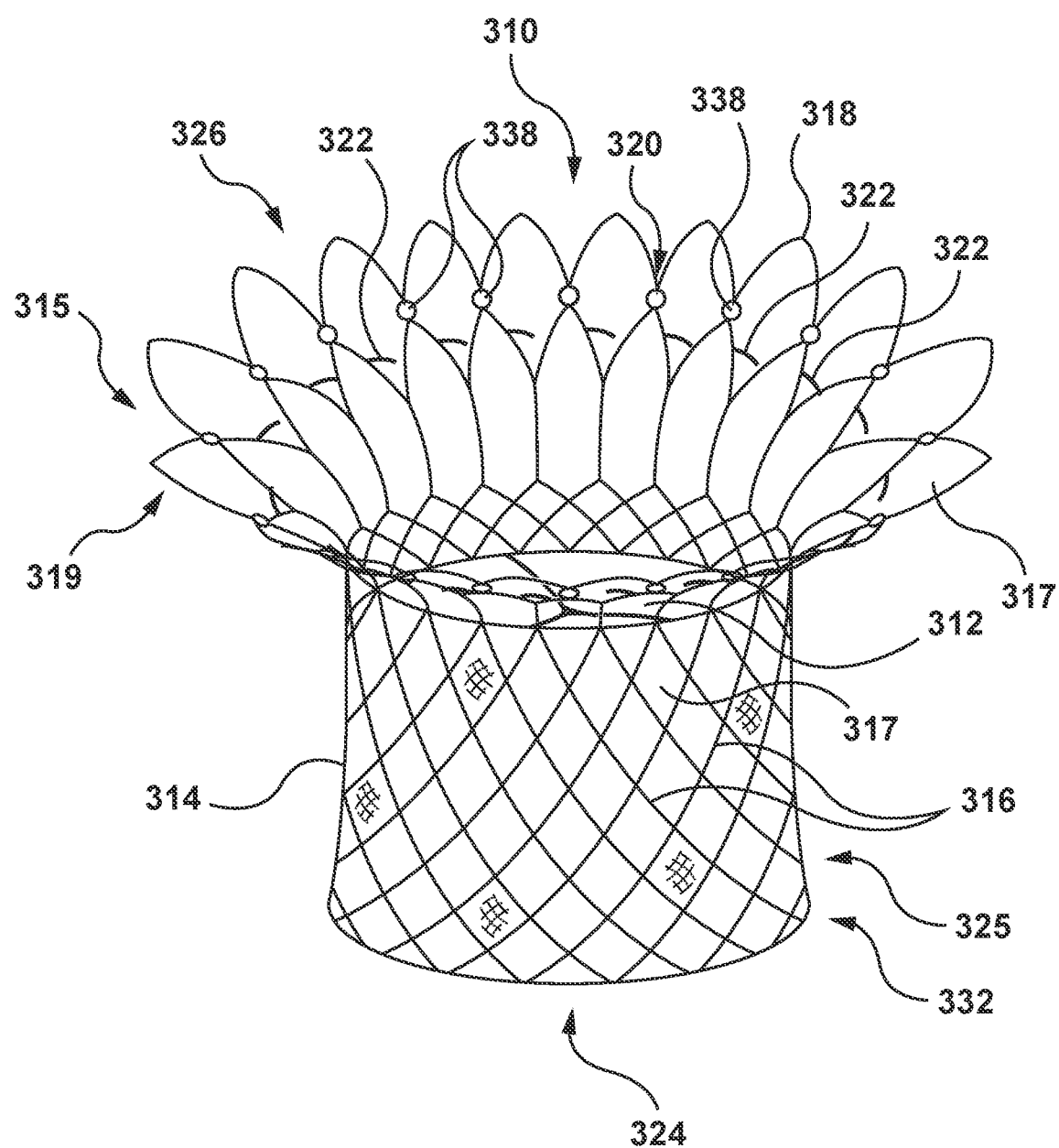
FIG. 13 is a perspective illustration of a heart valve prosthesis with a torque anchoring mechanism according to another embodiment hereof.

FIG. 13 shows another embodiment of heart valve prosthesis 310. FIG. 13 illustrates heart valve prosthesis 310 in a radially expanded configuration. Heart valve prosthesis 310 includes a frame 314 and a prosthetic valve 312 coupled to the frame 314. Heart valve prosthesis 310 includes a radially collapsed configuration and the radially expanded configuration. Heart valve prosthesis 310 also includes a first end 326 and a second end 332 opposite first end 326. Frame 314 is generally tubular and defines a central passage 324, and includes a first end 334 and a second end 336. In the embodiment shown in FIG. 13, first end 334 of frame 314 defines first end 326 of heart valve prosthesis 310. Similarly, second end 336 of frame 314 defines second end 332 of heart valve prosthesis 310. Those skilled in the art would recognize that other features, such as skirts or arms may be included as part of heart valve prosthesis 310. In the embodiment shown, first end 326 of heart valve prosthesis 310 is the proximal or inflow end, and second end 332 of heart valve prosthesis is the distal or outflow end of heart valve prosthesis 310. Also, first end 334 of frame 314 is flared radially outwardly, as shown in FIG. 13. This outward flare at first end 334 forms an inflow rim 315 that is configured to contact an atrial side of a native mitral valve annulus. Further, although inflow rim 315 is shown as generally circular, inflow rim may be other shapes to conform to the anatomy adjacent the native mitral valve, such as but not limited D-shaped. A portion of frame 314 may also be described as an outflow portion 325. Outflow portion 325 is generally tubular and is configured to extend through the leaflets of the native valve complex. Although heart valve prosthesis 310 as shown is configured for placement at the site of a native mitral valve, heart valve prosthesis 310 may be used at other implantation sites, such as, but not limited to, other the sites of native heart valves.

Frame 314 is a support structure that comprises struts 316 arranged relative to each other with a plurality of open spaces 317 therebetween. Frame 314 provides a desired compressibility and expansion force against a native annulus at the desired implantation site. Frame 314 also provides support for prosthetic valve 312. Prosthetic valve 312 is coupled to and disposed within frame 314. Although the embodiment of FIG. 13 does not show the radially outward portion of inflow rim 315 bent to extend longitudinally as in FIG. 1, this is not limiting and heart valve prosthesis 310 of FIG. 13 may include such a bend. Struts 316 of inflow rim 315 form a plurality of peaks 318 and valleys 320 at a first end of inflow rim 315.

A plurality of torque anchoring mechanisms 322 are coupled to inflow rim 315. Torque anchoring mechanisms 322 are configured such that when heart valve prosthesis 310 is in the radially expanded configuration at a desired implantation site, and at least a portion of heart valve prosthesis 310 is rotated, torque anchoring mechanisms 322 are embedded into tissue at the desired implantation site. As shown in FIG. 13, torque anchoring mechanisms 322 extend clockwise. However, they may extend counter-clockwise or partially angled in either direction. Further, torque anchoring mechanisms 322 may generally extend from an underside 319 of inflow rim 315. The underside 319 of inflow rim 315 is the surface facing the native mitral valve annulus when the heart valve prosthesis 310 is deployed with inflow rim 315 on the atrial side of the native mitral valve annulus (i.e., the surface of the inflow rim facing the outflow end). Torque anchoring mechanisms 322 may be barbs, clips, hooks, arrows or similar devices configured to embed into tissue at the desired implantation site. While FIG. 13 shows each torque anchoring mechanism 322 as single wire, this is not limiting and other configurations of torque anchoring mechanisms may be used.

Frame 314 may be formed, for example, and not by way of limitation, of nickel titanium, Nitinol, nickel-cobalt-chromium-molybdenum (MP35N), stainless steel, high spring temper steel, or any other metal or suitable for purposes of the present disclosure. Torque anchoring mechanisms 322 may be formed from the same types of materials as frame 314. Torque anchoring mechanisms 322 may be extensions of struts 316, or may be coupled to frame 314, for example, and not by way of limitation, by fusing, welding, adhesive, sutures, or other means suitable for the purposed described herein.

Frame 314 shown in FIG. 13 further includes a plurality of tether connection points 338. In the embodiment shown, tether connection points 338 are shown at valleys 320, but they may be located elsewhere on inflow rim 315. In the embodiment shown, tether connections points 338 are openings that enable a tether of a delivery system to couple with heart valve prosthesis 310, either by direct coupling or looping through or around, to rotate heart valve prosthesis 310 or a portion thereof to embed torque anchoring mechanisms 322 into tissue at the implantation site, as described in more detail below.

Figure 14:
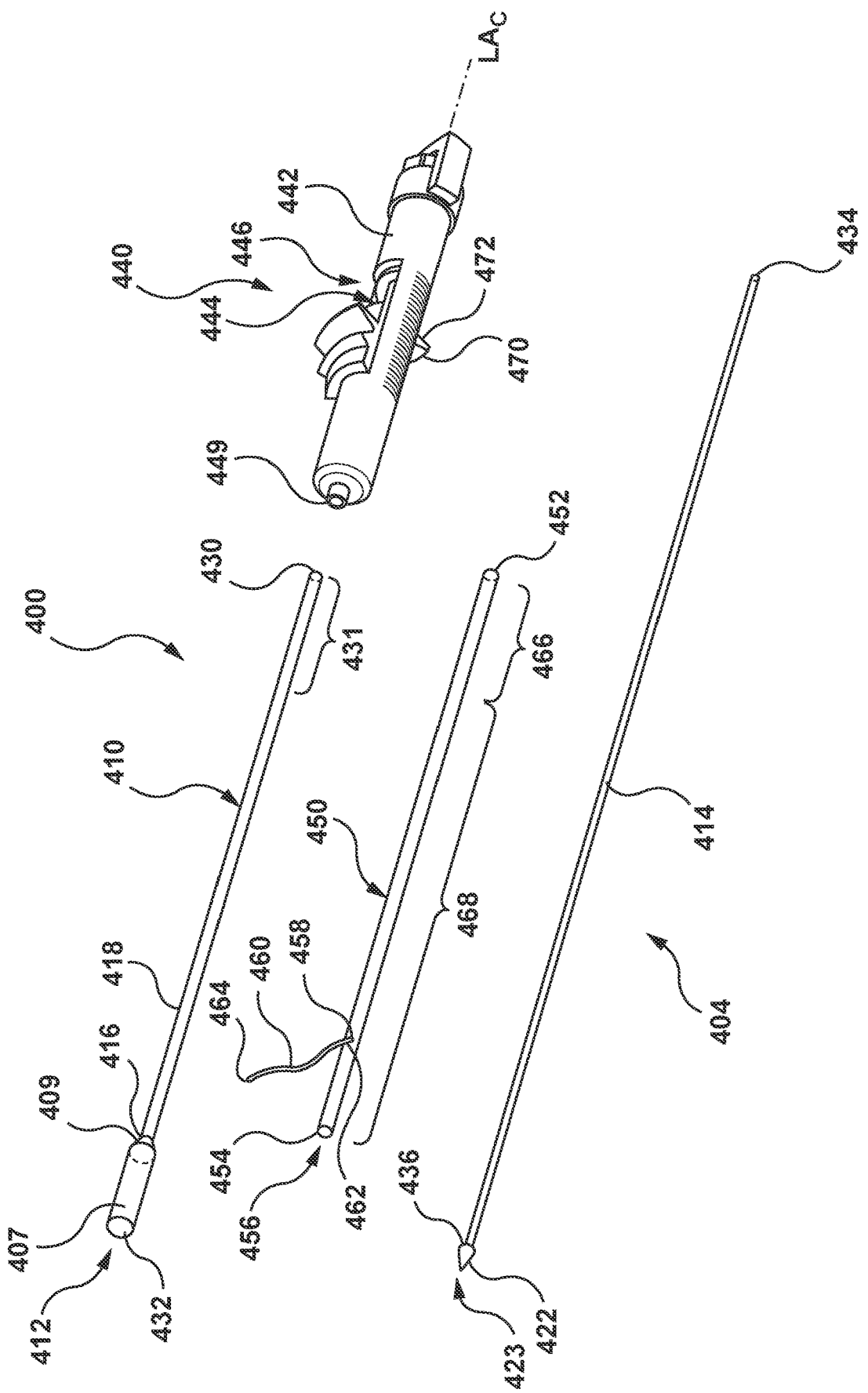
FIG. 14 is an exploded perspective illustration of an embodiment of a delivery device according to an embodiment hereof.
Figure 15:
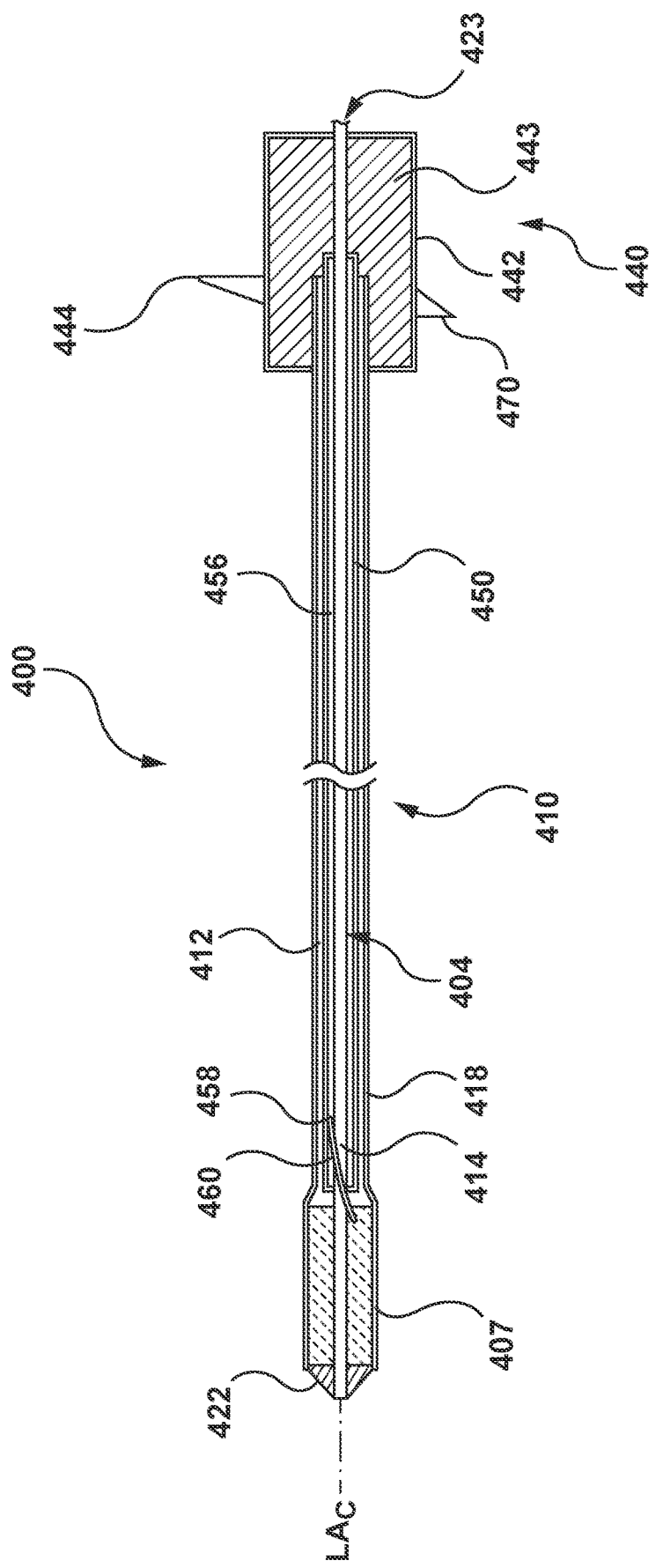
FIG. 15 is a side view illustration of the delivery device of FIG. 14.
Figure 16:
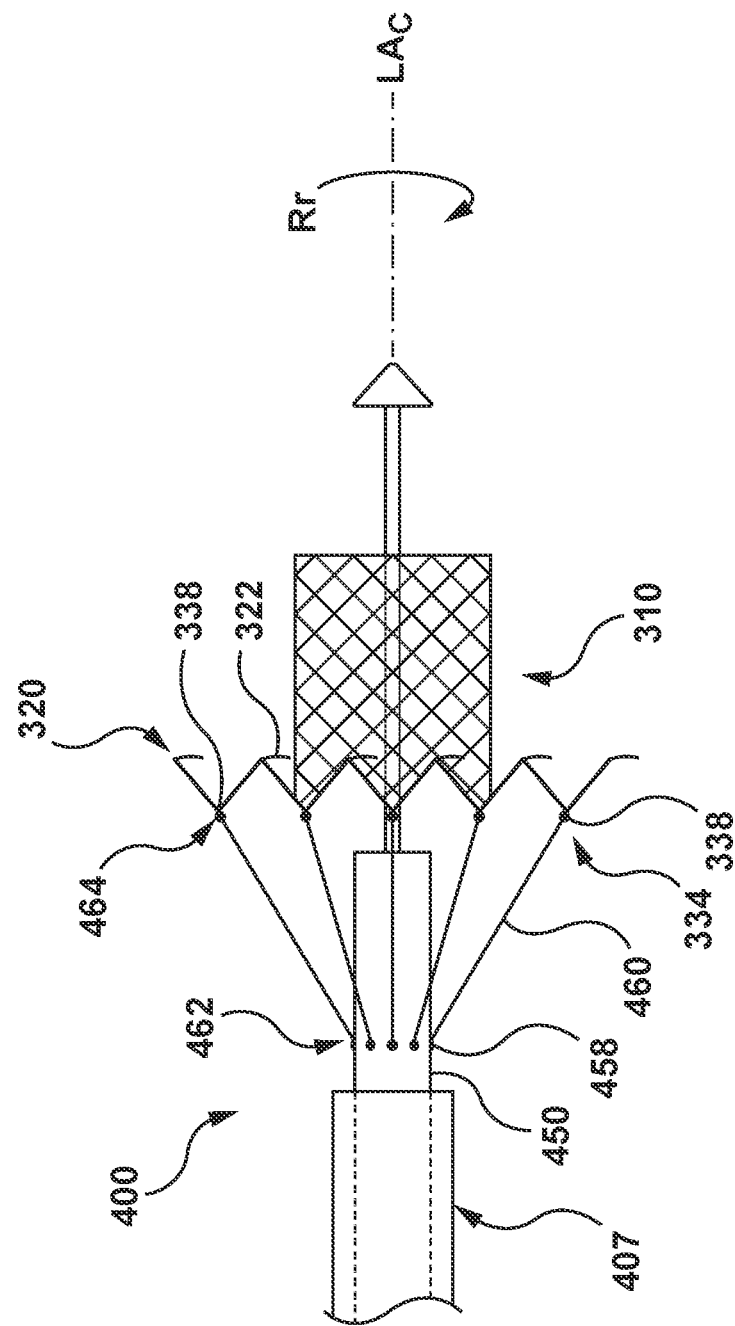
FIG. 16 is a side illustration of the delivery device of FIG. 14 and heart valve prosthesis of FIG. 13.

With the above understanding of heart valve prosthesis 310 in mind, a delivery device 400 shown in FIGS. 14-16 may be used to deliver and deploy a heart valve prosthesis such as heart valve prosthesis 310. In an embodiment, delivery device 400 generally includes a handle 440, an outer shaft assembly 410, an inner shaft assembly 404, a tether shaft 450, and a plurality of tethers 460. Delivery device 400 may be made from any suitable material, such as, but not limited to polyethylene (PE), polyethylene terephthalate (PET), and polyvinylchloride (PVC). Various features of the components of delivery device 400 reflected in FIGS. 14-16 and described below can be modified or replaced with differing structures and/or mechanisms. The components of delivery device 400 may assume different forms and construction. Therefore, the following detailed description is not meant to be limiting. Further, the systems and functions described below can be implemented in many different embodiments of hardware. Any actual hardware described is not meant to be limiting. The operation and behavior of the systems and methods presented are described with the understanding that modifications and variations of the embodiments are possible given the level of detail presented.

In an embodiment shown schematically in FIGS. 14-15, handle 440 may include a housing 442 with an actuator mechanism 444 and a rotator mechanism 470 retained therein. More particularly, handle 440 includes a cavity 443 defined by housing 442 and configured to receive portions of actuator mechanism 444 and rotator mechanism 470. In the embodiment shown in FIGS. 14-15, housing 420 forms a longitudinal slot 446 through which actuator mechanism 444 extends for interfacing by a user, and a rotational slot 472 through which rotator mechanism 470 extends for interfacing by a user. Handle 440 provides a surface for convenient handling and grasping by a user, and may have a generally cylindrical shape, as shown, or other shapes. Actuator mechanism 444 is generally constructed to provide selective retraction/advancement of outer shaft assembly 410 and can have a variety of constructions and/or devices capable of providing the desired user interface. Although shown as a slide mechanism, other constructions and/or devices may be used to retract/advance outer shaft assembly 410, such as, but to limited to rotating mechanisms, sliding mechanisms that are coaxially disposed over inner shaft assembly 404, combinations of rotating and sliding mechanisms, and other advancement/retraction mechanisms known to those skilled in the art. Similarly, rotator mechanism 470 may be any mechanism used to rotate tethers 460.

Outer shaft assembly 410 is slidably disposed over inner shaft assembly 404. With reference to FIGS. 14-15, in an embodiment, outer shaft assembly 410 includes a proximal shaft 418 and a capsule 407, and defines a lumen 412 extending from a proximal end 430 of proximal shaft 418 to a distal end 432 of capsule 407. Although outer shaft assembly 410 is described herein as including capsule 407 and proximal shaft 418, capsule 407 may simply be an extension of proximal shaft 418. Further, outer shaft assembly 410 may be referred to as a sheath or outer sheath. Proximal shaft 418 is configured for connection to capsule 407 at a connection point 416 at a proximal end 409 of capsule 407 by fusing, welding, adhesive, sutures, or other means suitable for the purposes described herein. Alternatively, proximal shaft 418 and capsule 407 may be unitary. Proximal shaft 418 extends proximally from capsule 407 and is configured for connection to handle 440. More particularly, proximal shaft 418 extends proximally into housing 442 of handle 440 and a proximal portion 431 of proximal shaft 418 is connected to actuator mechanism 444 of handle 440. Proximal portion 431 is coupled to actuator mechanism 444 such that movement of actuator mechanism 444 causes outer shaft assembly 410 to move relative inner shaft assembly 404. Proximal shaft 418 may be coupled to actuator mechanism 444, for example, and not by way of limitation, by adhesives, welding, clamping, and other coupling devices as appropriate. Outer shaft assembly 410 is thus movable relative to handle 440 and inner shaft assembly 404 by actuator mechanism 444. However, if actuator mechanism 444 is not moved and handle 440 is moved, outer shaft assembly 410 moves with handle 440, not relative to handle 440.

Inner shaft assembly 404 is similar to inner shaft assembly 104 previously described. Inner shaft assembly 404 extends within a lumen 456 of tether shaft 450, described in greater detail below and as shown in FIGS. 14-15. Inner shaft assembly 404 includes an inner shaft 414 and a distal tip 422. Inner shaft 414 extends from a proximal end 434 of inner shaft 414 to a distal end 436 of inner shaft 414. Distal end 436 of inner shaft 414 is attached to distal tip 422. The components of inner shaft assembly 404 combine to define continuous guidewire lumen 423, which is sized to receive an auxiliary component such as a guidewire (not shown). Although inner shaft assembly 404 is described herein as including inner shaft 414 and distal tip 422, distal tip 422 may simply be an extension of inner shaft 414. Further, inner shaft may be several pieces attached together rather than a single piece. Inner shaft 414 extends proximally into housing 442 of handle 440, and is connected to handle 440 such that guidewire lumen 423 provides access for auxiliary components (e.g., a guidewire) therein. Inner shaft 414 may be coupled to handle 440, for example, and not by way of limitation, by adhesives, welding, clamping, and other coupling devices as appropriate. During sliding or longitudinal movement of outer shaft assembly 410, inner shaft assembly 404 is fixed relative to handle 440. However, in other embodiments, inner shaft assembly may be configured to move relative to handle 440, such as by another actuator mechanism.

In an embodiment, tether shaft 450 may be coaxially disposed between inner shaft 404 and outer shaft assembly 410. Tether shaft 450 may be rotated relative to inner shaft assembly 404 and outer shaft assembly 410. With reference to FIGS. 14-15, tether shaft 450 includes a proximal shaft portion 466 and a distal shaft portion 468, and defines lumen 456 extending from a proximal end 452 to a distal end 454 of tether shaft 450. Proximal shaft portion 466 is configured for connection to handle 440. Proximal shaft portion 466 of tether shaft 450 extends proximally into housing 442 of handle 440 and is connected to rotator mechanism 470 of handle 440. Proximal shaft portion 466 is coupled to rotator mechanism 470 such that movement of rotator mechanism 470 causes tether shaft 450 to rotate about a central longitudinal axis $LA_c$ relative to outer shaft assembly 410 and inner shaft assembly 404. Proximal shaft portion 466 may be coupled to rotator mechanism 470, for example, and not by way of limitation by adhesives, welding, clamping, and other coupling devices as appropriate. Tether shaft 450 is thus rotationally movable relative to housing 442, inner shaft assembly 404, and outer shaft assembly 410 by rotator mechanism 470. However, if rotator mechanism 470 is not moved and housing 442 is moved, tether shaft 450 moves with housing 442, not relative to housing 442. A plurality of tether connection points 458 are located at distal shaft portion 468 of tether shaft 450, proximal of distal end 464. Tether connection points 458 are configured to couple distal shaft portion 468 of tether shaft 450 to tethers 460 as described below. While FIG. 16 shows tether connection points 458 arranged circumferentially around tether shaft 450, this is not meant to limit the design and other configurations are contemplating based upon the application. Non-limiting examples of the connection of tethers 460 to tether connection points 458 include configurations releasable by manipulation of the outer shaft 410 such as retainer posts and knot/ball retention apertures, configurations releasable by severing/cutting the tether, and other configurations suitable for the purposes described herein.

In an embodiment, tethers 460 includes a first end 462 coupled to a respective tether connection point 338 of heart valve prosthesis 310, and a second end 464 coupled to tether connection points 458 of tether shaft 450, as shown in FIG. 15.

Tethers 460 are elongated members such as wires. Tethers 460 are relatively rigid such that rotation of tethers 460 increases tautness of tethers 460 such that when taut, rotational torque applied to tethers 460 is transmitted to heart valve prosthesis 310 to rotate heart valve prosthesis 310. Tethers 460 may be connected to tether shaft 450 by methods such as, but not limited to fusing, welding, or mechanical connections. Alternatively, tethers 460 may extend through tether shaft 450 to driver mechanisms (not shown), such as but not limited to sliders, buttons, knobs, and similar mechanisms, to rotate tethers 460 and to release tethers 460 from heart valve prosthesis 310. Tethers 460 may be releasably connected to connection points 338 and tether connection points 458 in any manner suitable for the purpose herein; namely, a sufficiently rigid connection such that rotation of tethers 460 is transmitted to heart valve prosthesis 310 and a removable connection. In an alternative embodiment, first ends 462 of tethers 460 may be coupled to a respective tether connection points 458 of tether shaft 450, and second ends 464 of tethers 460 are releasably coupled to corresponding tether connection points 458 of tether shaft 450. In an embodiment, a portion of each tether 460 is looped through open spaces 17 and around struts 16 of frame 14 at corresponding tether connection points 338.

With the above understanding of components in mind, operation and interaction of components of the present disclosure may be explained herein. As shown in FIG. 15, heart valve prosthesis 310 is disposed in a radially compressed configuration within capsule 407 of outer shaft assembly 410. In this delivery configuration, tethers 460 are coupled to heart valve prosthesis 310 and connection points 338. Delivery device 400 is delivered to an implantation site, such as the site of a native mitral valve. When at the implantation site, outer shaft assembly 410 is retracted proximally, thereby retracting capsule 407 proximally. Capsule 407 is retracted proximally sufficient to expose heart valve prosthesis 310. In the embodiment shown, heart valve prosthesis 310 is self-expanding. Therefore, retraction of capsule 407 enables heart valve prosthesis 310 to self-expand to the radially expanded configuration, as shown in FIG. 16. User actuation of rotator mechanism 470 in direction $R_r$ relative to central longitudinal axis $LA_c$ rotates tether shaft 450 in direction $R_r$ such that tethers 460 are rotated in direction $R_r$. Rotation of tethers 460 imparts a rotational force in direction $R_r$ on inflow rim 315 of heart valve prosthesis 310 such that at least a portion of heart valve prosthesis 310 rotates in direction $R_r$ such that torque anchoring mechanisms 322 are embedded in tissue at the desired implantation site. Stated another way, with heart valve prosthesis 310 in the radially expanded configuration at the desired implantation site, tethers 460 are rotated in direction $R_r$ to embed anchoring mechanisms 322 in tissue, thereby anchoring heart valve prosthesis 310 at the desired implantation site. In an alternative embodiment, tethers 460 are looped through heart valve prosthesis 310 around connection points 338. Once heart valve prosthesis 310 is anchored, outer shaft 410 is retracted further proximally, releasing the second ends 464 of tethers 460 from tether shaft 450 such that tethers 460 may be removed with delivery device 400. In other embodiments, tethers 460 may be released from tether shaft 450 and remain with heart valve prosthesis 310. In yet another embodiment, tethers 460 may be severed and a portion coupled to tether shaft 450 removed with delivery device 400 and a portion coupled to heart valve prosthesis 310 remaining with heart valve prosthesis 310.

Figure 17:
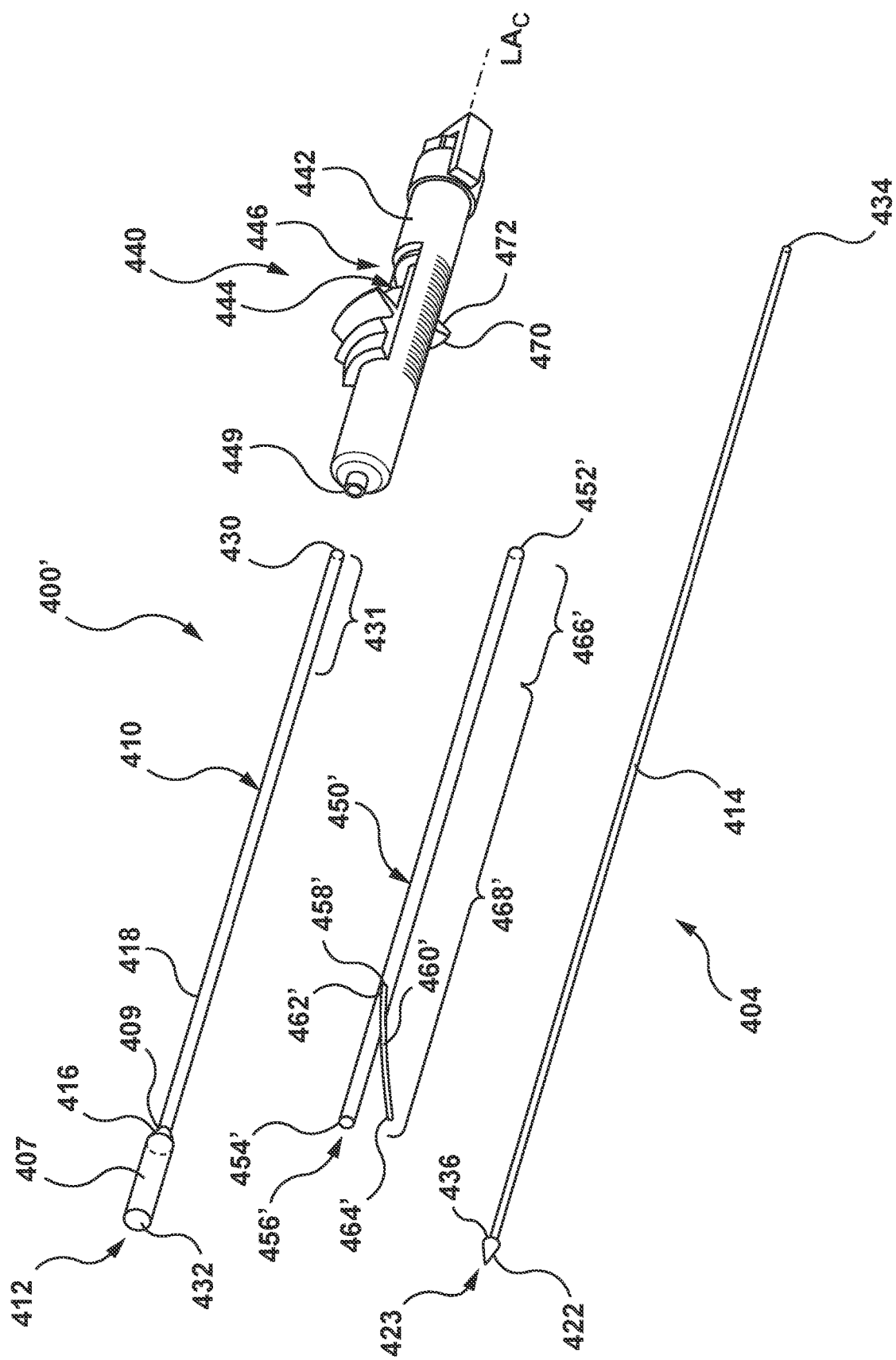
FIG. 17 is an exploded perspective illustration of an embodiment of a delivery device according to an embodiment hereof.
Figure 18:
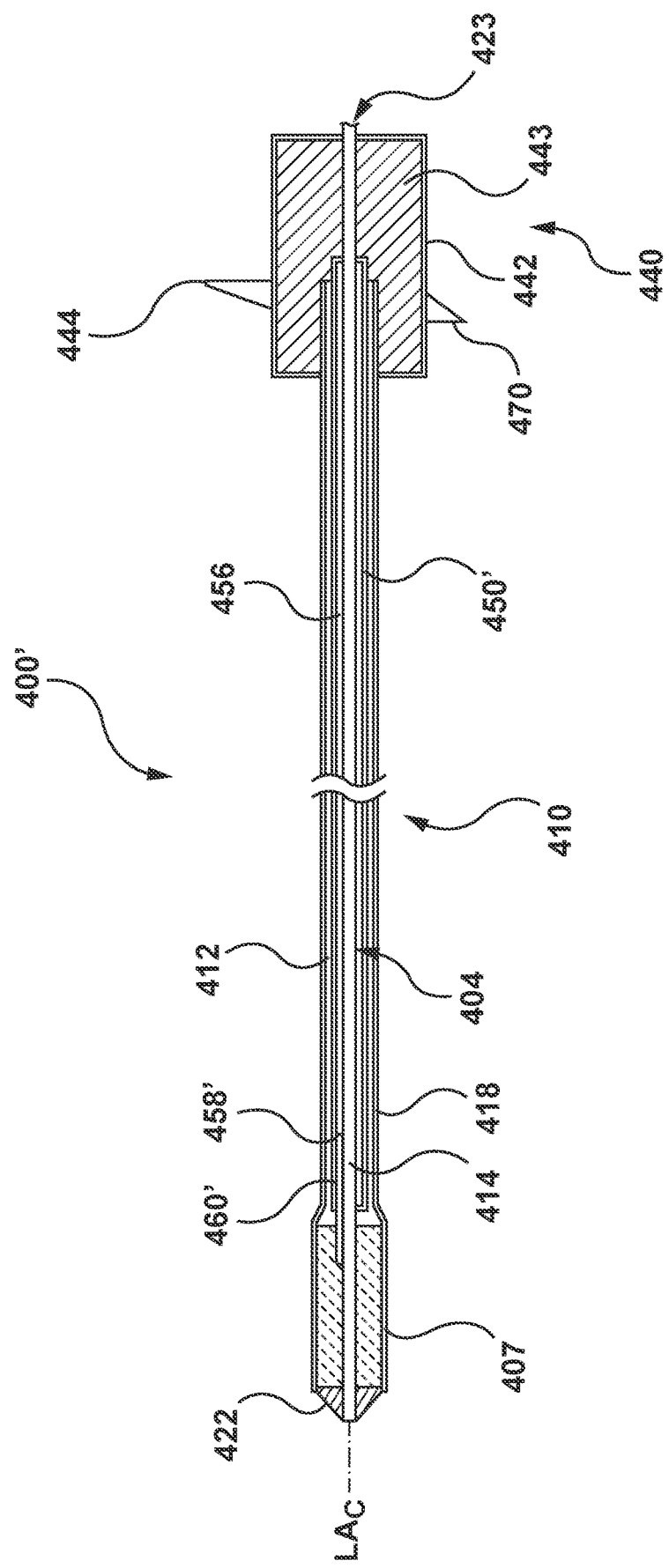
FIG. 18 is a side view illustration of the delivery device of FIG. 17.
Figure 19:
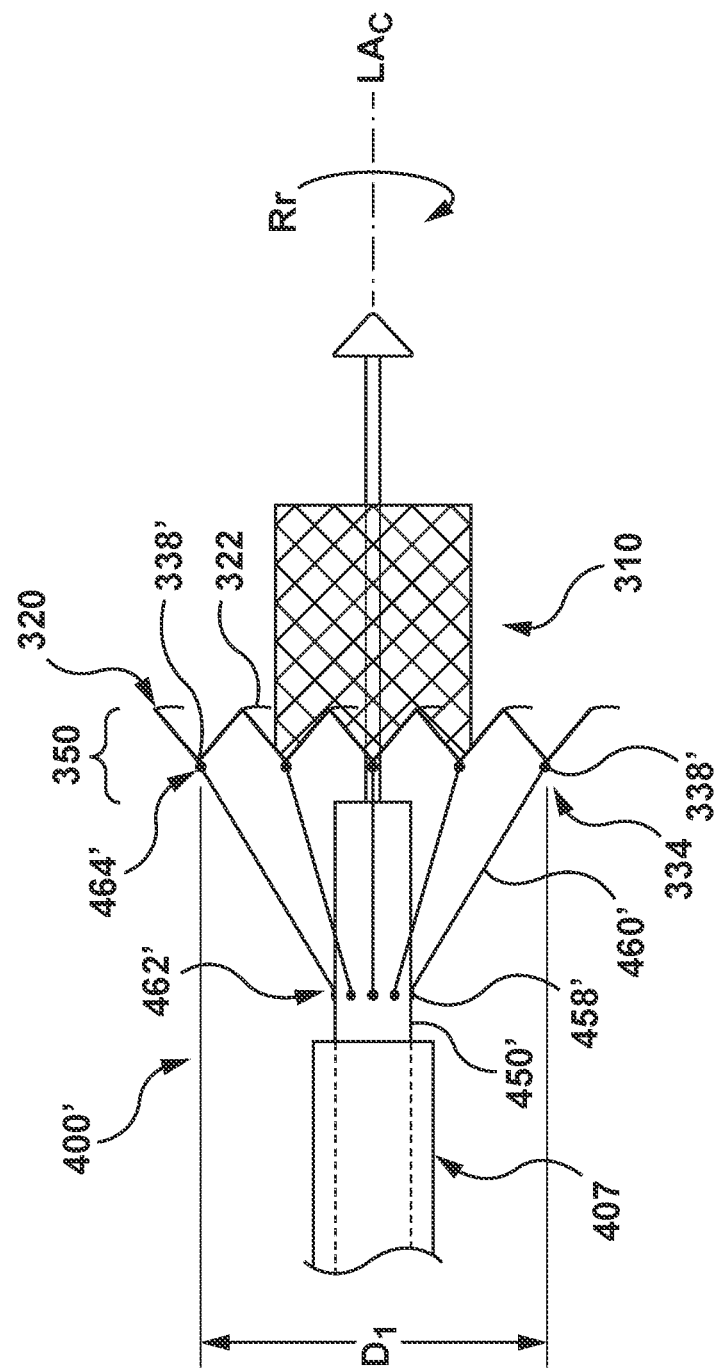
FIG. 19 is a side illustration of the delivery device of FIG. 17 and heart valve prosthesis of FIG. 13.

FIGS. 17-19 illustrate another embodiment of delivery device 400' for delivering and deploying a heart valve prosthesis 10. Delivery device 400' is similar to the embodiment of FIGS. 14-16, so only the differences between the embodiments will be described in detail here. Features not specifically described may be like those described with respect to the embodiment of FIGS. 14-16, or other embodiments described herein. In the embodiment of FIGS. 17-19, instead of a tether shaft 450 and tethers 460, as described above, delivery device 400' includes a rod shaft 450' and rods 460'.

In an embodiment, rod shaft 450' may be coaxially disposed between inner shaft 404 and outer shaft assembly 410. Rod shaft 450' may be rotated relative to inner shaft assembly 404 and outer shaft assembly 410. With reference to FIGS. 17-18, rod shaft 450' includes a proximal shaft portion 466' and a distal shaft portion 468', and defines a lumen 456' extending from a proximal end 452' to a distal end 454' of rod shaft 450'. Proximal shaft portion 466' is configured for connection to handle 440. Proximal shaft portion 466 of rod shaft 450' extends proximally into housing 442 of handle 440 and is connected to rotator mechanism 470 of handle 440. Proximal shaft portion 466' is coupled to rotator mechanism 470 such that movement of rotator mechanism 470 causes rod shaft 450' to rotate about a central longitudinal axis $LA_c$ relative to outer shaft assembly 410 and inner shaft assembly 404. Proximal shaft portion 466' may be coupled to rotator mechanism 470, for example, and not by way of limitation by adhesives, welding, clamping, and other coupling devices as appropriate. Rod shaft 450' is thus rotationally movable relative to housing 442, inner shaft assembly 404, and outer shaft assembly 410 by rotator mechanism 470. However, if rotator mechanism 470 is not moved and housing 442 is moved, rod shaft 450' moves with housing 442, not relative to housing 442. A plurality of rod connection points 458' are located at distal shaft portion 468 of rod shaft 450'. Rod connection points 458' are configured to pivotably couple distal shaft portion 468' of rod shaft 450' to rods 460' as described below. While FIG. 19 shows rod connection points 458' arranged circumferentially around rod shaft 450', this is not meant to limit the design and other configurations are contemplating based upon the application.

In an embodiment, each rod 460' includes an atraumatic first end 462' and a second end 464'. Each second end 464' is pivotably coupled to a corresponding rod connection point 458' of rod shaft 450', as shown in FIG. 17. Rods 460' are elongated rigid members such as wires. Rods 460' include a pivotably collapsed configuration when disposed within outer shaft assembly 410, and a pivotably expanded configuration with first ends 462' radially expanded outward from inner shaft 414, and second ends 464' pivotably coupled to rod shaft 450', as shown in FIG. 19. Rods 460' are self-expanding in that they remain in the pivotably expanded configuration unless compressed to the pivotably collapsed configuration when retained within capsule 407 and outer shaft 410. When in the pivotably expanded configuration, first ends 462' are radially expanded to a first diameter D1. First diameter D1 is equal to the diameter of connection points 338' such that advancement distally of delivery device 400' selectively couples first ends 462' with connection points 338' on a torque portion 350 of heart valve prosthesis 310. First ends 462' will remain selectively coupled with connection points 338' with continued distal force on delivery device 400'. When selectively coupled, rotation of rod shaft 450' and pivotably coupled rods 460' is transmitted to heart valve prosthesis 310 to rotate heart valve prosthesis 310. Rods 460' may be pivotably connected to rod shaft 450' by methods such as, but not limited to fusing, welding, flex-joint, or mechanisms suitable for the purposes described herein. Rods 460' may be selectively coupled to connection points 338' by various methods such as, but not limited to rod-cup mechanisms, rod-slot mechanisms, friction-fit mechanisms, or other methods suitable for the purposes described herein.

With the above understanding of components in mind, operation and interaction of components of the present disclosure may be explained herein. As shown in FIG. 18, heart valve prosthesis 310 is disposed in a radially compressed configuration within capsule 407 of outer shaft assembly 410. In this delivery configuration, rods 460' are retained in the pivotably collapsed configuration within capsule 407 and outer shaft 410 with first ends 462, selectively coupled to heart valve prosthesis 310 at rod connection points 338'. Delivery device 400' is delivered to an implantation site, such as the site of a native mitral valve. When at the implantation site, outer shaft assembly 410 is retracted proximally, thereby retracting capsule 407 proximally. Capsule 407 is retracted proximally sufficient to expose heart valve prosthesis 310. In the embodiment shown, heart valve prosthesis 310 is self-expanding. Therefore, retraction of capsule 407 enables heart valve prosthesis 310 to self-expand to the radially expanded configuration. Once heart valve prosthesis is in the radially expanded configuration, outer shaft assembly 410 is retracted further proximally, thereby retracting capsule 407 proximally. Capsule 407 is retracted proximally sufficient to expose rods 460'. In the embodiment shown, rods 460' are self-expanding. Therefore, retraction of capsule 407 enables rods 460' to self-expand to the pivotably expanded configuration, as shown in FIG. 19. With rods 460' in the pivotably expanded configuration, delivery device 400' is advanced distally until each first end 462' is selectively coupled with a corresponding connection point 338' of heart valve prosthesis 310. Once selectively coupled by distal force on delivery device 400' user actuation of rotator mechanism 470 in direction $R_r$ relative to central longitudinal axis $LA_c$ rotates rod shaft 450' in direction $R_r$ such that rods 460' are rotated in direction $R_r$. Rotation of rods 460' imparts a rotational force in direction $R_r$ heart valve prosthesis 310 such that at least a portion of heart valve prosthesis 310 rotates in direction $R_r$ such that torque anchoring mechanisms 322 are embedded in tissue at the desired implantation site. Once heart valve prosthesis 310 is anchored, delivery device 400' is retracted proximally such that rods 460' are selectively uncoupled form connection points 338'. When rods 460' are selectively uncoupled form connection points 338, outer shaft assembly 410 is advanced distally, thereby advancing capsule 407 distally. Capsule 407 is advanced distally sufficient to radially compress rods 460' to the pivotably collapsed configuration. Delivery device 400' may be then be retracted proximally for removal from the implantation site. While rod shaft 450' and rods 460' are described herein as part of delivery device 400', this is not meant to limit the design, and in other embodiments, rod shaft 450' and rods 460' may be a separate device advanced to the implantation site following the expansion of heart valve prosthesis 310 and removal of delivery device 400'.

Features of any of the embodiments described above may be used with any of the other embodiments described above. Further, variations in the number and types of tethers, rods, shafts, actuating mechanisms, and similar items may be made within the scope of the invention. Other materials than those described above may also be used within the scope of the invention.

Figure 20:
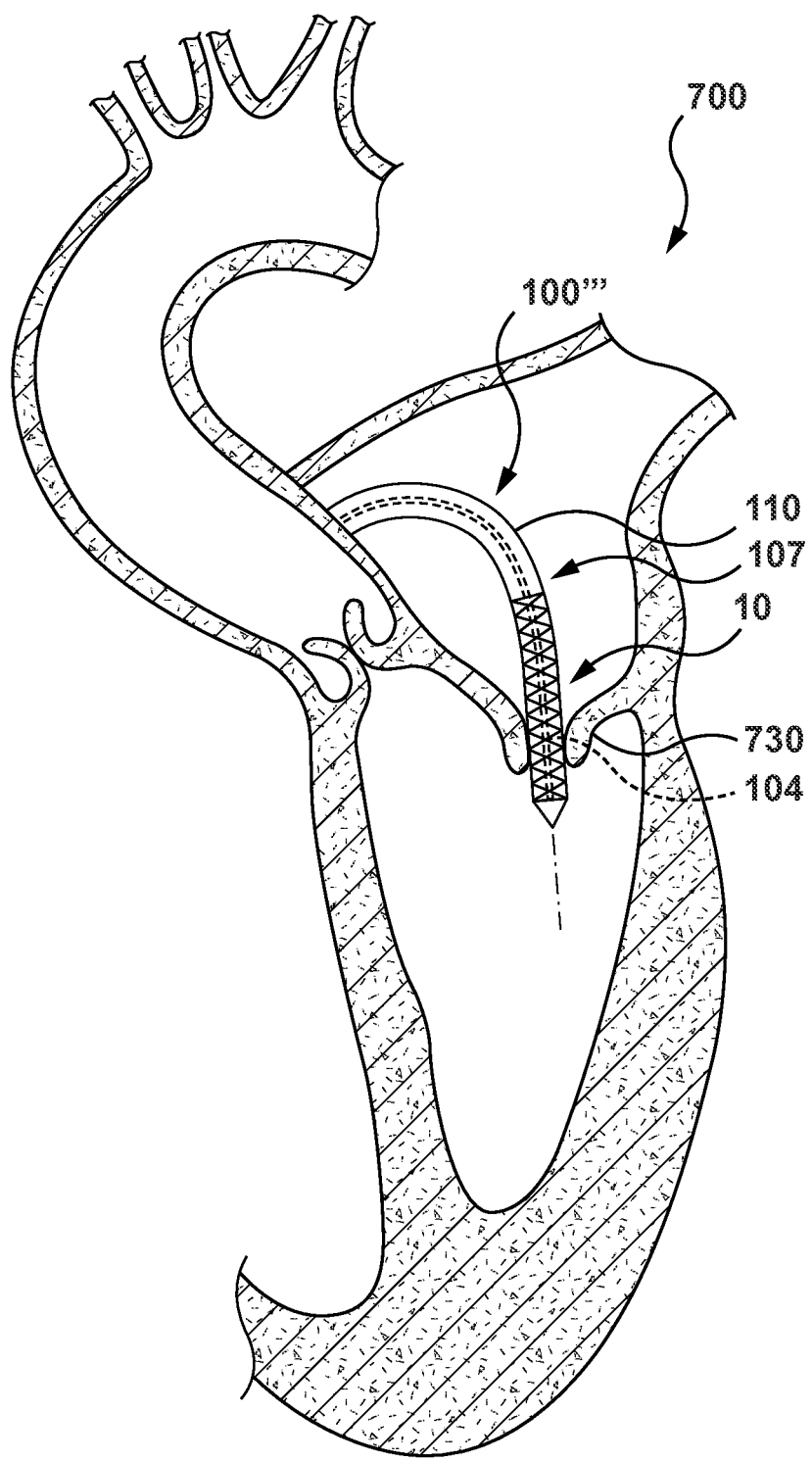
FIGS. 20-24 are schematic illustrations of a method of delivering a heart valve prosthesis.

A method of deploying and anchoring a heart valve prosthesis at a desired implantation site with a delivery device in accordance with an embodiment hereof is schematically represented in FIGS. 20-24. The method steps of FIGS. 20-24 are described with respect to delivery device 100''' including dumbbell-shaped balloon 170. However, this embodiment may be used with other delivery devices described herein. Using established percutaneous transcatheter delivery procedures, delivery device 100''' is introduced into a patient's vasculature, advanced over a guidewire, and positioned at a treatment site of a damaged or diseased native valve, which in this embodiment is a native mitral valve 730 of a heart 700, as shown in FIG. 20.

Figure 21:
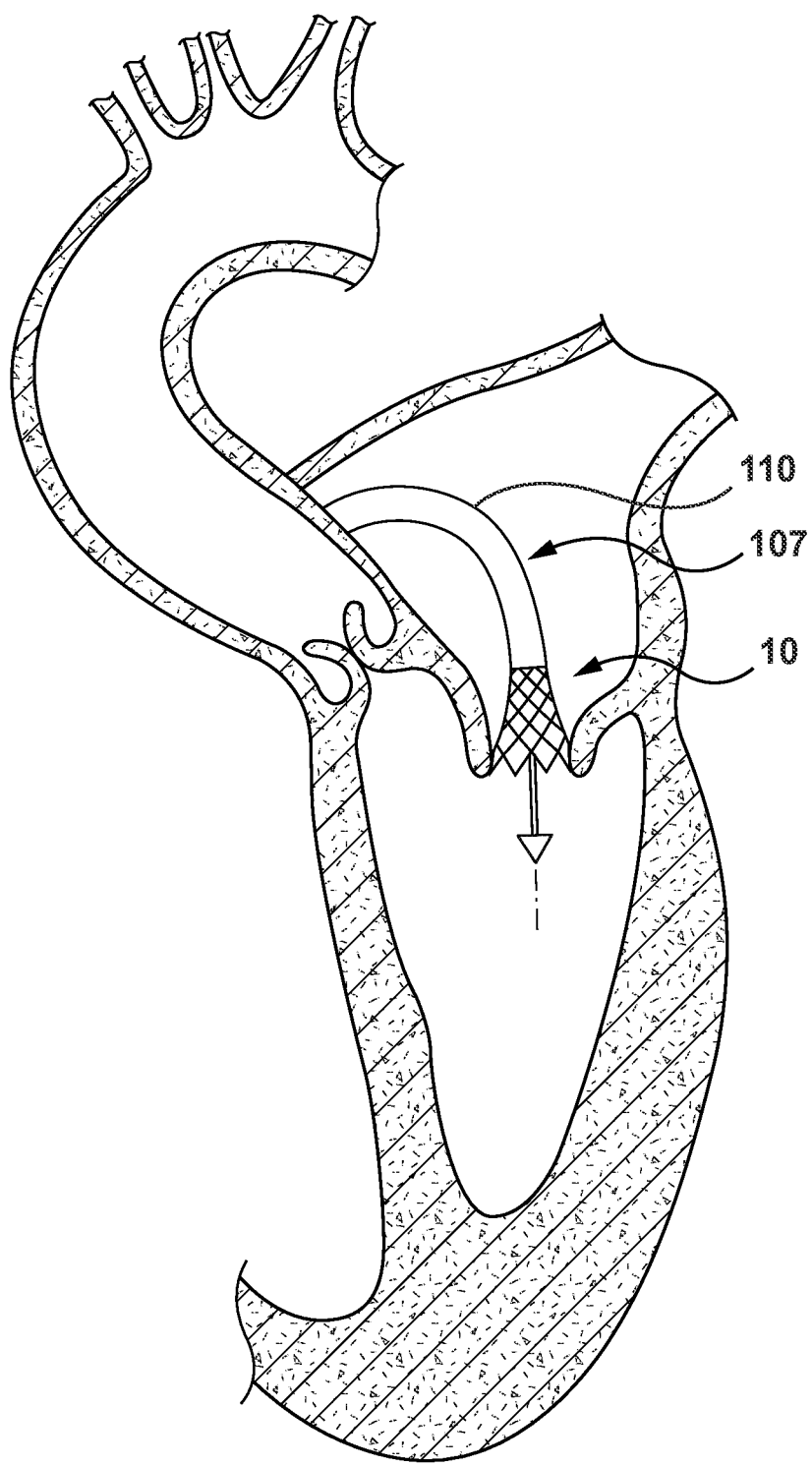

With delivery device 100''' in place, actuator mechanism 144 of handle 140 is operated proximally to outer shaft assembly 110. As capsule 107 of outer shaft assembly 110 is retracted proximally, heart valve prosthesis 10 transitions from the radially collapsed configuration to the radially expanded configuration, as shown in FIG. 21.

Figure 22:
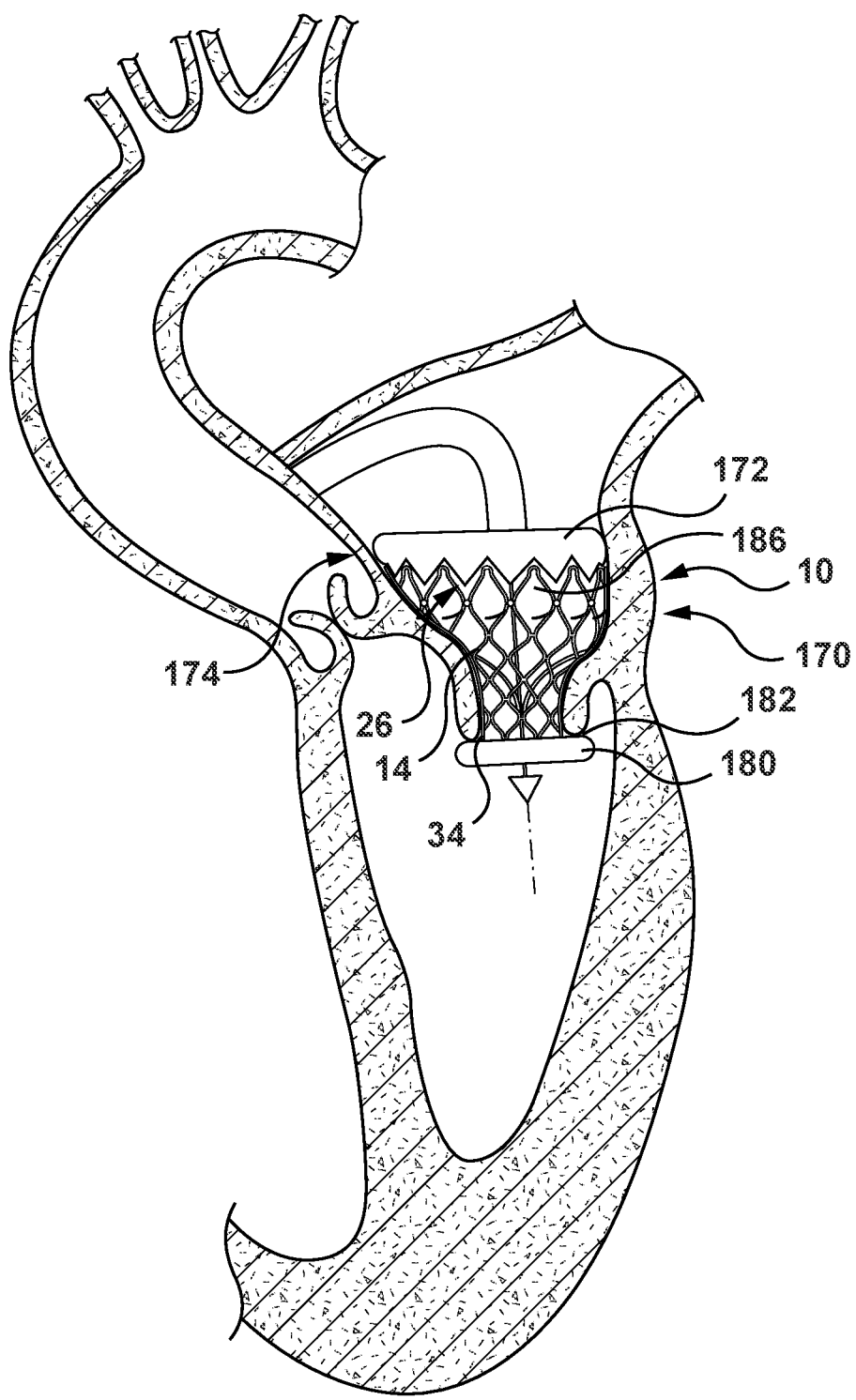

Once heart valve prosthesis 10 is in the radially expanded configuration, inflation fluid is injected into dumbbell-shaped balloon 170 such that dumbbell-shaped balloon 170 transitions from the uninflated configuration to the inflated configuration as shown in FIG. 22. Balloon 170 is configured such that when in the inflated configuration, shaped end 174 of first portion 172 of dumbbell-shaped balloon 170 engages corresponding shaped end 26 of heart valve prosthesis 10, proximal end 182 of second portion 180 of dumbbell-shaped balloon 170 abuts proximal end 34 of heart valve prosthesis 10, and outer surface 189 (not shown in FIGS. 20-24) of third portion 186 of dumbbell-shaped balloon 170 engages the inner surface of frame 14 of heart valve prosthesis 10.

Figure 23:
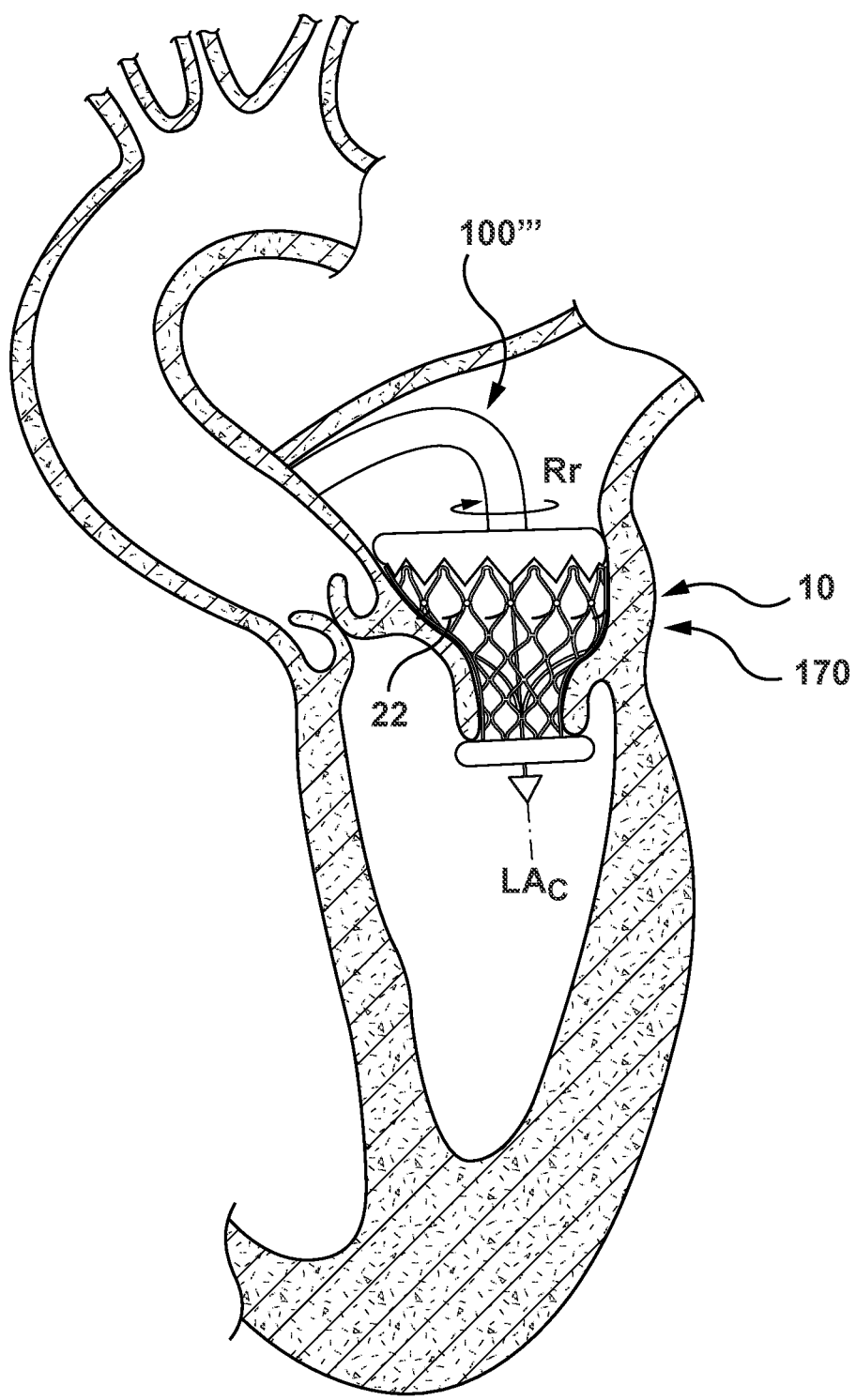

Next, delivery device 100''' is rotated in direction $R_r$ about central longitudinal axis $LA_c$. Rotation of delivery device 100''' in direction $R_r$ about central longitudinal axis $LA_c$, rotates dumbbell-shaped balloon 170 in direction $R_r$, which rotates at least a portion of heart valve prosthesis 10 in direction $R_r$, and torque anchoring mechanism 22 is embedded into tissue at the desired implantation site, as shown in FIG. 23.

Figure 24:
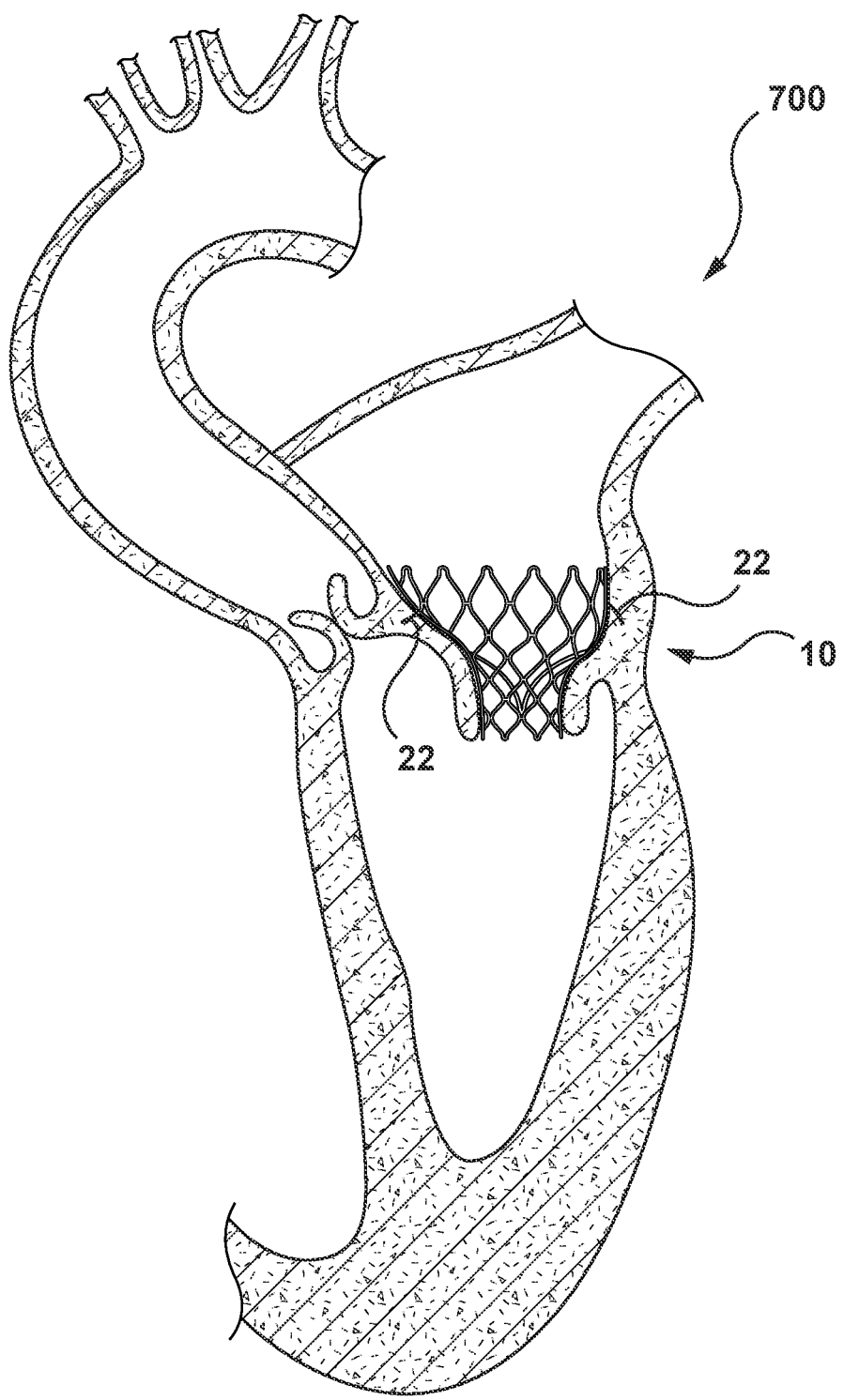

Next, inflation fluid is drained from dumbbell-shaped balloon 170 such that dumbbell-shaped balloon 170 transitions from the inflated configuration to the first uninflated configuration. Delivery device 100''' is retracted through patient's vasculature, leaving heart valve prosthesis 10 anchored in at the site of the native mitral valve, as shown in FIG. 24.

The method described with respect to FIGS. 20-24 may be used with other devices and features described herein. Further, variations, additional steps, and fewer steps may be utilized as would be understood by those skilled in the art.

Figure 25:
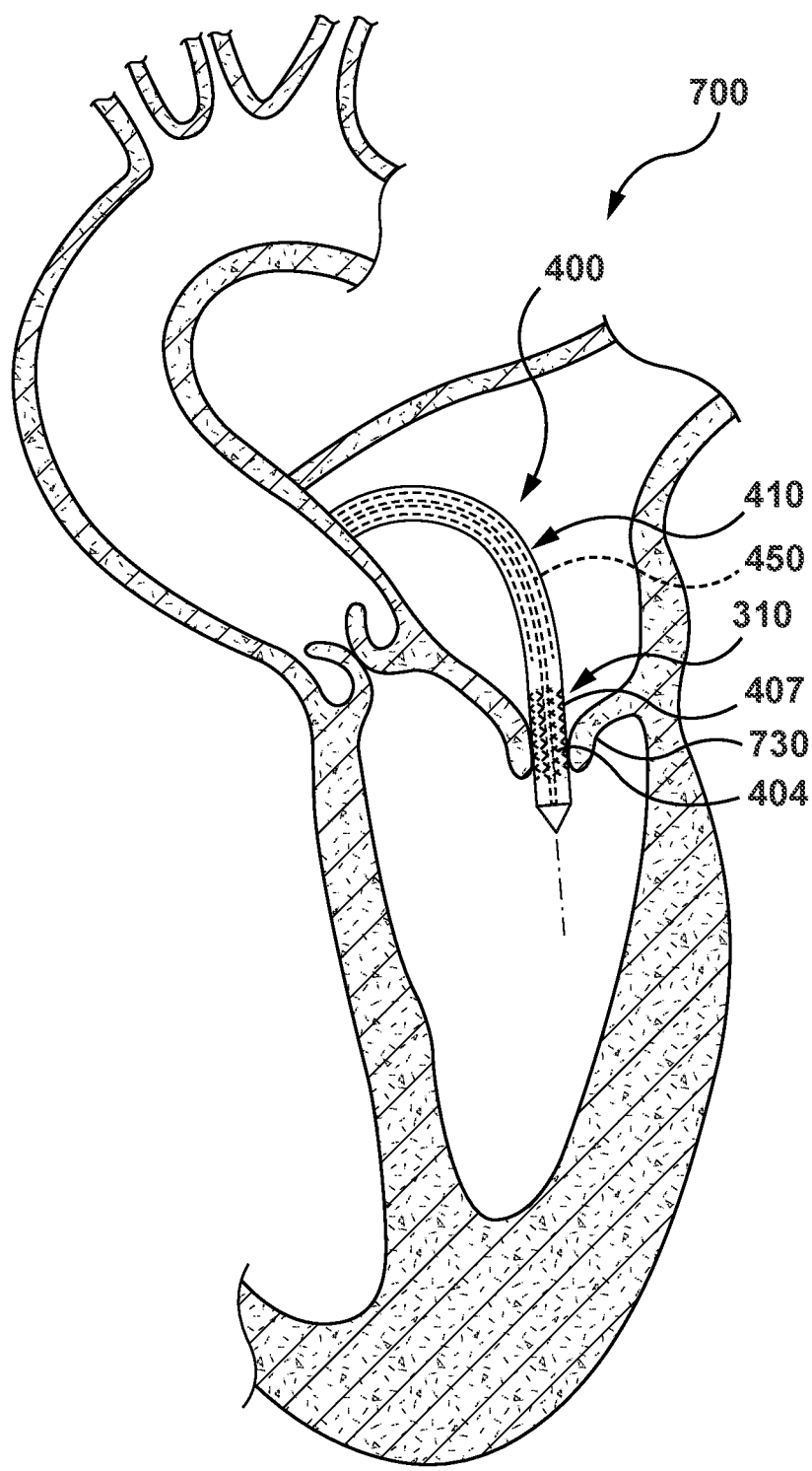
FIGS. 25-29 are schematic illustrations of another method of delivering a heart valve prosthesis.

Another method of deploying and anchoring a heart valve prosthesis at a desire implantation site with a delivery device in accordance with an embodiment hereof is schematically represented in FIGS. 25-29. The method steps of FIGS. 25-29 are described with respect to delivery device 400 and heart valve prosthesis 310 described previously. Using established percutaneous transcatheter delivery procedures, delivery device 400 is introduced into a patient's vasculature, advanced over a guidewire, and positioned at a treatment site of a damaged or diseased native valve, which in this embodiment is native mitral valve 730 of heart 700, as shown in FIG. 25.

Figure 26:
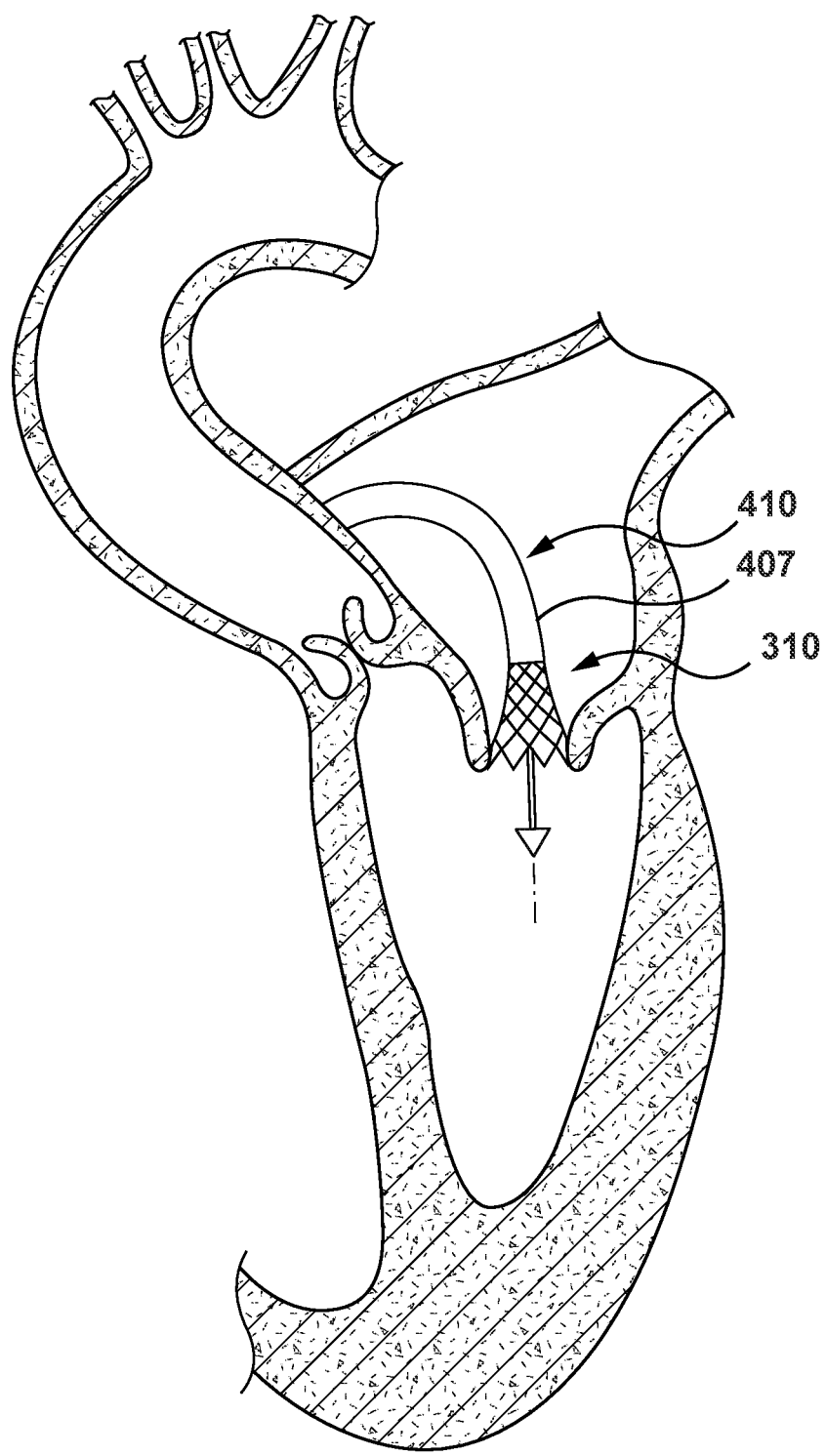

Actuator mechanism 444 of handle 440 is operated proximally to retract outer shaft assembly 410. As capsule 407 of outer shaft assembly 410 is retracted proximally, heart valve prosthesis 310 transitions from the radially collapsed configuration to the radially expanded as shown in FIG. 26.

Figure 27:
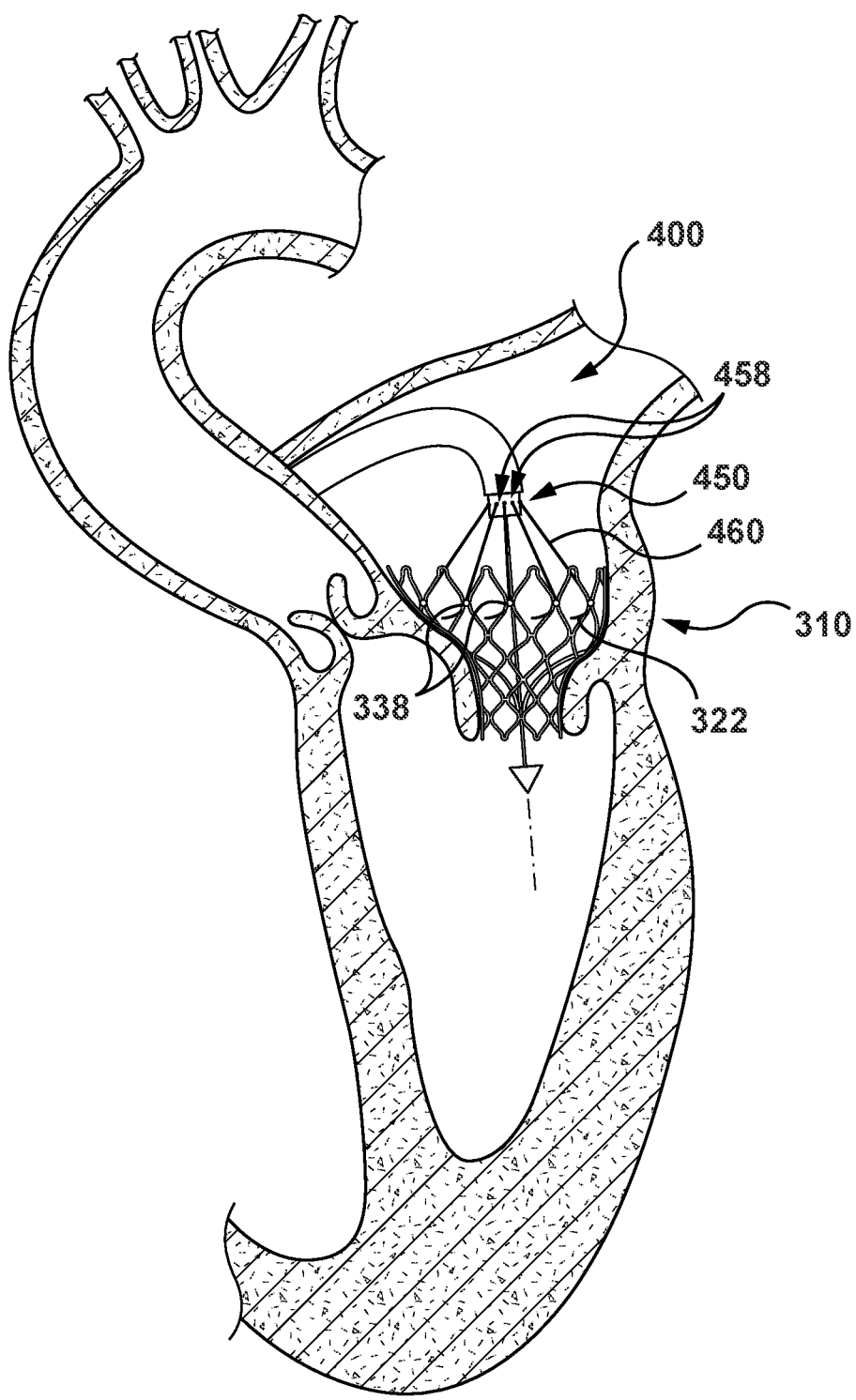
Figure 28:
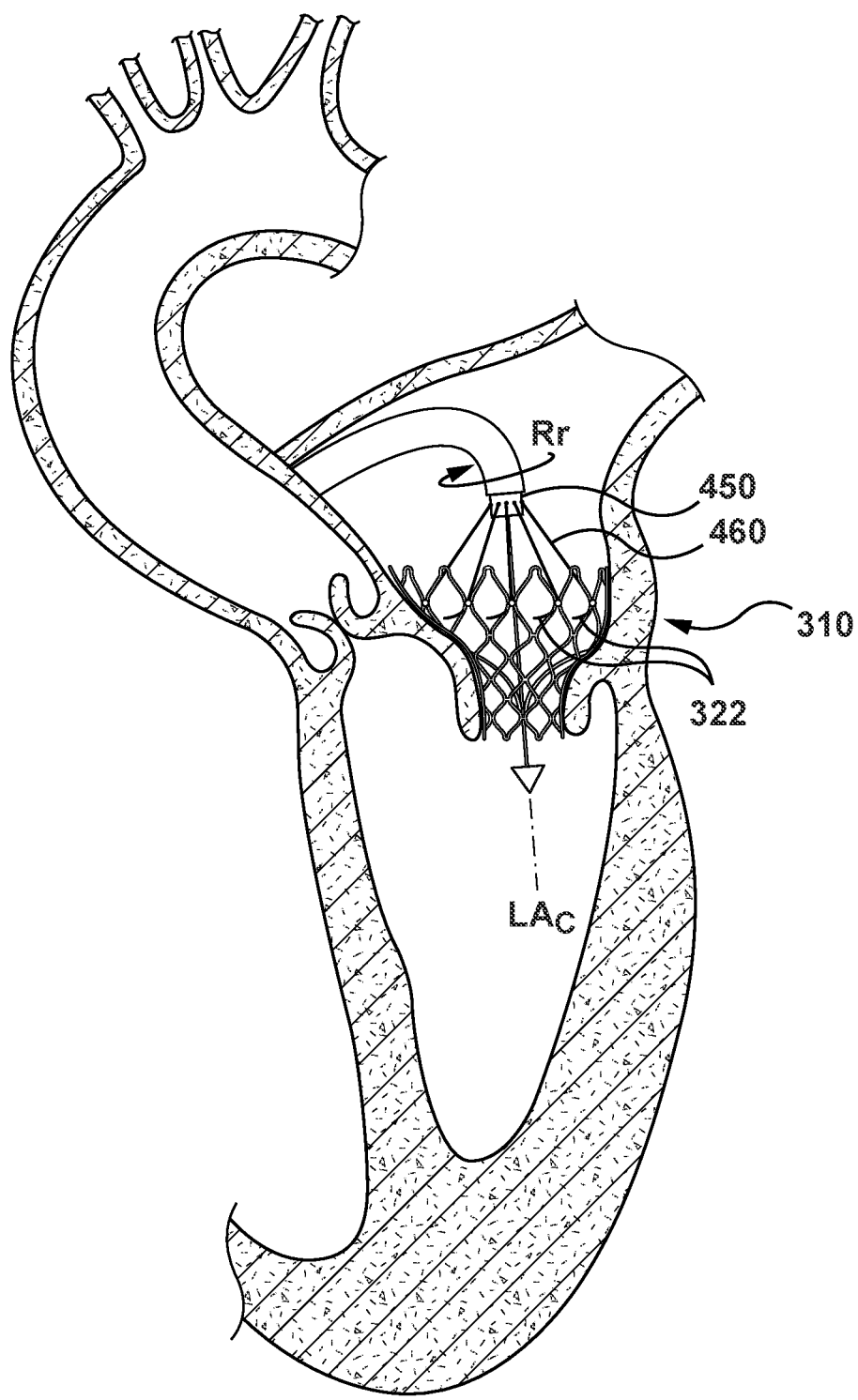

With heart valve prosthesis 310 in the radially expanded configuration, shown in FIG. 27, rotator mechanism 470 of handle 440 is rotated in direction $R_r$ about central longitudinal axis $LA_c$. Rotation of rotator mechanism 470 causes tether shaft 450 and tethers 460 attached thereto to rotate in direction $R_r$. Rotation tethers 460 causes least a portion of heart valve prosthesis 310 to rotate in direction $R_r$, thereby embedding torque anchoring mechanisms 322 of heart valve prosthesis 310 into tissue at the desired implantation site, as shown in FIG. 28.

Figure 29:
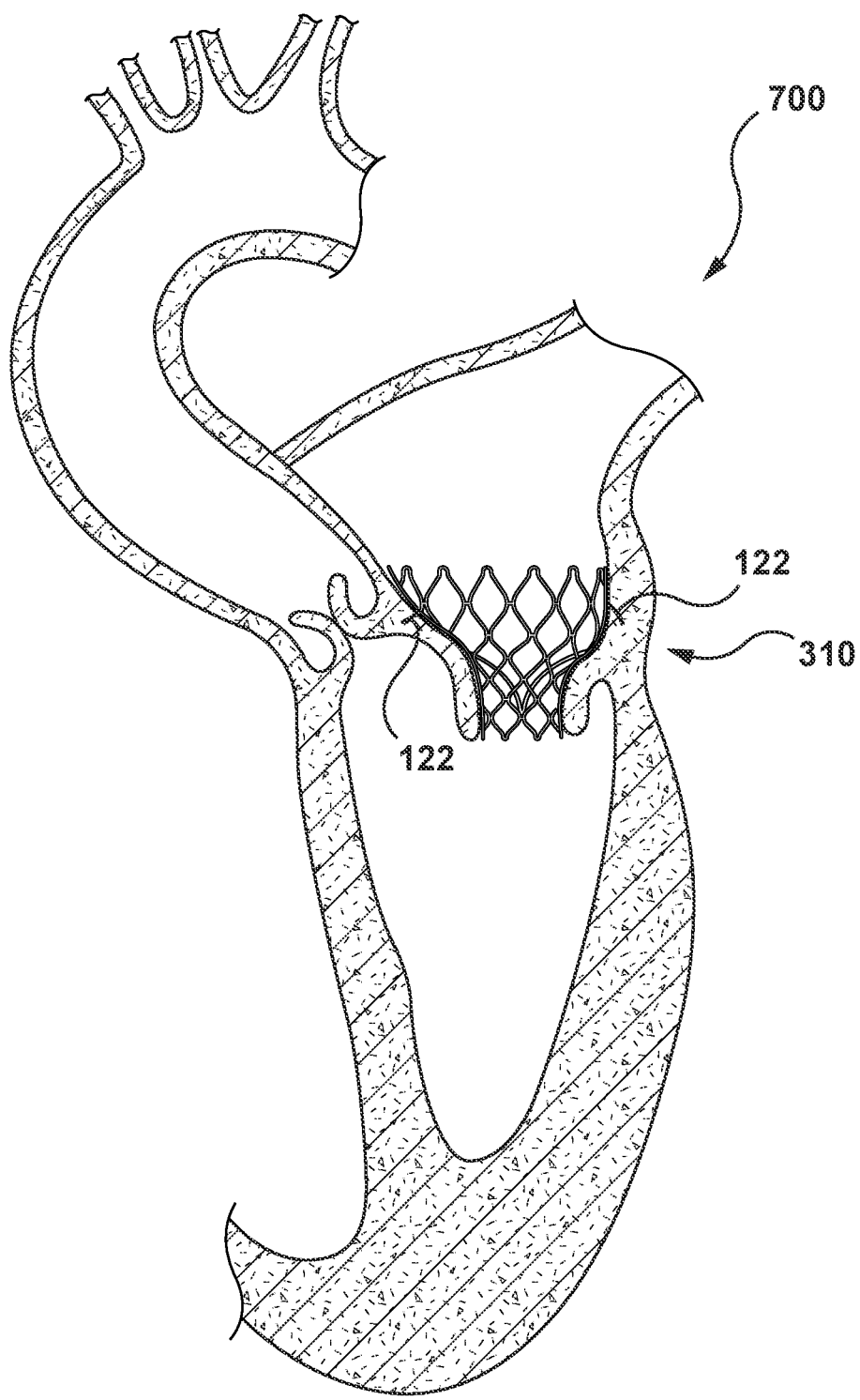

Tethers 460 may then be released from heart valve prosthesis 310, as described above. Delivery device 400 may then be removed from the patient, leaving heart valve prosthesis 310 anchored in heart 700, as shown in FIG. 29.

The method described with respect to FIGS. 25-29 may be used with other devices and features described herein. Further, variations, additional steps, and fewer steps may be utilized as would be understood by those skilled in the art. For example, and not by way of limitation, delivery device 400 may be used with the heart valve prosthesis described with respect to FIGS. 10A-11D above, or the heart valve prostheses described with respect to FIG. 35, below.

Figure 30:
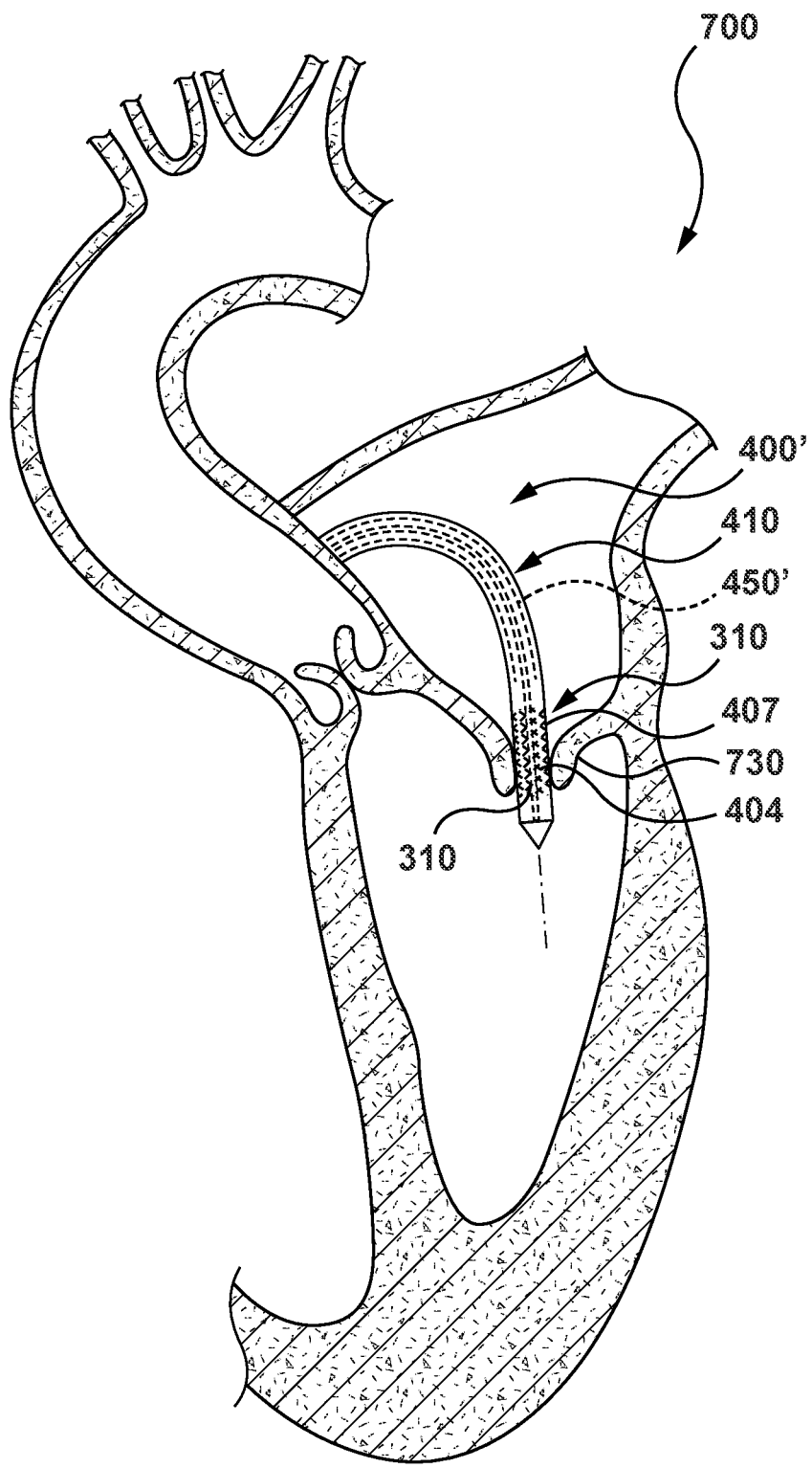
FIGS. 30-34 are schematic illustrations of another method of delivering a heart valve prosthesis.

Another method of deploying and anchoring a heart valve prosthesis at a desire implantation site with a delivery device in accordance with an embodiment hereof is schematically represented in FIGS. 30-34. The method steps of FIGS. 30-34 are described with respect to delivery device 400' and heart valve prosthesis 310 described previously. Using established percutaneous transcatheter delivery procedures, delivery device 400' is introduced into a patient's vasculature, advanced over a guidewire, and positioned at a treatment site of a damaged or diseased native valve, which in this embodiment is native mitral valve 730 of heart 700, as shown in FIG. 30.

Figure 31:
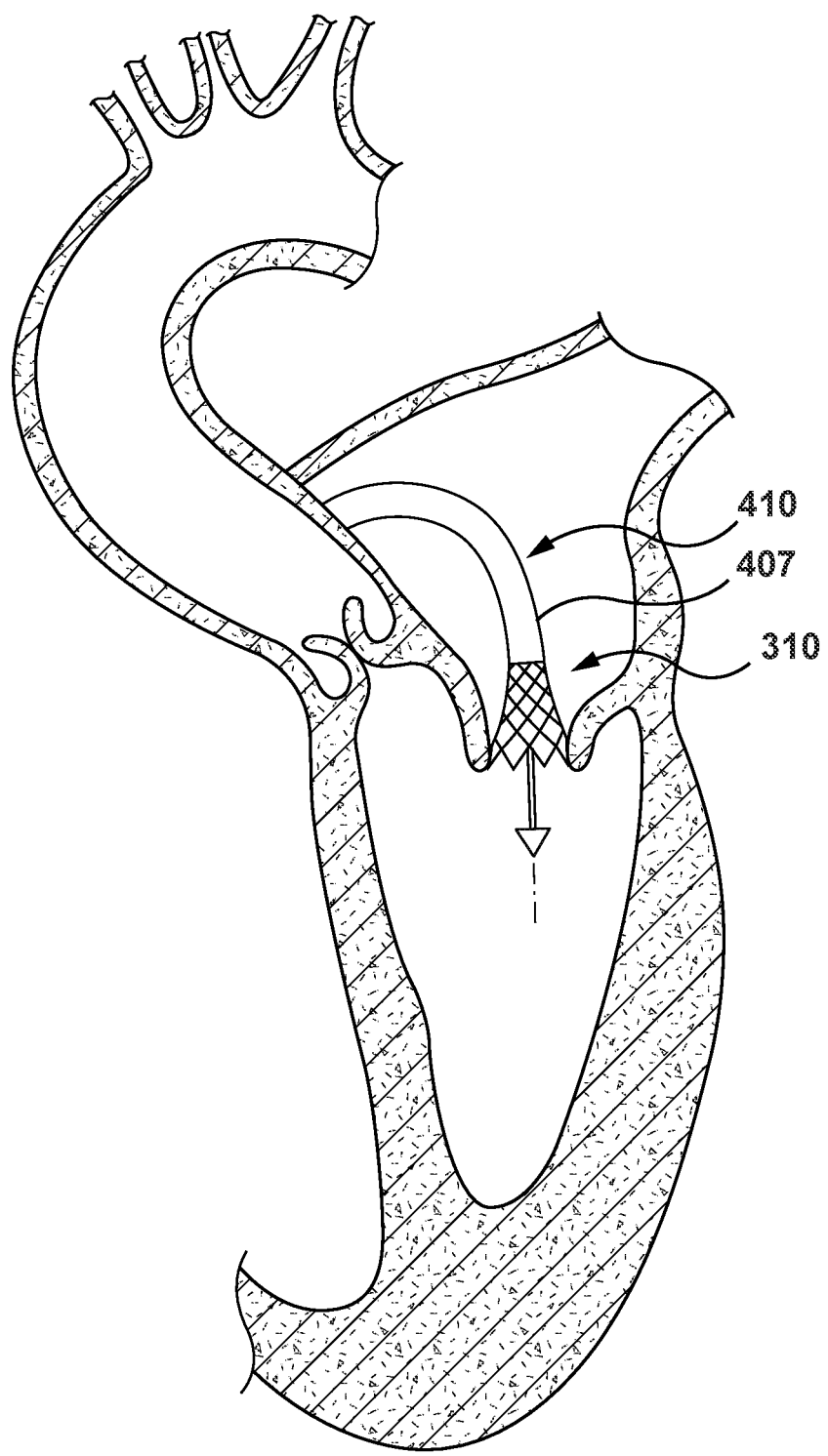

Actuator mechanism 444 of handle 440 is operated proximally to retract outer shaft assembly 410. As capsule 407 of outer shaft assembly 410 is retracted proximally, heart valve prosthesis 310 transitions from the radially collapsed configuration to the radially expanded configuration. With the heart valve prosthesis 310 in the radially expanded configuration, delivery device 400' is advanced distally. Actuator mechanism 444 of handle 440 is operated proximally to retract outer shaft assembly 410. As capsule 407 of outer shaft assembly 410 is retracted proximally, rods 460' of rod shaft 450' transition from the pivotably collapsed configuration to the pivotably expanded configuration. Delivery device 400' is advanced distally and rods 460' engage connection points 338' of heart valve prosthesis 310, as shown in FIG. 31.

Figure 32:
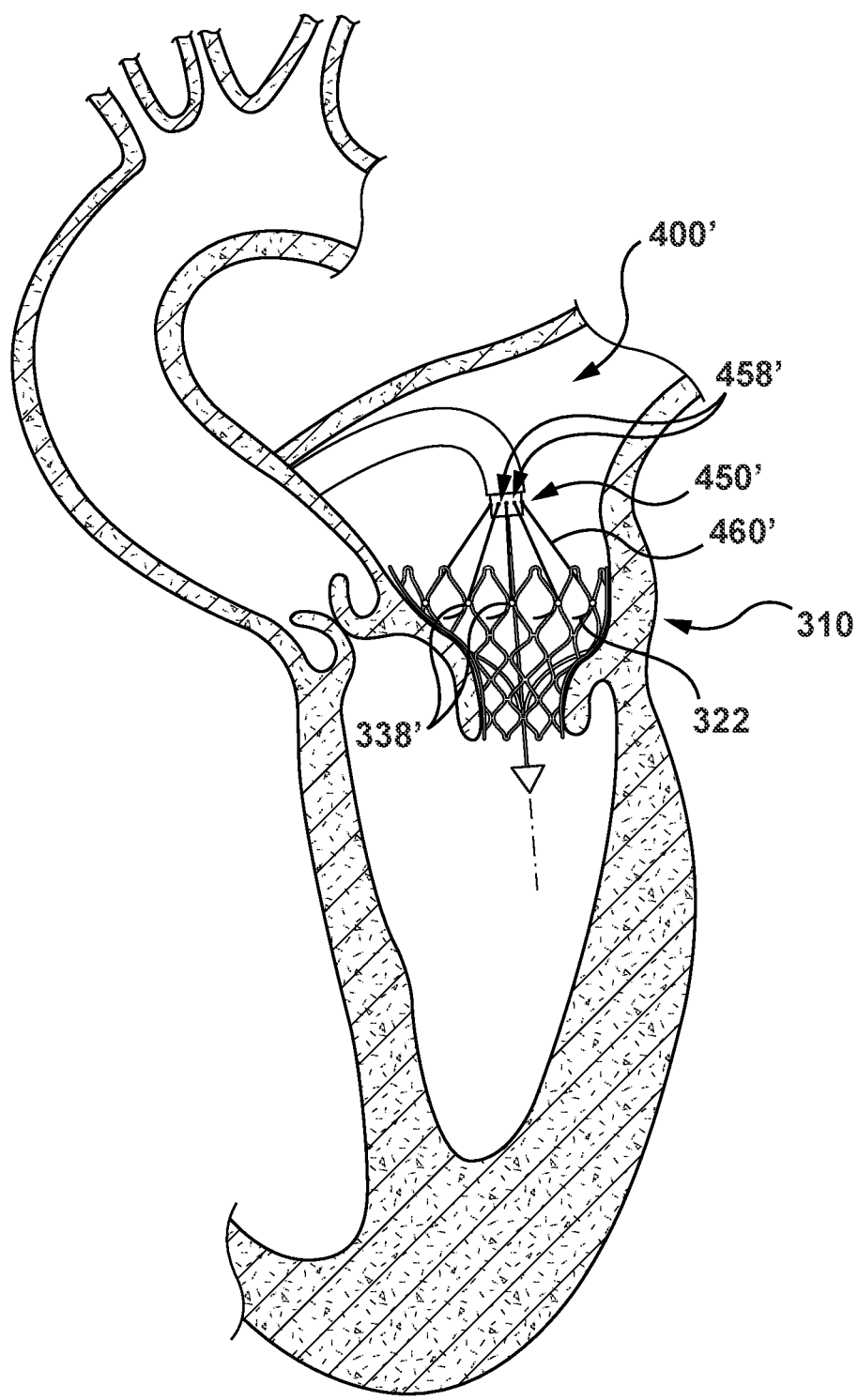
Figure 33:
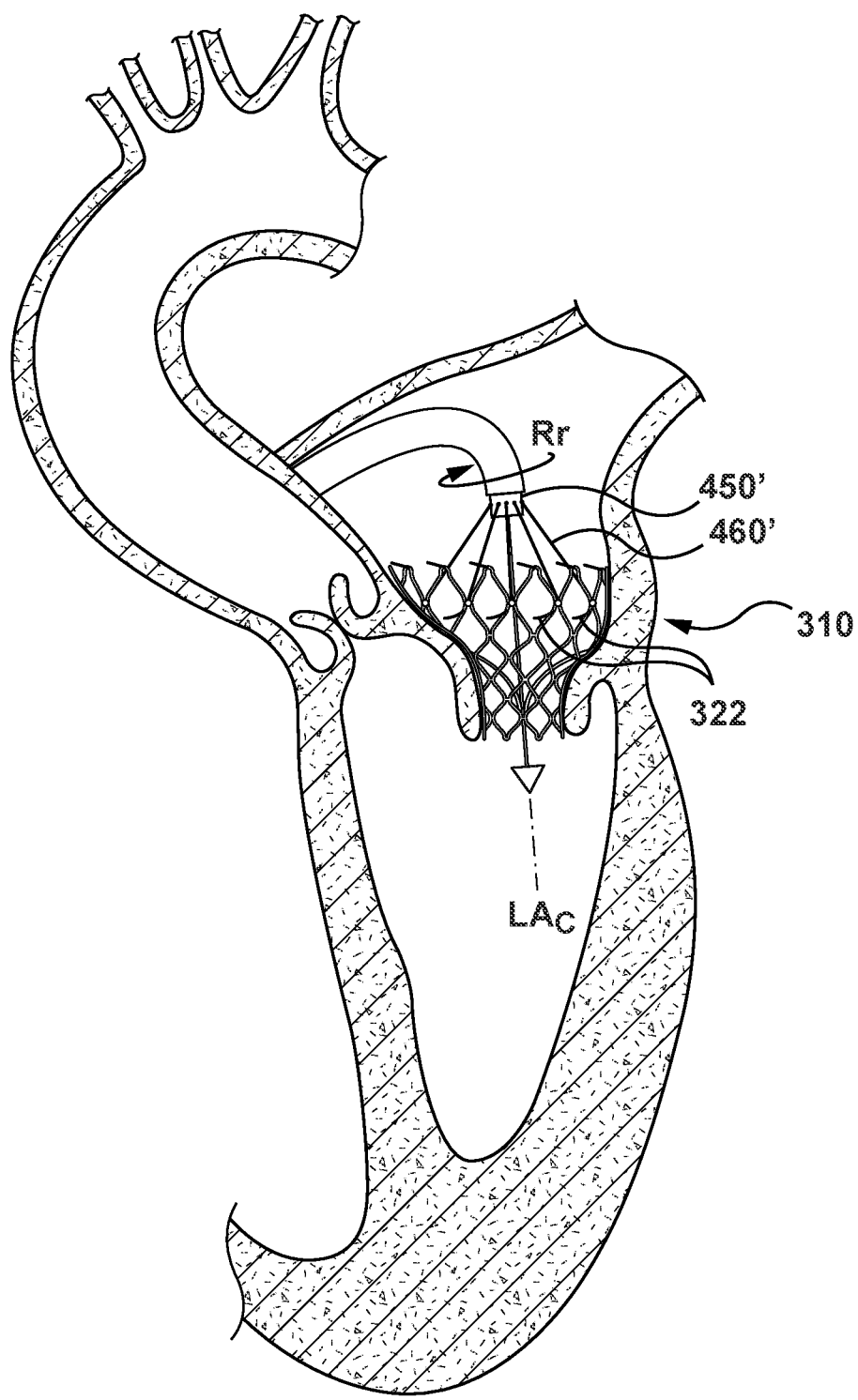

With heart valve prosthesis 310 in the radially expanded configuration, shown in FIG. 32 and rods 460' engaged thereto, rotator mechanism 470 of handle 440 is rotated in direction $R_r$ about central longitudinal axis $LA_c$. Rotation of rotator mechanism 470 causes rod shaft 450' and rods 460' attached thereto to rotate in direction $R_r$. Rotation of rods 460' causes at least a portion of heart valve prosthesis 310 to rotate in direction $R_r$, thereby embedding torque anchoring mechanisms 322 of heart valve prosthesis 310 into tissue at the desired implantation site, as shown in FIG. 33.

Figure 34:
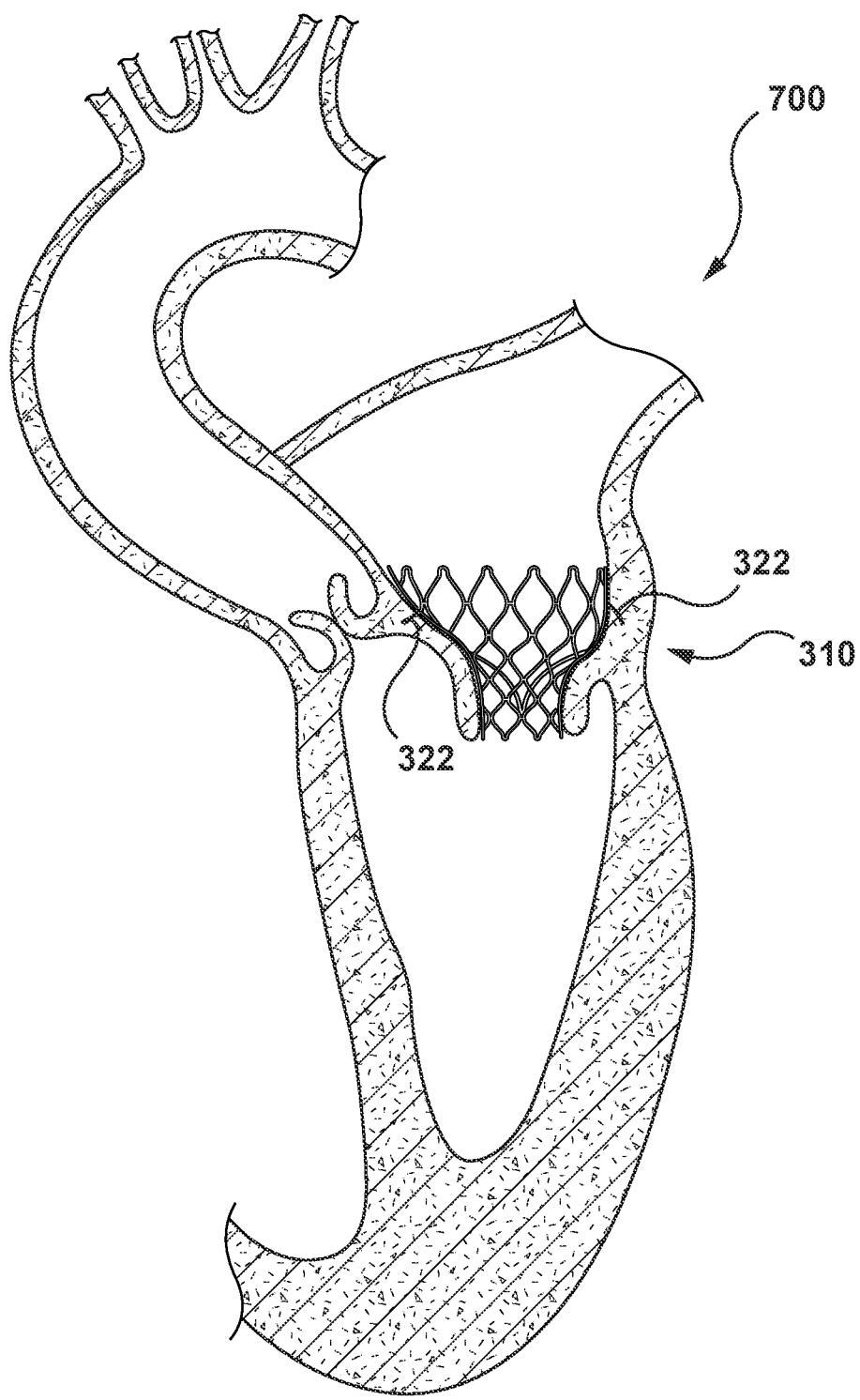

Delivery device 400' may then be retracted proximally such that rods 460' disengage and are released from connection points 338' of heart valve prosthesis 310. Outer shaft 410 (including capsule 407) is advanced distally and rods 460' radially compress from the pivotably expanded configuration to the pivotably collapsed configuration. Delivery device 400' may then be removed from the patient, leaving heart valve prosthesis 310 anchored in heart 700, as shown in FIG. 34.

The method described with respect to FIGS. 30-34 may be used with other devices and features described herein. Further, variations, additional steps, and fewer steps may be utilized as would be understood by those skilled in the art.

Figure 35:
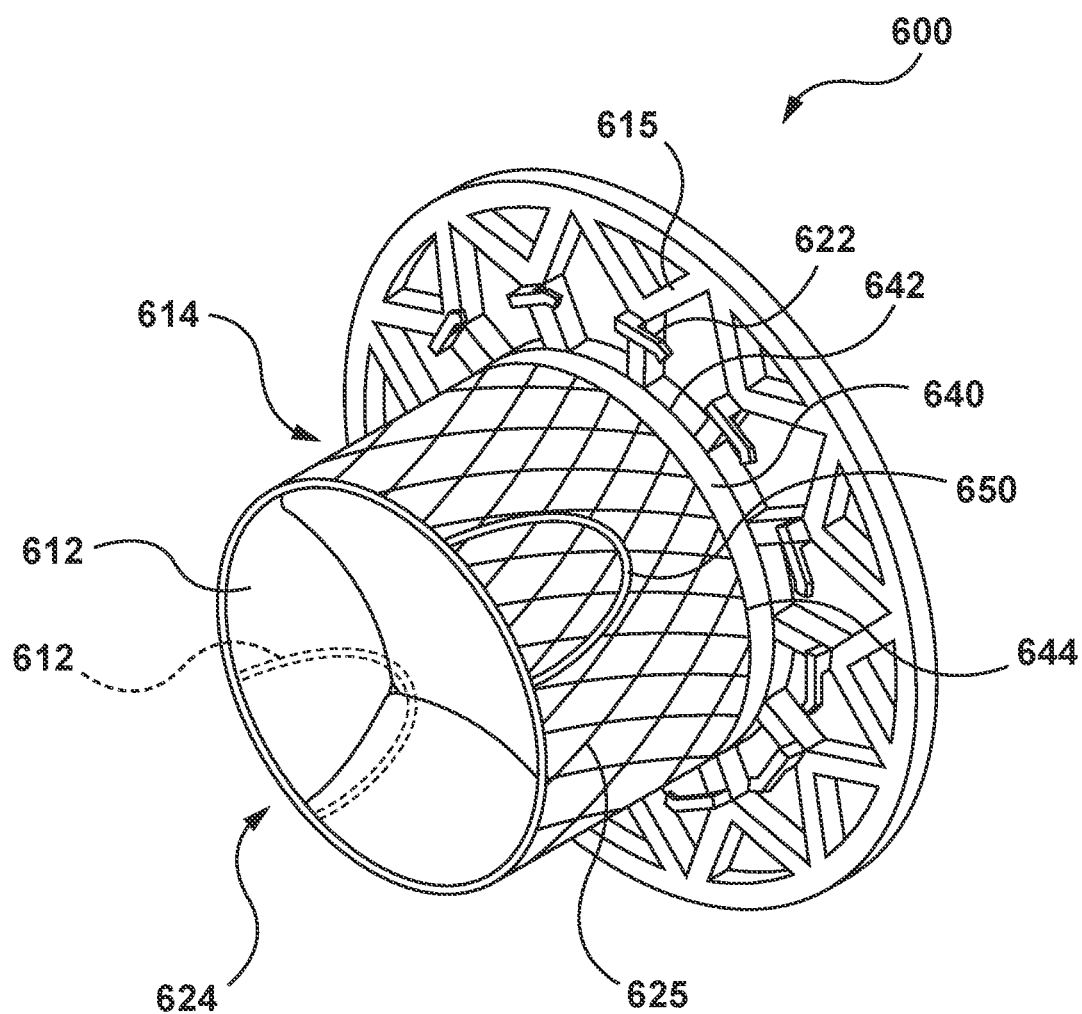
FIG. 35 is a schematic illustration of another embodiment of a heart valve prosthesis including a torque anchoring mechanism.
Figure 36:
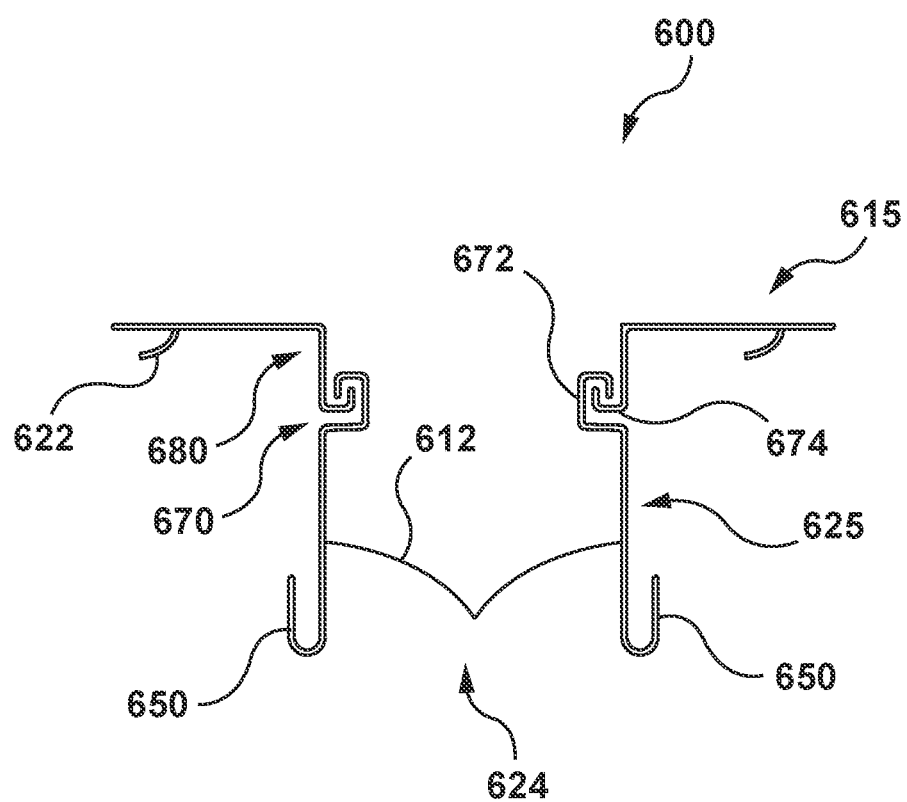
FIG. 36 is a schematic cross-section of a variation of the heart valve prosthesis of FIG. 35.

FIGS. 35-36 schematically show another embodiment of a heart valve prosthesis 600. Heart valve prosthesis 600 is similar to the heart valve prostheses described above, and thus will not be described in detail. Heart valve prosthesis 600 includes a frame 614 and a prosthetic valve 612. Frame 614 defines a central passage 624 in which prosthetic valve 612 is disposed. Frame 614 also defines an inflow rim 615 and an outflow tube 625. Inflow rim 615 includes a plurality of torque anchoring mechanisms 622 coupled thereto, as described above. Heart valve prosthesis 600 also includes a plurality of arms 650 coupled to outflow tube 625. Arms 650 are shown folded back such that arms 650 are disposed outside of an outer surface of outflow tube 625. Each arm 650 may be configured to capture a native leaflet of a native valve between the arm and the outer surface of outflow tube 625. Arms 650 may extending longitudinally away from the outflow end of outflow tube 625 when in the radially compressed delivery configuration, and then fold back into the position shown in FIG. 35 when radially expanded. Using a heart valve prosthesis with arms 650 to capture the native leaflets between the arms 650 and outflow tube 625, it is not desirable to rotate such a heart valve prosthesis to embed torque anchoring mechanisms 622 into tissue adjacent the native valve because such toque is transferred to arms 650 and the native valve leaflets.

Thus, in the embodiment shown in FIG. 35, inflow rim 615 is decoupled from outflow tube 625. By "decoupled", it is meant that inflow rim 615 may be rotated at least partially without rotating outflow tube 625. In the embodiment shown in FIG. 35, inflow rim 615 is decoupled from outflow tube 625 using a joint 640. Joint 640 may be a flexible material such as, but not limited to a fabric material (e.g., polyester, nylon, etc.) A first end 642 of joint 640 is attached to inflow rim 615 and a second end 644 of joint 640 is attached to outflow tube 625. Joint 640 may be coupled to inflow rim 615 and outflow tube 625 by sutures, adhesives, and other connections suitable for the purposes described herein. Using heart valve prosthesis 600 with joint 640, after heart valve prosthesis is radially expanded at the treatment site with the native valve leaflets captured between arms 650 and outflow tube 625, inflow rim 615 may be rotated to embed torque anchoring mechanisms 622 without rotating outflow tube 625. Instead, joint 640 twists to absorb the rotation of inflow rim 615. Inflow rim 615 may be rotated by any of the devices and methods described above.

In another embodiment, instead of joint 640 being a flexible material, inflow rim 615 and outflow tube 625 may be connected to each other in a manner that permits relative rotation there between, but does not permit longitudinal separation. FIG. 36 shows an example of such a joint 670. In the embodiment shown, inflow rim 615 includes a tubular portion 680 extending towards outflow tube 625. An end of tubular portion 680 opposite inflow rim 615 includes a lip 674. Outflow tube 625 includes an end opposite the outflow end with a groove 672. Lip 674 is disposed in groove 672. Such a connection enables inflow rim 615 to rotate relative to outflow tube 625 while keeping inflow rim 615 and outflow tube 625 coupled to each other.

Using heart valve prosthesis 600 with joint 670, after heart valve prosthesis is radially expanded at the treatment site with the native valve leaflets captured between arms 650 and outflow tube 625, inflow rim 615 may be rotated to embed torque anchoring mechanisms 622 without rotating outflow tube 625. Inflow rim 615 may be rotated by any of the devices and methods described above.

While only some embodiments have been described herein, it should be understood that it has been presented by way of illustration and example only, and not limitation. Various changes in form and detail can be made therein without departing from the spirit and scope of the invention, and each feature of the embodiment discussed herein, and of each reference cited herein, can be used in combination with the features of any other embodiment. Further, features of any of the embodiments described herein may be used with any of the other embodiments described herein. All patents and publications discussed herein are incorporated by reference herein in their entirety.

What is claimed is:

1. A heart valve prosthesis comprising:
   a frame including an inflow rim and an outflow portion, wherein the inflow rim flares radially outward from the outflow portion, and wherein the frame is radially compressible and radially expandable;
   a ring disposed around an outer surface of the outflow portion of the frame such that an inner surface of the ring contacts an outer surface of the outflow portion, wherein the ring is rotatable relative to the frame;
   a plurality of barbs extending radially outward from a radially outward surface of the ring; and
   a prosthetic heart valve coupled to an inner surface of the outflow portion of the frame.

2. The heart valve prosthesis of claim 1, wherein each barb includes a distal tip at an end of the barb opposite the ring.

3. The heart valve prosthesis of claim 2, wherein the distal tip of each barb is a sharp tip configured to engage tissue of a heart.

4. The heart valve prosthesis of claim 1, wherein each barb is disposed at a non-zero angle with respect to a radial direction of the ring.

5. The heart valve prosthesis of claim 1, wherein each barb includes a first portion extending directly radially outward from the ring and a second portion disposed at a non-zero angle with respect to a radial direction extending through the first portion of the respective barb.

6. The heart valve prosthesis of claim 5, wherein the angle is in a range of 10 degrees to 90 degrees.

7. The heart valve prosthesis of claim 1, wherein each barb includes a delivery configuration in which an entirety of the barb extends directly radially outwardly from the ring and a deployed configuration in which at least a portion of the barb is disposed at a non-zero angle with respect to a radial direction.

8. The heart valve prosthesis of claim 7, further comprising a plurality of lips, each lip configured to maintain a barb of the plurality of bards in the delivery configuration until a force is applied to overcome a maintaining force of the lips.

9. The heart valve prosthesis of claim 8, wherein the plurality of lips are configured to prevent the ring from rotating until the force is applied to overcome the maintaining force of the lips.

10. The heart valve prosthesis of claim 1, wherein the heart valve prosthesis is configured to restrain the ring from moving longitudinally along the outflow portion of the frame.

11. The heart valve prosthesis of claim 10, wherein the outflow portion of the frame includes a groove in which the ring is disposed to restrain the ring from moving longitudinally along the outflow portion of the frame.

12. The heart valve prosthesis of claim 10, wherein the outflow portion of the frame further includes a lip that restrains longitudinal movement of the ring in a longitudinal direction.

13. A heart valve prosthesis comprising:
    a frame including an inflow rim and an outflow portion, wherein the inflow rim flares radially outward from the outflow portion, and wherein the frame is radially compressible and radially expandable;
    a ring disposed around an outer surface of the outflow portion of the frame, wherein the ring is rotatable relative to the frame;
    a plurality of barbs extending radially outward from an outer surface of the ring, wherein each barb includes a delivery configuration in which an entirety of the barb extends directly radially outwardly from the ring and a deployed configuration in which at least a portion of the barb is disposed at a non-zero angle with respect to a radial direction; and
    a prosthetic heart valve coupled to an inner surface of the outflow portion of the frame.

14. The heart valve prosthesis of claim 13, wherein the non-zero angle is in a range of 10 degrees to 90 degrees.

15. The heart valve prosthesis of claim 13, further comprising a plurality of lips, each lip configured to maintain a barb of the plurality of bards in the delivery configuration until a force is applied to overcome a maintaining force of the lips.

16. The heart valve prosthesis of claim 15, wherein the plurality of lips are configured to prevent the ring from rotating until the force is applied to overcome the maintaining force of the lips.

17. The heart valve prosthesis of claim 13, wherein the heart valve prosthesis is configured to restrain the ring from moving longitudinally along the outflow portion of the frame.

18. The heart valve prosthesis of claim 17, wherein the outflow portion of the frame includes a groove in which the ring is disposed to restrain the ring from moving longitudinally along the outflow portion of the frame.

19. The heart valve prosthesis of claim 17, wherein the outflow portion of the frame further includes a lip that restrains longitudinal movement of the ring in a longitudinal direction.

\* \* \* \* \*